US008283331B2

(12) United States Patent
Gregory et al.

(10) Patent No.: US 8,283,331 B2
(45) Date of Patent: Oct. 9, 2012

(54) METHODS TO REGULATE MIRNA PROCESSING BY TARGETING LIN-28

(75) Inventors: Richard I Gregory, Brookline, MA (US); George Q Daley, Weston, MA (US); Srinivas R Viswanathan, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 106 days.

(21) Appl. No.: 12/682,149

(22) PCT Filed: Oct. 8, 2008

(86) PCT No.: PCT/US2008/079175
§ 371 (c)(1),
(2), (4) Date: Apr. 28, 2010

(87) PCT Pub. No.: WO2009/048932
PCT Pub. Date: Apr. 16, 2009

(65) Prior Publication Data
US 2010/0221266 A1 Sep. 2, 2010

Related U.S. Application Data

(60) Provisional application No. 60/978,610, filed on Oct. 9, 2007, provisional application No. 61/029,718, filed on Feb. 19, 2008.

(51) Int. Cl.
*C12N 15/11* (2006.01)
(52) U.S. Cl. .................................. 514/44 A
(58) Field of Classification Search ............ 514/44 A
See application file for complete search history.

(56) References Cited

U.S. PATENT DOCUMENTS

2007/0287678 A1* 12/2007 Slack et al. ............... 514/44
2009/0192102 A1* 7/2009 Bader et al. .............. 514/44

OTHER PUBLICATIONS

Hutvagner et al. PLoS Biology 2, 0465-0475, 2004.*
Lee et al. The Journal of Biological Chemistry 280, 16635-16641, 2006.*
Sempere et al. Genome Biology 2004, 5, R13, pp. 1-11.*
Guo, Y. et al., "Identification and characterization of lin-28 homolog B (LIN28B) in human hepatocellular carcinoma." Gene 384:51-61, 2006.
Büssing, I. et al., "let-7 microRNAs in development, stem cells and cancer." Trends in Molecular Medicine 14 (9):400-409, 2008.
Newman, M.A. et al., "Lin-28 interaction with the Let-7 precursor loop mediates regulated microRNA processing." RNA 14:1539-1549, 2008.
Viswanathan, S.R. et al., "Selective Blockade of MicroRNA Processing by Lin28." Science 320:97-100, 2008.
Rybak, A. et al., "A feedback loop comprising lin-28 and let-7 controls pre-let-7 maturation during neural stem-cell commitment." Nature Cell Biology 10(8):987-993, 2008.
Thomson, J.M. et al., "Extensive post-transcriptional regulation of microRNAs and its implications for cancer." Genes & Development 20:2202-2207, 2006.
Kumar, M. S. et al., "Impaired microRNA processing enhances cellular transformation and tumorigenesis." Nature Genetics 39(5):673-677, 2007.

* cited by examiner

*Primary Examiner* — Brian Whiteman
(74) *Attorney, Agent, or Firm* — Wolf, Greenfield & Sacks, P.C.

(57) ABSTRACT

The present invention relates generally to methods to regulate microRNA (miRNA) biogenesis, in particular the regulation of the processing of pri-miRNA to mature miRNA by Lin-28 and/or variants such as Lin28B. In particular, the present invention relates to methods and compositions comprising at least one agent which inhibits Lin-28 function or activity and/or expression to increase the processing of pri-mRNA to mature miRNA. More specifically, one aspect of the invention is directed to treating and/or preventing cancer in a subject by administering an agent that inhibits Lin-28 activity or expression to a subject, preferably a human subject.

21 Claims, 47 Drawing Sheets

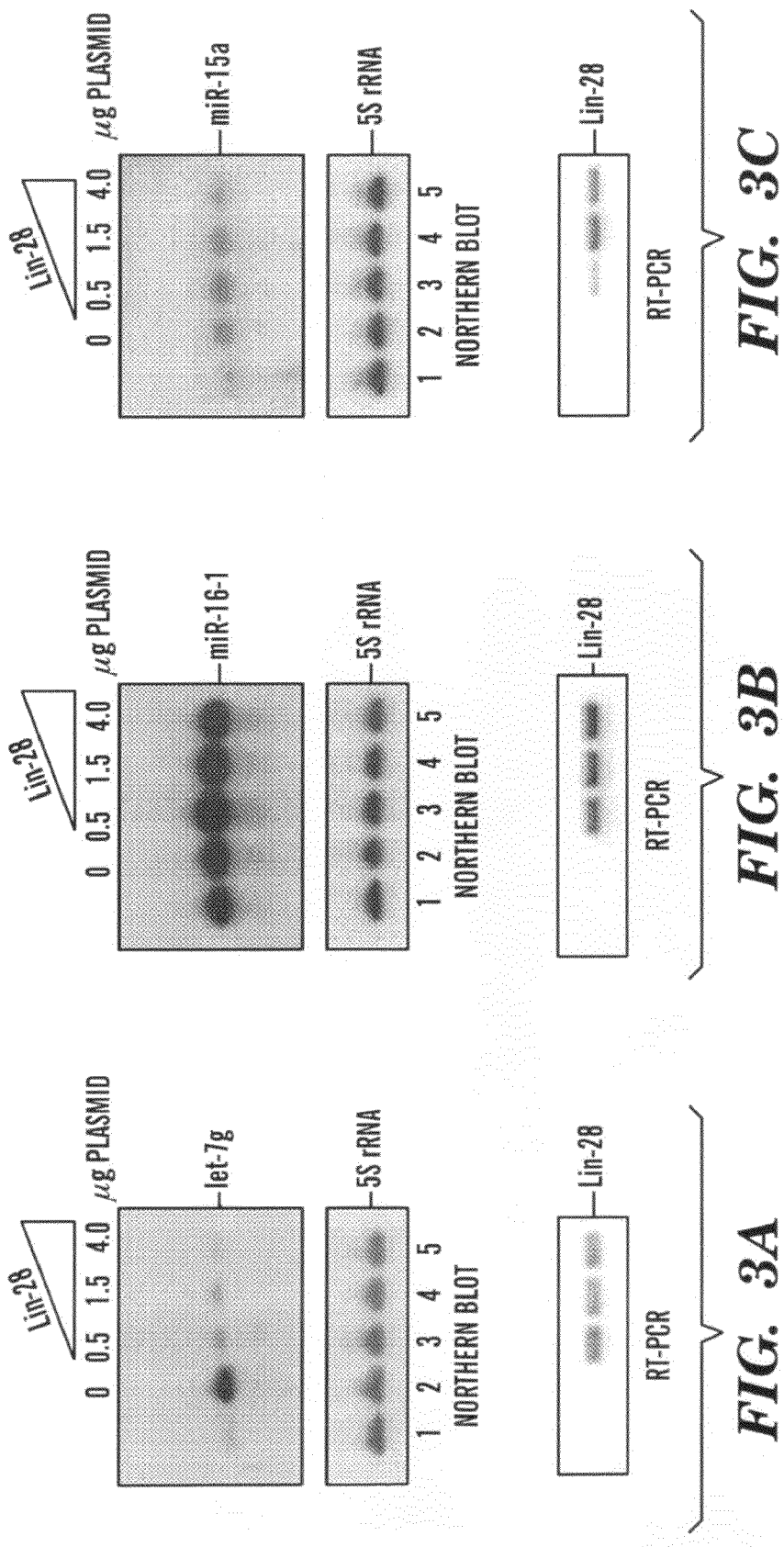

| 1 | 2 | 3 |
|---|---|---|
| RNA HelicaseA | SNRP70 | HNRPA1 |
| SFPQ | PSPC1 | NONO |
| DHX36 | HNRPL | HNRPA3 |
| XRN2 | HNRPK | LIN-28 |
| ILF3 (NF90) |  | YBX1 |
| DDX1 |  | HNRPA2/B1 |
| DDX3X |  | ILF2 |
| HNRPU |  | THOC4 |
| DDX37 |  | HNRPA/B |
| RNABP FUS |  | CLE7 |
| DDX5 (p68) |  | BAT1 |
| EWS |  | TIAL1 |
| IGF2BP1 |  | PUR-beta |
| DHX15 |  | HNRPH |
| HNRPU-like |  | LIN-28B |
| DDX17 (p72) |  | DKC1 |
|  |  | SNRPN |

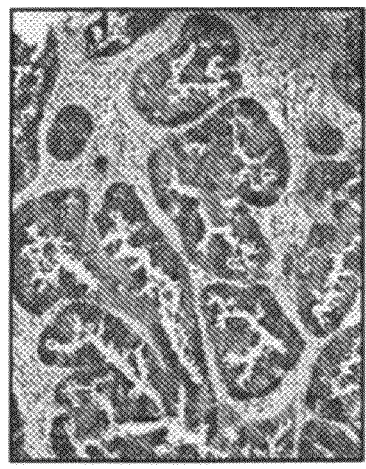
FIG. 17Ei
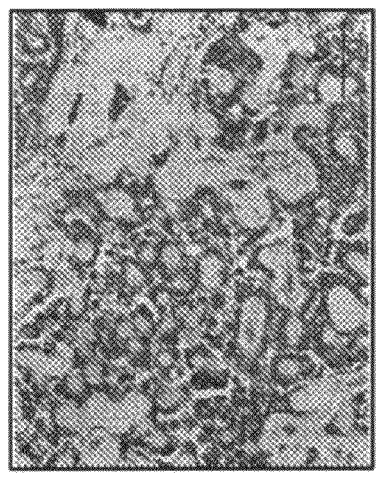
FIG. 17Eii
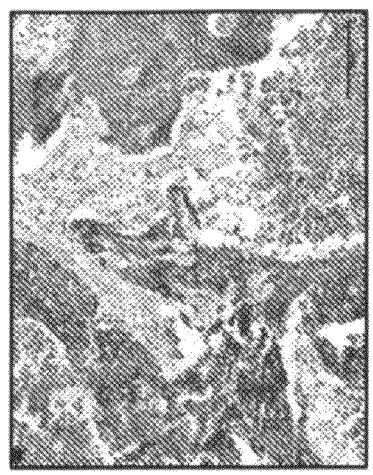
FIG. 17Eiii
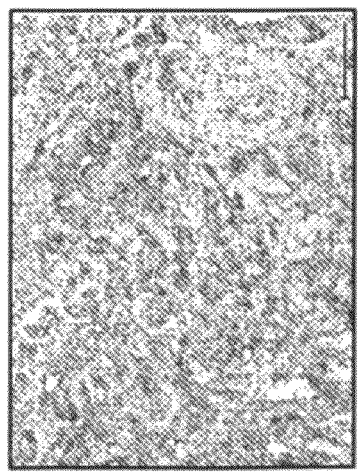
FIG. 17Eiv
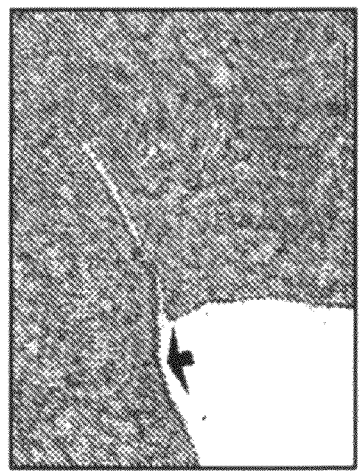
FIG. 17Ev
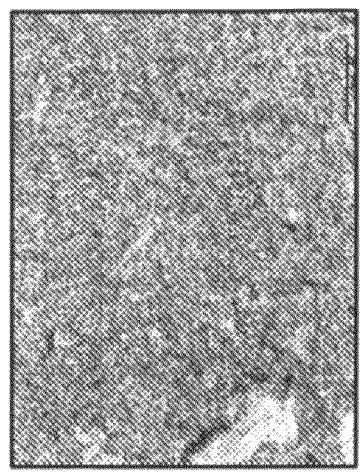
FIG. 17Evi

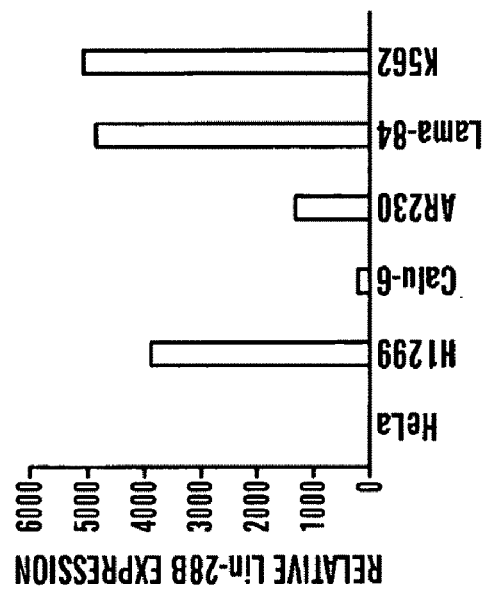
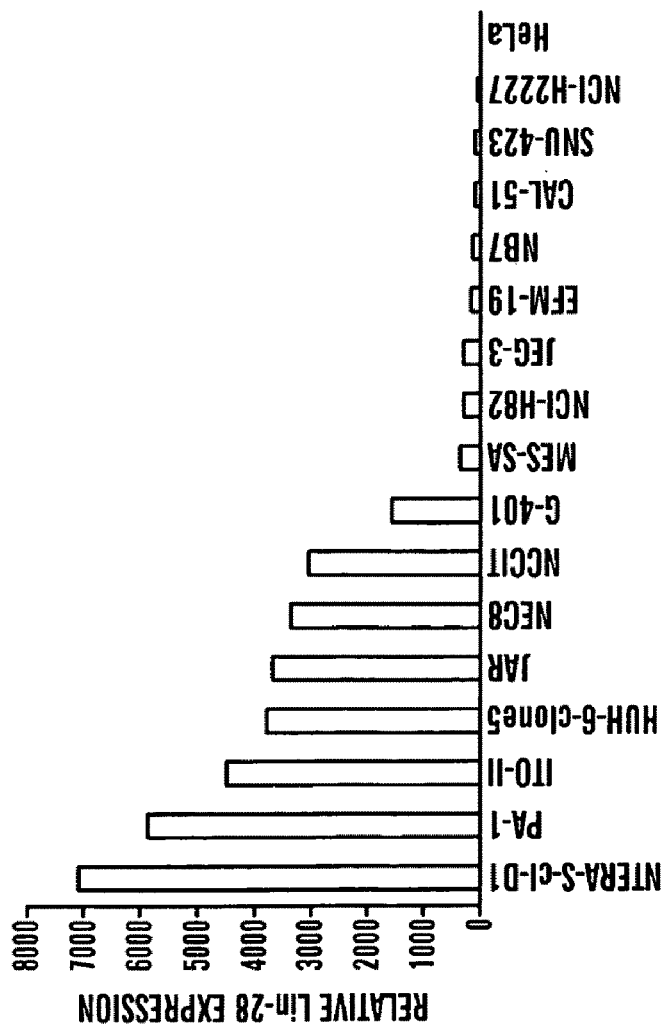
FIG. 21Ai
FIG. 21Aii ated Oct. 8, 2008, which designated the U.S., and

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
gtacggtgtg gacctcatca                                              20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tcttgctgtg tccaggaaag                                              20
```

```
<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
cagaaggaga ttactgctct ggct                                              24

<210> SEQ ID NO 4
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
tactcctgct tgctgatcca catc                                              24

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
aggcggtgga gttcaccttt aaga                                              24

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
agcttgcatt ccttggcatg atgg                                              24

<210> SEQ ID NO 7
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ccggcccagt aagaatgcaa cttaactcga gttaagttgc attcttactg ggttttg         58

<210> SEQ ID NO 8
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide "
```

```
<400> SEQUENCE: 8
ccggcaaagg agacaggtgc tacaactcga gttgtagcac ctgtctcctt tgttttttg        58

<210> SEQ ID NO 9
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide "

<400> SEQUENCE: 9
ccggcatctg taagtggttc aacgtctcga gacgttgaac cacttacaga tgttttttg        58

<210> SEQ ID NO 10
<211> LENGTH: 3459
<212> TYPE: DNA
<213> ORGANISM: Homo sapiens

<400> SEQUENCE: 10
cctttgcctt cggacttctc cggggccagc agccgcccga ccaggggccc ggggccacgg        60
gctcagccga cgaccatggg ctccgtgtcc aaccagcagt ttgcaggtgg ctgcgccaag       120
gcggcagaag aggcgcccga ggaggcgccg gaggacgcgg cccgggcggc ggacgagcct       180
cagctgctgc acggtgcggg catctgtaag tggttcaacg tgcgcatggg gttcggcttc       240
ctgtccatga ccgcccgcgc cggggtcgcg ctcgaccccc cagtggatgt ctttgtgcac       300
cagagtaagc tgcacatgga agggttccgg agcttgaagg agggtgaggc agtggagttc       360
acctttaaga agtcagccaa gggtctggaa tccatccgtg tcaccggacc tggtggagta       420
ttctgtattg ggagtgagag gcggccaaaa ggaaagagca tgcagaagcg cagatcaaaa       480
ggagacaggt gctacaactg tggaggtcta gatcatcatg ccaaggaatg caagctgcca       540
ccccagccca agaagtgcca cttctgccag agcatcagcc atatggtagc ctcatgtccg       600
ctgaaggccc agcagggccc tagtgcacag ggaaagccaa cctactttcg agaggaagaa       660
gaagaaatcc acagccctac cctgctcccg gaggcacaga attgagccac aatgggtggg       720
ggctattctt ttgctatcag gaagttttga ggagcaggca gagtggagaa agtgggaata       780
gggtgcattg gggctagttg gcactgccat gtatctcagg cttgggttca caccatcacc       840 cttttcttccc tctaggtggg gggaaagggt gagtcaaagg aactccaacc atgctctgtc       900
caaatgcaag tgagggttct gggggcaacc aggagggggg aatcacccta caacctgcat       960 atttttgagtc tccatcccca gaatttccag cttttgaaag tggcctggat agggaagttg      1020 ttttccttttt aaagaaggat atataataat tccatgccca gagtgaaatg attaagtata      1080
agaccagatt catggagcca agccactaca ttctgtggaa ggagatctct caggagtaag      1140
cattgttttt ttttcacatc ttgtatcctc atacccactt ttgggatagg gtgctggcag      1200
ctgtcccaag caatgggtaa tgatgatggc aaaaagggtg tttgggggaa cagctgcaga      1260
cctgctgctc tatgctcacc cccgcccccat tctgggccaa tgtgatttta tttatttgct      1320
cccttggata ctgcacctttg ggtcccactt tctccaggat gccaactgca ctagctgtgt      1380
gcgaatgacg tatcttgtgc attttaactt ttttttccttta atataaatat tctggttttg      1440 tattttttgta tatttttaatc taaggccctc atttcctgca ctgtgttctc aggtacatga      1500
gcaatctcag ggatagccag cagcagctcc aggtctgcgc agcaggaatt acttttttgtt      1560 gttttttgcca ccgtggagag caactatttg gagtgcacag cctattgaac tacctcattt      1620
```

-continued

```
ttgccaataa gagctggctt ttctgccata gtgtcctctt gaaacccct ctgccttgaa      1680 aatgttttat gggagactag gttttaactg ggtggcccca tgacttgatt gccttctact      1740
ggaagattgg gaattagtct aaacaggaaa tggtggtaca cagaggctag gagaggctgg      1800
gcccggtgaa aaggccagag agcaagccaa gattaggtga gggttgtcta atcctatggc      1860
acaggacgtg ctttacatct ccagatctgt tcttcaccag attaggttag gcctaccatg      1920
tgccacaggt gtgtgtgtg tttgtaaaac tagagttgct aaggataagt ttaaagacca      1980 ataccctgt acttaatcct gtgctgtcga gggatggata tatgaagtaa ggtgagatcc      2040
ttaacctttc aaaattttcg ggttccaggg agacacacaa gcgagggttt tgtggtgcct      2100
ggagcctgtg tcctgccctg ctacagtagt gattaatagt gtcatggtag ctaaaggaga      2160
aaaagggggt ttcgtttaca cgctgtgaga tcaccgcaaa cctaccttac tgtgttgaaa      2220
cgggacaaat gcaatagaac gcattgggtg gtgtgtgtct gatcctgggt tcttgtctcc      2280
cctaaatgct gcccccaag ttactgtatt tgtctgggct ttgtaggact tcactacgtt      2340
gattgctagg tggcctagtt tgtgtaaata taatgtattg gtctttctcc gtgttctttg      2400
ggggttttgt ttacaaactt cttttttgtat tgagagaaaa atagccaaag catctttgac      2460
agaaggttct gcaccaggca aaaagatctg aaacattagt ttggggggcc ctcttcttaa      2520 agggggatc ttgaaccatc ctttcttttg tattcccctt cccctattac ctattagacc      2580
agatcttctg tcctaaaaac ttgtcttcta ccctgccctc ttttctgttc accccaaaa      2640 gaaaacttac acaccacac acatacacat ttcatgcttg gagtgtctcc acaactctta      2700
aatgatgtat gcaaaaatac tgaagctagg aaaaccctcc gtcccttgtt cccaacctcc      2760
taagtcaaga ccattaccat ttctttcttt ctttttttt ttttttttaa agtggagtct      2820
cgctgtgtca cccaggcaga ggttgcagtg agctgagatc gcaccactgc actccagcct      2880
ggttacagag cgagactctg tctcaaacaa aacaaaacaa aacaaaaaca cactactgta      2940
ttttggatgg atcaaacctc cttaatttta atttctaatc ctaaagtaaa gagatgcaat      3000 tggggggcctt ccatgtagaa agtggggtca ggaggccaag aaagggaata tgaatgtata      3060
tccaagtcac tcaggaactt ttatgcaggt gctagaaact ttatgtcaaa gtggccacaa      3120
gattgtttaa taggagacga acgaatgtaa ctccatgttt actgctaaaa accaaagctt      3180
tgtgtaaaat cttgaattta tggggcggga gggtaggaaa gcctgtacct gtctgttttt      3240
ttcctgatcc ttttcctca ttcctgaact gcaggagact gagcccttt gggctttggt      3300 gaccccatca ctggggtgtg tttatttgat ggttgatttt gctgtactgg gtacttcctt      3360
tcccattttc taatcatttt ttaacacaag ctgactcttc ccttcccttc tcctttccct      3420
gggaaaatac aatgaataaa taaagactta ttggtacgc                             3459
```

<210> SEQ ID NO 11
<211> LENGTH: 4014
<212> TYPE: DNA
<213> ORGANISM: Homo sapiens

<400> SEQUENCE: 11

```
gtgcggggga agatgtagca gcttcttctc cgaaccaacc ctttgccttc ggacttctcc        60
ggggccagca gccgcccgac caggggcccg gggccacggg ctcagccgac gaccatgggc       120
tccgtgtcca accagcagtt tgcaggtggc tgcgccaagg cggcagaaga ggcgcccgag       180
gaggcgccgg aggacgcggc ccgggcggcg gacgagcctc agctgctgca cggtgcgggc       240
atctgtaagt ggttcaacgt gcgcatgggg ttcggcttcc tgtccatgac cgcccgcgcc       300
```

-continued

```
ggggtcgcgc tcgaccccccc agtggatgtc tttgtgcacc agagtaagct gcacatggaa    360
gggttccgga gcttgaagga gggtgaggca gtggagttca cctttaagaa gtcagccaag    420
ggtctggaat ccatccgtgt caccggacct ggtggagtat tctgtattgg gagtgagagg    480
cggccaaaag gaaagagcat gcagaagcgc agatcaaaag gagacaggtg ctacaactgt    540
ggaggtctag atcatcatgc caaggaatgc aagctgccac cccagcccaa gaagtgccac    600
ttctgccaga gcatcagcca tatggtagcc tcatgtccgc tgaaggccca gcagggccct    660
agtgcacagg gaaagccaac ctactttcga gaggaagaag aagaaatcca cagccctacc    720
ctgctcccgg aggcacagaa ttgagccaca atgggtgggg gctattcttt tgctatcagg    780
aagtttgag gagcaggcag agtggagaaa gtgggaatag ggtgcattgg ggctagttgg    840
cactgccatg tatctcaggc ttgggttcac accatcaccc tttcttccct ctaggtgggg    900
ggaaagggtg agtcaaagga actccaacca tgctctgtcc aaatgcaagt gagggttctg    960
ggggcaacca ggagggggga atcaccctac aacctgcata ctttgagtct ccatccccag   1020
aatttccagc ttttgaaagt ggcctggata gggaagttgt tttccttta agaaggata    1080
tataataatt cccatgccag agtgaaatga ttaagtataa accagattc atggagccaa    1140
gccactacat tctgtggaag gagatctctc aggagtaagc attgtttttt tttcacatct    1200
tgtatcctca tacccacttt tgggataggg tgctggcagc tgtcccaagc aatgggtaat    1260
gatgatggca aaagggtgt ttgggggaac agctgcagac ctgctgctct atgctcaccc    1320
ccgcccatt ctgggccaat gtgatttat ttatttgctc ccttggatac tgcaccttgg    1380
gtcccacttt ctccaggatg ccaactgcac tagctgtgtg cgaatgacgt atcttgtgca    1440
tttaacttt ttttccttaa tataaatatt ctggttttgt attttttgtat attttaatct    1500
aaggccctca tttcctgcac tgtgttctca ggtacatgag caatctcagg gatagccagc    1560
agcagctcca ggtctgcgca gcaggaatta cttttttgttg tttttgccac cgtggagagc    1620
aactatttgg agtgcacagc ctattgaact acctcatttt tgccaataag agctggcttt    1680
tctgccatag tgtcctcttg aaaccccctc tgccttgaaa atgttttatg ggagactagg    1740
ttttaactgg gtggccccat gacttgattg ccttctactg gaagattggg aattagtcta    1800
aacaggaaat ggtggtacac agaggctagg agaggctggg cccggtgaaa aggccagaga    1860
gcaagccaag attaggtgag ggttgtctaa tcctatggca caggacgtgc tttacatctc    1920
cagatctgtt cttcaccaga ttaggttagg cctaccatgt gccacagggt gtgtgtgtgt    1980
ttgtaaaact agagttgcta aggataagtt taaagaccaa taccctgta cttaatcctg    2040
tgctgtcgag ggatggatat atgaagtaag gtgagatcct taacctttca aaattttcgg    2100
gttccaggga gacacacaag cgagggtttt gtggtgcctg gagcctgtgt cctgccctgc    2160
tacagtagtg attaatagtg tcatggtagc taaaggagaa aaaggggggtt tcgtttacac    2220
gctgtgagat caccgcaaac ctaccttact gtgttgaaac gggacaaatg caatagaacg    2280
cattgggtgg tgtgtgtctg atcctggggtt cttgtctccc ctaaatgctg ccccccaagt    2340
tactgtattt gtctgggctt tgtaggactt cactacgttg attgctaggt ggcctagttt    2400
gtgtaaatat aatgtattgg tctttctccg tgttctttgg gggttttgtt tacaaacttc    2460
ttttttgtatt gagagaaaaa tagccaaagc atctttgaca gaaggttctg caccaggcaa    2520
aaagatctga acattagtt tgggggggccc tcttcttaaa gtgggggatct tgaaccatcc    2580
tttcttttgt attccccttc ccctattacc tattagacca gatcttctgt cctaaaaact    2640
tgtcttctac cctgccctct tttctgttca cccccaaaag aaaacttaca cacccacaca    2700
```

-continued

```
catacacatt tcatgcttgg agtgtctcca caactcttaa atgatgtatg caaaatact    2760 gaagctagga aaaccctcca tcccttgttc ccaacctcct aagtcaagac cattaccatt    2820
tctttctttc ttttttttt tttttttaaaa tggagtctca ctgtgtcacc caggctggag    2880
tgcagtggca tgatcggctc actgcagcct ctgcctcttg ggttcaagtg attctcctgc    2940
ctcagcctcc tgagtagctg ggatttcagg caccogccac actcagctaa ttttgtatt     3000 tttagtagag acgggtttc accatgttgt ccaggctggt ctggaactcc tgacctcagg    3060
tgatctgccc accttggctt cccaaagtgc tgggattaca ggcatgagcc accatgctgg    3120
gccaaccatt tcttggtgta ttcatgccaa acacttaaga cactgctgta gcccaggcgc    3180
ggtggctcac acctgtaatc ccagcacttt ggaaggctga ggcgggcgga tcacaaggtc    3240
acgagttcaa aactatcctg gccaacacag tgaaacccg tctctactaa aatacaaaaa     3300
aattagccgg gtgtggtggt gcatgccttt agtcctagct attcaggagg ctgaggcagg    3360
ggaatcgctt gaacccgaga ggcagaggtt gcagtgagct gagatcgcac cactgcactc    3420
cagcctggtt acagagcaag actctgtctc aaacaaaaca aaacaaaaca aaacacact     3480 actgtatttt ggatggatca aacctcctta attttaattt ctaatcctaa agtaaagaga    3540
tgcaattggg ggccttccat gtagaaagtg gggtcaggag gccaagaaag ggaatatgaa    3600
tgtatatcca agtcactcag gaactttat gcaggtgcta gaaactttat gtcaaagtgg     3660
ccacaagatt gtttaatagg agacgaacga atgtaactcc atgtttactg ctaaaaacca    3720
aagctttgtg taaaatcttg aatttatggg gcgggagggt aggaaagcct gtacctgtct    3780 gttttttcc tgatccttt ccctcattcc tgaactgcag gagactgagc ccctttgggc      3840
tttggtgacc ccatcactgg ggtgtgttta tttgatggtt gattttgctg tactgggtac    3900
ttcctttccc attttctaat catttttaa cacaagctga ctcttccctt cccttctcct    3960
ttccctggga aaatacaatg aataaataaa gacttattgg tacgcaaact gtca          4014
```

<210> SEQ ID NO 12
<211> LENGTH: 209
<212> TYPE: PRT
<213> ORGANISM: Homo sapiens

<400> SEQUENCE: 12

```
Met Gly Ser Val Ser Asn Gln Gln Phe Ala Gly Gly Cys Ala Lys Ala
1               5                   10                  15

Ala Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
        115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
```

-continued

```
                145                 150                 155                 160
Cys His Phe Cys Gln Ser Ile Ser His Met Val Ala Ser Cys Pro Leu
                165                 170                 175
Lys Ala Gln Gln Gly Pro Ser Ala Gln Gly Lys Pro Thr Tyr Phe Arg
                180                 185                 190
Glu Glu Glu Glu Ile His Ser Pro Thr Leu Leu Pro Glu Ala Gln
                195                 200                 205
Asn

<210> SEQ ID NO 13
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ugagguagua gguuguauag uu                                              22

<210> SEQ ID NO 14
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ugagguagua gguugugugg uu                                              22

<210> SEQ ID NO 15
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ugagguagua gguuguaugg uu                                              22

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
agagguagua gguugcauag u                                               21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
```

-continued

```
ugagguagga gguuguauag u                                        21

<210> SEQ ID NO 18
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ugagguagua gauuguauag uu                                       22

<210> SEQ ID NO 19
<211> LENGTH: 80
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ugggaugagg uaguagguug uauaguuuua gggucacacc caccacuggg agauaacuau    60
acaaucuacu gucuuuccua                                          80

<210> SEQ ID NO 20
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ctccaaatat ggtaaagatg aggcaaatgt gtgg                          34

<210> SEQ ID NO 21
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
gacaaccaca atgcatttct ggttattcta gtgcc                         35

<210> SEQ ID NO 22
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ggaaatactt tttattctgc tgaaagccta taaaattatg c                  41

<210> SEQ ID NO 23
<211> LENGTH: 39
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 23
gtattgccaa ccttacttca gcagcacagt caatactgg                                  39

<210> SEQ ID NO 24
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
ctgaggtagt agtttgtaca gttctgttga atctcatgga ctgtacaggc cactgccttg           60

<210> SEQ ID NO 25
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
caaggcagtg gcctgtacag tccatgagat tcaacagaac tgtacaaact actacctcag          60

<210> SEQ ID NO 26
<211> LENGTH: 250
<212> TYPE: PRT
<213> ORGANISM: Homo sapiens

<400> SEQUENCE: 26
```

Met Ala Glu Gly Gly Ala Ser Lys Gly Gly Glu Glu Pro Gly Lys
1               5                   10                  15

Leu Pro Glu Pro Ala Glu Glu Ser Gln Val Leu Arg Gly Thr Gly
                20                  25                  30

His Cys Lys Trp Phe Asn Val Arg Met Gly Phe Gly Phe Ile Ser Met
            35                  40                  45

Ile Asn Arg Glu Gly Ser Pro Leu Asp Ile Pro Val Asp Val Phe Val
        50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg
                100                 105                 110

Arg Pro Lys Gly Lys Thr Leu Gln Lys Arg Lys Pro Lys Gly Asp Arg
            115                 120                 125

Cys Tyr Asn Cys Gly Gly Leu Asp His His Ala Lys Glu Cys Ser Leu
        130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Ala Ser Ser
                165                 170                 175

Gln Gly Arg Gln Glu Ala Glu Ser Gln Pro Cys Thr Ser Thr Leu Pro
            180                 185                 190

```
Arg Glu Val Gly Gly His Gly Cys Thr Ser Pro Pro Phe Pro Gln
        195                 200                 205

Glu Ala Arg Ala Glu Ile Ser Glu Arg Ser Gly Arg Ser Pro Gln Glu
210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 27
<211> LENGTH: 180
<212> TYPE: PRT
<213> ORGANISM: Homo sapiens

<400> SEQUENCE: 27

Met Glu Gly Phe Arg Ser Leu Lys Glu Gly Glu Pro Val Glu Phe Thr
1               5                   10                  15

Phe Lys Lys Ser Ser Lys Gly Leu Glu Ser Ile Arg Val Thr Gly Pro
                20                  25                  30

Gly Gly Ser Pro Cys Leu Gly Ser Glu Arg Arg Pro Lys Gly Lys Thr
            35                  40                  45

Leu Gln Lys Arg Lys Pro Lys Gly Asp Arg Cys Tyr Asn Cys Gly Gly
    50                  55                  60

Leu Asp His His Ala Lys Glu Cys Ser Leu Pro Pro Gln Pro Lys Lys
65                  70                  75                  80

Cys His Tyr Cys Gln Ser Ile Met His Met Val Ala Asn Cys Pro His
                85                  90                  95

Lys Asn Val Ala Gln Pro Pro Ala Ser Ser Gln Gly Arg Gln Glu Ala
                100                 105                 110

Glu Ser Gln Pro Cys Thr Ser Thr Leu Pro Arg Glu Val Gly Gly Gly
            115                 120                 125

His Gly Cys Thr Ser Pro Pro Phe Pro Gln Glu Ala Arg Ala Glu Ile
    130                 135                 140

Ser Glu Arg Ser Gly Arg Ser Pro Gln Glu Ala Ser Ser Thr Lys Ser
145                 150                 155                 160

Ser Ile Ala Pro Glu Glu Gln Ser Lys Lys Gly Pro Ser Val Gln Lys
                165                 170                 175

Arg Lys Lys Thr
            180

<210> SEQ ID NO 28
<211> LENGTH: 3120
<212> TYPE: DNA
<213> ORGANISM: Homo sapiens

<400> SEQUENCE: 28
aattgacaaa gtcacgtgtg ctcaggggc cagaaactgg agagaggaga gaaaaaaat      60 caaaagaagg aaagcacatt agaccatgcg agctaaattt gtgatcgcac aaaatcaaga     120
tgttagattg atgcagaaga tcactccgtt ccaaggggaa agttttcatc tcacgagttt     180
ggagctgagg gcccgtgggg caacatggcc gaaggcgggg ctagcaaagg tggtggagaa     240
gagcccggga agctgccgga gccggcagag gaggaatccc aggttttgcg cggaactggc     300
cactgtaagt ggttcaatgt gcgcatggga tttggattca tctccatgat aaaccgagag     360 ggaagccct tggatattcc agtcgatgta tttgtacacc aaagcaaact attcatggaa      420
ggatttagaa gcctaaaaga aggagaacca gtggaattca catttaaaaa atcttccaaa     480
```

```
ggccttgagt caatacgggt aacaggacct ggtgggagcc cctgtttagg aagtgaaaga    540
agacccaaag ggaagacact acagaaaaga aaaccaaagg gagatagatg ctacaactgt    600
ggtggccttg atcatcatgc taaggaatgt agtctaccte ctcagccaaa gaagtgccat    660
tactgtcaga gcatcatgca catggtggca aactgcccac ataaaaatgt tgcacagcca    720
cccgcgagtt ctcagggaag acaggaagca gaatcccagc catgcacttc aactctccct    780
cgagaagtgg gaggcgggca tggctgtaca tcaccaccgt ttcctcagga ggctagggca    840
gagatctcag aacggtcagg caggtcacct caagaagctt cctccacgaa gtcatctata    900
gcaccagaag agcaaagcaa aaaggggcct tcagttcaaa aaggaaaaa gacataacag     960 gtcttcttca tatgttcttt cctttacccg gttgcaaagt ctacctcatg caagtatagg   1020
ggaacagtat ttcacaagca gtagctgacc tgggatttta actactattg gggaactgtg   1080 aatttttaa acagacaaat cactctaagc aaattacatt tgagcagggt gtcatgtttt   1140
atgttaattc agagaataag atactatgtc tgtcaatatg tgcatgtgtg agagggagag   1200
agcctgagtc tgtgtgtgta catgaggatt tttatatagg aatgtagaca catatataaa   1260
gaggctttgt ctttatatat ttgtgtatag atcaaagcac acaccctctc tcatataatt   1320
ggatatttcc aagaattgaa aacccatgtg aagcattata gatagtttta aatttaaccc   1380
actggagttt tcttgaaata ccacttcttt tatattatat aaaactaaaa acacgactgt   1440 tacctttgt gtgaaccaaa ggatacttca gatctcagag ctgccaatta tggggtacta    1500
aaggttttta agacatccag ttctcccgaa tttgggattg cctctttttc ttgaaatctc   1560
tggagtagta attttttcc ccctttttg aaggcagtac cttaacttca tatgcctctg    1620
actgccataa gctttttga ttctgggata acataactcc agaaaagaca atgaatgtgt    1680
aatttgggcc gatatttcac tgttttaaat tctgtgttta attgtaaaat tagatgccta   1740
ttaagagaaa tgaaggggag gatcatctta gtggcttgtt ttcagtagta ttttaatatc   1800
agcttcttgt aaccttttcc atgttgtgag ggttgtaagg gattgtgtgg caacagcagc   1860
ttcccttggc taactcaatc ttctacccat tgcttagagc aggggagccct ccttattac   1920 tactgaagac cttagagaac tccaattgtt tggcatatat ttttggtggt ggttttatt    1980 cctcctggag agttatctaa tttgtttcta aaacaaacaa gcagcaaaga atgaattaa    2040 atactggggt tgagaattaa aattaagtgg atgttcacag ttgcccaata tatatgacct   2100
gcaaatgata cgaaaaagtg cagcatttag tggcagttaa caagagtgac aagcctgggg   2160
cagaggtacc aaacctctcc caccagagag ctagaagtat tttatacagt aactttgatc   2220
ttatggaagt gaccttcaat gcttattctg aagtaaccta tatggtggat acaggatgaa   2280
cattcagtgc cagggagaat cttctcaggt tggttctcgt tagagtgata aactggctag   2340
gggccatagt attggtcctg ttaggtttcg gtcatggaaa aaaaaaatat tttgggggtca   2400 tcctggctct agatgttatg ggcaaatttc tgaaacatct gcaagaaggt accagttaat   2460
tatagtgctt aatattggga ataagattaa gcattataat tataatgtat gggcctgttg   2520
gtgtaagctc agataattaa ataaaaatag catgactcaa atgagacata ttctgctgaa   2580
cagtttctac ttcctctccc gcctgtcctg tcatgggaga cgtgtatagt tgctgctgtt   2640
tcagcaaacc accataagac gaaaatgcct caggttgggt tgccagtcct ttacaactca   2700
gcttgaattt cacaacagtg attgtgagaa tctgcgtggt atacactgaa atatcggtgt   2760
gctgtgatgc aaaacttgcc tttgacgata ttgaatgtga tatagctgta gagaagtact   2820
tccttgcctt atgtgaggat ttcaaactta tttaaattat gtagacaaat caaagtggca   2880
```

| | |
|---|---|
| ttgcttaatt tttagcaggc ataataagca agttaacagt aaaatgcaaa acatgataag | 2940 |
| cgttgctcaa tttttagcag gtataataag caggttaaca gtaaaaatgc aaaacatgat | 3000 |
| agataagtca ctttgaaaat tcaaaccaaa gttccttcac cttatggaaa taggaaatta | 3060 |
| tggacttcaa aattggacac ttcctgttta caaaagaaa ttcagagcta aaatcatggt | 3120 |

<210> SEQ ID NO 29
<211> LENGTH: 5504
<212> TYPE: DNA
<213> ORGANISM: Homo sapiens

<400> SEQUENCE: 29

| | |
|---|---|
| aattgacaaa gtcacgtgtg ctcaggggc cagaaactgg agagaggaga gaaaaaaatc | 60 |
| aaaagaagga aagcacatta gaccatgcga gctaaatttg tgatcgcaca aaatcaagat | 120 |
| gttagattga tgcagaagat cactccgttc caaagggaaa gttttcatct cacgagtttg | 180 |
| gagctgaggg cccgtggggc aacatggccg aaggcggggc tagcaaaggt ggtggagaag | 240 |
| agcccgggaa gctgccggag ccggcagagg aggaatccca ggttttgcgc ggaactggcc | 300 |
| actgtaagtg gttcaatgtg cgcatgggat ttggattcat ctccatgata aaccgagagg | 360 |
| gaagccctt ggatattcca gtcgatgtat ttgtacacca aagcaaacta ttcatggaag | 420 |
| gatttagaag cctaaaagaa ggagaaccag tggaattcac atttaaaaaa tcttccaaag | 480 |
| gccttgagtc aatacgggta acaggacctg gtgggagccc ctgtttagga agtgaaagaa | 540 |
| gacccaaagg gaagacacta cagaaaagaa aaccaaaggg agatagatgc tacaactgtg | 600 |
| gtggccttga tcatcatgct aaggaatgta gtctacctcc tcagccaaag aagtgccatt | 660 |
| actgtcagag catcatgcac atggtggcaa actgcccaca taaaaatgtt gcacagccac | 720 |
| ccgcgagttc tcagggaaga caggaagcag aatcccagcc atgcacttca actctccctc | 780 |
| gagaagtggg aggcgggcat ggctgtacat caccaccgtt tcctcaggag gctagggcag | 840 |
| agatctcaga acggtcaggc aggtcacctc aagaagcttc ctccacgaag tcatctatag | 900 |
| caccagaaga gcaaagcaaa aaggggcctt cagttcaaaa aaggaaaaag acataacagg | 960 |
| tcttcttcat atgttctttc ctttacccgg ttgcaaagtc tacctcatgc aagtatagg | 1020 |
| gaacagtatt tcacaagcag tagctgacct gggattttaa ctactattgg ggaactgtga | 1080 |
| attttttaaa cagacaaatc actctaagca aattacattt gagcagggtg tcatgtttta | 1140 |
| tgttaattca gagaataaga tactatgtct gtcaatatgt gcatgtgtga gagggagaga | 1200 |
| gcctgagtct gtgtgtgtac atgaggattt ttatatagga atgtagacac atatataaag | 1260 |
| aggctttgtc tttatatatt tgtgtataga tcaaagcaca caccctctct catataattg | 1320 |
| gatatttcca agaattgaaa acccatgtga agcattatag atagttttaa atttaaccca | 1380 |
| ctggagtttt cttgaaatac cacttctttt atattatata aaactaaaaa cacgactgtt | 1440 |
| acctttttgtg tgaaccaaag gatacttcag atctcagagc tgccaattat ggggtactaa | 1500 |
| aggtttttaa gacatccagt tctcccgaat ttgggattgc ctctttttct tgaaatctct | 1560 |
| ggagtagtaa tttttttccc cctttttga aggcagtacc ttaacttcat atgcctctga | 1620 |
| ctgccataag ctttttttgat tctgggataa cataactcca gaaaagacaa tgaatgtgta | 1680 |
| atttgggccg atatttcact gttttaaatt ctgtgtttaa ttgtaaaatt agatgcctat | 1740 |
| taagagaaat gaaggggagg atcatcttag tggcttgttt tcagtagtat tttaatatca | 1800 |
| gcttcttgta acctttttcca tgttgtgagg gttgtaaggg attgtgtggc aacagcagct | 1860 |
| tcccttggct aactcaatct tctacccatt gcttagagca gggagccctc cttatttact | 1920 |

```
actgaagacc ttagagaact ccaattgttt ggcatatatt tttggtggtg gttttttattc    1980 ctcctggaga gttatctaat ttgtttctaa aacaaacaag cagcaaagaa atgaattaaa    2040 tactgggggtt gagaattaaa attaagtgga tgttcacagt tgcccaatat atatgacctg   2100
caaatgatac gaaaaagtgc agcatttagt ggcagttaac aagagtgaca agcctggggc    2160
agaggtacca aacctctccc accagagagc tagaagtatt ttatacagta actttgatct    2220
tatggaagtg accttcaatg cttattctga agtaacctat atggtggata caggatgaac    2280
attcagtgcc agggagaatc ttctcaggtt ggttctcgtt agagtgataa actggctagg    2340
ggccatagta ttggtcctgt taggtttcgg tcatggaaaa aaaaattatt ttggggtcat    2400
cctggctcta gatgttatgg gcaaatttct gaaacatctg caagaaggta ccagttaatt    2460
atagtgctta atattgggaa taagattaag cattataatt ataatgtatg ggcctgttgg    2520
tgtaagctca gataattaaa taaaaatagc atgactcaaa tgagacatat tctgctgaac    2580
agtttctact tcctctcccg cctgtcctgt catgggagac gtgtatagtt gctgctgttt    2640
cagcaaacca ccataagacg aaaatgcctc aggttgggtt gccagtcctt tacaactcag    2700
cttgaatttc acaacagtga ttgtgagaat ctgcgtggta tacactgaaa tatcggtgtg    2760
ctgtgatgca aagcttacct ttgacgatat tgaatgtgat atagctgtag agaagtactt    2820
ccttgcctta tgtgaggatt tcaaacttat ttaaattatg tagacaaatc aaagtggcat    2880
tgcttaattt ttagcaggca taataagcaa gttaacagta aaatgcaaaa catgataagc    2940
gttgctcaat ttttagcagg tataataagc aggttaacag taaaaatgca aaacatgata    3000
gataagtcac tttgaaaatt caaaccaaag ttccttcacc ttatggaaat aggaaattat    3060
ggacttcaaa attggacact tcctgtttac aaaaagaaat tcagagctaa aatcatggta    3120
aaaaaaaata gaaacacttg agaactatgg tctttatggg tgcaatttga aatccttttc    3180
atcatcttac cagactaaac taagagcaca taccaaacct atcttatggt tgaaagttgg    3240
ggtttatttt ttatatgaga atattatcac tattacataa catactcagg acaaagaact    3300
ttgctcaggg aacataccat gtaatatttt tgttgtttct ttacagacta gtctacagtc    3360
ctgcttactc aaaacaaacc aaataactta tacctttata taagtattat gtactgatga    3420
tagtaactac ctctgagttt gacacagatc aaaattttg aatatcagat atcagttatc    3480 ctattttat ttcatgtgaa aactcctcta aagcagattc cctcaactct gtgcatatgt    3540
gaatatcact gatgtgaaca cattgttcat ttacataggt aaaatattac tctgttaca    3600 gcaaaggct acctcatagt tgatacatag cacacctgta tgtatgctgt tccagcctta    3660
caggtggctg ataattctct ggtacagaac ctttttatct gtattataaa tagcaattca    3720
caactgcatg tttctgacaa acacttgtga ataatgaagc atctcgtttt agttagcaaa    3780
gtctccaaac atttccttaa aataatcatg tattttagtttt aaagaattat gggcactgtt    3840
caacttaagc aaaacagaac acggaagcag tcttagaagc accactttgc ccagaggtgg    3900
aggttggaag gggtagcagg gagaggggtt ggtgtatgca ggtattcatg ctaggcaaag    3960
agtttaaaag acgccaatgt ccttcattta ctgtctgtgc tgccctgaag ccaagcgtat    4020
tgcagcatta tagccccagg cacataacta actagcactg gcttgccaag gaatgaacat    4080
gcaatgccat tactagctat tgagggaaaa gggtctgtgt gaagcatcac tttgcaggga    4140
ttactaatgg tgggggcagca ggtctgtgaa ttaagttatc tcttgacctc accctcatgt    4200
caacacaaat gtaattccta aacaagatgc attgccagtc tcttagccct gtaagctgat    4260 ctttttgctac atggcagact ataatgaaaa cattttata cttgggtttc tagtcttcac    4320
```

-continued

```
tagaaggcct tggatgtatt tttgcagttg aaagatttag aaagattttt acctgcttat    4380
aacttggaag tttagagtgc aatgtaagaa aaaagatcaa gaaatgtcat gttattagca    4440
tcagtccacc tccaatattg ccgatacttt ttttattctg gctcagtttt attttgcacc    4500
agtgcggccc caagttactg ctggttgtat ttagtttgtg aataggagcc cataagtgtt    4560
aatagacttt gtaacattca ctataagatg aattatacag gacatgggaa atctcattaa    4620
gtcttaaagt taatttaaat taatttatct gttttctcta agaaatgttt atcataaaat    4680
atatatgtgt atttcccctt tggttataaa atttgggaaa gtatgtacaa gtgcagctgc    4740
actgacttta attttctaga tgtcttaatg agatttattt gttttagaga agaacatctt    4800
gttaaaagca tcaaactctg tcttacatag ctgtcaacag cctctttaag atgtggtggt    4860
tgtatgatct gtgtcttaat tgttcagtta gagtgagaag ttgacctatg attcattttt    4920 aaatttata tttggaacaa agctgcaagt tatggtaaag tactgtactg tgagaagtat    4980
tatgatattt aatgcatctg tggcttaaca cttgtgagag ttaccagctt gaaaatgatg    5040
gtgttgacta cctcttgaat cacatctatc aaccactggc acctaccacc aagctggctt    5100
caattagtat gtgttgcttt ttggtattaa caactaaccg tactagagac caaagtgaac    5160
cctgattttt atatgtcttt aataatggtg ttttatctag tgttttaaa ttatcctgtg    5220 tagtatttag attacctcat tgtccatttt gactcatgtt gtttacaagt gaaaataaaa    5280
acacttgaac tgtatgtttt taaaagacaa aaaggggta gatgtttgga atgcgtttca    5340
ctcgcatgca gtcatctgga gggactgaag cactgtttgc ctttctgtac actctggggtt   5400 ttatattctc atttcatgcc taatgtctta ttctgtcaat tatggatatg ttgaggttta    5460
aaaaaattac ttgattaaaa ataaaacata taacgttggc attt                      5504
```

<210> SEQ ID NO 30
<211> LENGTH: 250
<212> TYPE: PRT
<213> ORGANISM: Homo sapiens

<400> SEQUENCE: 30

```
Met Ala Glu Gly Gly Ala Ser Lys Gly Gly Glu Glu Pro Gly Lys
1               5                   10                  15

Leu Pro Glu Pro Ala Glu Glu Ser Gln Val Leu Arg Gly Thr Gly
                20                  25                  30

His Cys Lys Trp Phe Asn Val Arg Met Gly Phe Gly Phe Ile Ser Met
            35                  40                  45

Ile Asn Arg Glu Gly Ser Pro Leu Asp Ile Pro Val Asp Val Phe Val
    50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg
            100                 105                 110

Arg Pro Lys Gly Lys Thr Leu Gln Lys Arg Lys Pro Lys Gly Asp Arg
        115                 120                 125

Cys Tyr Asn Cys Gly Gly Leu Asp His His Ala Lys Glu Cys Ser Leu
    130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Pro Ala Ser Ser
```

```
                        165                 170                 175
Gln Gly Arg Gln Glu Ala Glu Ser Gln Pro Cys Thr Ser Thr Leu Pro
                180                 185                 190

Arg Glu Val Gly Gly Gly His Gly Cys Thr Ser Pro Pro Phe Pro Gln
            195                 200                 205

Glu Ala Arg Ala Glu Ile Ser Glu Arg Ser Gly Arg Ser Pro Gln Glu
        210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 31
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Cys Cys His Cys
1

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Gly Gly Gly Cys
1               5
```

METHODS TO REGULATE MIRNA PROCESSING BY TARGETING LIN-28

CROSS REFERENCE TO RELATED APPLICATIONS

This application is a 371 National Phase Entry Application of co-pending International Application PCT/US2008/079175 filed Oct. 8, 2008, which designated the U.S., and claims the benefit under 35 U.S. 119(e) of U.S. Provisional Patent Application Ser. No. 60/978,610 filed on Oct. 9, 2007, and U.S. Provisional Patent Application Ser. No. 61/029,718 filed Feb. 19, 2008, the contents of which are incorporated herein by reference in their entirety.

GOVERNMENT SUPPORT

This invention was made with Government support under the NIH Director's Pioneer Award of the NIH Roadmap for Medical Research (Grant No DP-1 OD000256), awarded by the National Institutes for Health (NIH). The Government of the United States has certain rights in the invention.

FIELD OF THE INVENTION

The present invention relates generally to methods and compositions to regulate microRNA (miRNA) biogenesis, in particular the regulation of the processing of pri-miRNA to mature miRNA by Lin-28 or variants thereof. In particular, the present invention relates to methods and compositions comprising an agent which inhibits Lin-28 activity and/or expression to increase the processing of pri-mRNA to mature miRNA. More specifically, the present invention relates to the regulation of the processing of the let-7 miRNA family from pri-miRNA to mature miRNA by Lin-28. One aspect of the invention is directed to treating and/or preventing cancer in a subject by administering agent what inhibit Lin-28 to a subject, preferably a human subject.

BACKGROUND OF THE INVENTION

MicroRNAs (miRNAs) constitute a large family of short, non-protein-coding RNAs that function as negative gene regulators by post-transcriptionally repressing gene expression. MicroRNAs have been implicated in critical developmental roles, and dysregulation of miRNA expression has been observed in human malignancies. Recent evidence has shown that miRNA mutations or mis-expression correlate with various human cancers and indicates that miRNAs can function as tumor suppressors and oncogenes. miRNAs have been shown to repress the expression of important cancer-related genes and might prove useful in the diagnosis and treatment of cancer.

Mature miRNAs are produced from long primary miRNA transcripts (pri-miRNAs) through sequential cleavages by the Microprocessor and Dicer complexes, to release pre-miRNA and mature miRNA species, respectively.

Recently, it has been reported that certain pri-miRNAs are readily detectable in embryonic stem (ES) cells, embryonic carcinoma (EC) cells, and primary tumors while the corresponding mature species are present only at exceedingly low levels. This suggests a post-transcriptional block in miRNA biogenesis, the mechanism of which has remained elusive.

Post-transcriptional control of miRNA expression has been reported to occur in a tissue-specific[6] and developmentally regulated fashion[5,7,8]. The processing of several pri-miRNAs is blocked in developmentally primitive states, with activation of processing occurring only as development proceeds. In ES and EC cells, this Drosha processing block is most dramatic for members of the let-7 family of miRNAs.

Accumulating evidence suggests that many cancers are maintained in a hierarchical organization of rare, slowly dividing tumor-initiating cells, rapidly dividing amplifying cells (precursor cells) and differentiated tumor cells. Tumor-initiating (also termed cancer stem) cells have been identified in hematologic, brain, breast, prostate and colon cancers. Stem cells, which are self-renewing and can differentiate into heterogeneous cell populations, are highly tumorigenic. Tumor-initiating cells are thought not only to be the source of the tumor, but may also to be responsible for tumor progression, metastasis, resistance to cancer therapy and subsequent tumor recurrence.

In some organisms, miRNAs are also known to play a role in maintaining stemness of embryonic stem (ES) cells, because ES cells deficient in miRNA processing genes cannot be maintained. Previous studies have shown an overall reduction in miRNA expression in embryonic or tissue stem cells and changes in specific miRNAs have been associated with self-renewal and differentiation of ES cells. Moreover, miRNA expression profiling has been shown to be useful for characterizing the stage, subtype and prognosis of some cancers[18,23,24]

Based on the importance of miRNA in the regulation of cancers, and their potential contribution to sternness of stem cells, they play an important role in the source of the tumor, tumor progression, metastasis, resistance to cancer therapy and subsequent tumor recurrence, a method for reducing the occurrence of cancer stem cells and a method of treating cancer by preventing the differentiation of stem cells into cancer cells in patients is highly desirable.

SUMMARY

The present invention relates to methods to regulate miRNA biogenesis. In particular, one embodiment of the present invention relates to methods to inhibit the expression and/or activity of Lin-28 or its homologue Lin-28B to prevent Lin-28/Lin-28B mediated inhibition of miRNA processing of pri-miRNA to mature miRNA.

In some embodiments, the methods relate to agents which inhibit the expression and/or activity of Lin-28. Accordingly, some embodiments of the present invention provides methods to inhibit Lin-28 and/or Lin-28B to increase of miRNA biogenesis. Such embodiments are desirable to increase the level of miRNAs in the cell, such as for example, to increase the level of a tumor suppressor miRNAs in a cell. Exemplary tumor suppressor miRNAs are for example, but not limited to let-7 family miRNA molecules.

Accordingly, other aspect of the present invention provides methods for the treatment and/or prevention of cancer, by administering to a subject a pharmaceutical composition comprising agents which inhibit the expression and/or activity of Lin-28 or Lin-28B. In some embodiments, the subjects are identified to have, or be at increased risk of developing cancer. In some embodiments, the subjects are identified to have increased levels of Lin-28 and/or Lin-28B as compared to a reference level of Lin-28. In further embodiments, the subjects are identified to have decreased levels of tumor suppressor miRNA molecules, such as for example, but not limited to let-7 family members as compared to a reference levels of such tumor suppressor miRNA molecule.

In alternative embodiments, the methods relate to agents which activate or increase the expression and/or activity of Lin-28. Accordingly, some embodiments of the present invention provides methods to activate the expression or activity of Lin-28 and/or Lin-28B to decrease miRNA biogenesis. Such embodiments are desirable to decrease the level of miRNAs in the cell, for example to decrease the level of oncogenic miRNA molecules in a cell, i.e. miRNA molecules which function as oncogenes (also referred to in the art as "oncoimers" or "oncomiR"). Exemplary oncogenic miRNAs are, for example, but are not limited to miR-21, BIC/miR-155, and mir-17-92 (oncomiR-1). Accordingly, in some embodiments the present invention provides methods for the treatment and/or prevention of cancer by administering to a subject a pharmaceutical composition comprising agents which activate the expression and/or activity of Lin-28. In some embodiments, the subjects are identified to have, or be at increased risk of developing cancer. In some embodiments, the subjects are identified to have increased levels of oncogenic miRNA molecules, such as, but not limited to miR-21, BIC/miR-155, and mir-17-92 as compared to a reference level of the comparable oncogenic miRNA.

The inventors have also discovered the expression of Lin-28 and/or Lin-28B in a cell identifies a cell in a more primitive state, for example a precursor or stem-cell like state. Accordingly, another embodiment of the present invention relates to methods to activate the expression and/or activity of Lin-28 and/or Lin-28B to increase Lin-28 and/or Lin-28B mediated inhibition of miRNA processing of pri-miRNA to mature miRNA. In some embodiments, the present invention relates to methods and compositions to increase the expression and/or activation of Lin-28 and/or Lin-28B in a cell to promote the processing of miR, such as to promote the processing of pri-miRNA to mature miRNA and in some instance to trigger the cell to become a precursor or stem-cell like state, for example to trigger the cell to re-enter a primitive cell state, for example to de-differentiate to become a precursor or stem-cell like cell.

One aspect of the present invention relates to a method of treating or preventing a cancer in a subject comprising administering to a subject a pharmaceutical composition comprising an effective amount of at least one agent that inhibits the activity and/or expression of Lin-28. In some embodiments, the subject is identified to have, or be at risk of an increase in the level of expression and/or activity of Lin-28 and/or Lin-28B in a biological sample as compared to a reference level. In alternative embodiments, the subject is identified to have, or be at risk of a reduction of the level or expression and/or activity, or loss of expression of a tumor suppressor miRNA in a biological sample as compared to a reference level. In some embodiments, a tumor suppressor miRNA is a member of the let-7 miRNA family, or selected from the group consisting of miR-15a, miR-16-1, miR-143 or miR-145.

In some embodiments, the methods as disclosed herein are useful for the treatment or prevention of cancers such as, but not limited to breast cancer, lung cancer, head and neck cancer, bladder cancer, stomach cancer, cancer of the nervous system, bone cancer, bone marrow cancer, brain cancer, colon cancer, colorectal cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, B-cell chronic lymphcylic leukemia, B-cell lymphoma, osteosarcomas, thyroid cancer, prostate cancer, colon cancer, prostate cancer, skin cancer, stomach cancer, testis cancer, tongue cancer, or uterine cancer. In particular embodiments, wherein the cancer is breast cancer or lung cancer. In some embodiments, the cancer is a pre-cancer, malignant cancer, therapy resistant cancer or a cancer which comprises cancer stem cells.

In some embodiments, agents useful in the methods and compositions as disclosed herein for inhibition of Lin-28 and/or Lin-28B expression (protein or gene expression) or activity include for example, but are not limited to, a small molecule, nucleic acid, nucleic acid analogue, aptamer, ribosome, peptide, protein, antibody, or variants and fragments thereof. In some embodiments, an agent is an antibody, for example, a recombinant antibody, humanized antibody, chimeric antibody, modified antibody, monoclonal antibody, polyclonal antibody, miniantibody, dimeric miniantibody, minibody, diabody or tribody or variants, analogues or modified versions thereof. In other embodiments, agents useful for inhibition of Lin-28 and/or Lin-28B expression are nucleic acid molecules, such as DNA, RNA, nucleic acid analogue, peptide nucleic acid (PNA), pseudo-complementary PNA (pcPNA), locked nucleic acid (LNA), antagomir or analogue thereof. In particular embodiments, an agent can be a RNA molecule, for example a small inhibitory RNA (RNAi) such as siRNA, microRNA, shRNA, miRNA molecules and analogues and homologues and variants thereof. In some embodiments, an RNAi molecules useful in the methods as disclosed herein are siRNA molecules to Lin-28 which correspond to the nucleic acid sequences SEQ ID NO:7, 8 or 9. In alternative embodiment, an agent can be a nucleic acid inhibitor agent or antagomir which binds to the let-7 miRNA target site in the 3'UTR of the Lin-28 gene. In alternative embodiments, an agent can be a miRNA such as Lin4 or let-7 or variants thereof.

An alternative embodiment of the present invention relates to methods to treating or preventing a cancer in a subject, comprising administering to a subject a pharmaceutical composition comprising an effective amount of at least one agent that activates the activity and/or expression of Lin-28, for example where a subject is identified to have, or be at risk of a decrease in the level of expression and/or activity, or loss of expression of Lin-28 and/or Lin-28B in a biological sample, for example a biological sample comprising cancer cells, as compared to a reference level. In alternative embodiments, a subject amenable to administration of agents which activate Lin-28 are subjects identified to have, or be at risk of an increase in the level or expression and/or activity expression of an oncogenic miRNA in a biological sample as compared to a reference level, for example subjects identified to have an increase in oncogenic miRNA such as miR-21 or BIC/MiR-155.

In some embodiments, a pharmaceutical composition comprising at least one agent which inhibits or activates Lin-28 and/or Lin-28B are administered intravenous, intradermal, intramuscular, intraarterial, intralesional, percutaneous, subcutaneous, or by aerosol. In some embodiments, a subject can also administered one or more additional therapies simultaneously, before or after administration of agents which inhibit or activate Lin-28, for example subjects are administered additional therapies such as surgery, chemotherapy, radiotherapy, thermotherapy, immunotherapy, hormone therapy or laser therapy. For example, a pharmaceutical composition as disclosed herein comprising at least one agent which inhibits the activity or expression of Lin-28 and/or Lin-28B can be administered concurrently with, or before, or after, the delivery of a let-7 miRNA, for example were a let-7 miRNA is being used as a therapeutic strategy for cancer in a subject.

In some embodiments, a subject amenable to treatment or prevention of cancer is a mammal, for example a human.

Another aspect of the present invention relates to the use of an agent which inhibits the expression and/or activity of Lin-28 and/or Lin-28B protein for the preparation of a medicament for the treatment and/or prevention of a cancer or malignancy, wherein the cancer or malignancy is characterized by an increase in the expression or activity of the Lin-28 and/or Lin-28B protein, or a reduction in level of, or loss of at least one tumor suppressor miRNA in the cancer, for example, a loss of a tumor suppressor miRNA such as a member of the let-7 miRNA family.

Another aspect of the present invention relates to identifying a subject at risk of developing cancer, the method comprising obtaining a biological sample from a subject and measuring the level of expression and/or activity of Lin-28 and/or Lin-28B in the biological sample, wherein if the level is above the level in a reference sample, the subject is identified as being likely to be at risk of developing, or have cancer. In some embodiments, the reference level of Lin-28 and/or Lin-28B is the level of expression or activity of Lin-28 and/or Lin-28B in a normal biological sample, for example a biological sample comprising normal non-cancer cells. Alternatively, the reference sample can be from the same subject at an earlier timepoint.

In a related embodiment, methods disclosed herein provide a method to treat cancer, the methods comprising obtaining a biological sample from a subject and measuring the level of expression and/or activity of Lin-28 and/or Lin-28B in the biological sample, wherein a clinician then reviews the result and if the results indicate the level of Lin-28 and/or Lin-28B is above the level of Lin-28 and/or Lin-28B in a reference sample, then the clinician directs the subject to be treated with a pharmaceutical composition comprising an inhibitor agent of the expression and/or activity of Lin-28.

Another aspect of the present invention relates to a method to identify subject having an increased likelihood of developing or having cancer. In some embodiments, the method comprises measuring the level of the expression or activity of Lin-28 in a biological sample obtained from the subject, for example measuring protein expression or gene expression, where the level is compared to a reference level and if the expression or activity level of Lin-28 is higher than the expression or activity of a reference level, the subject is identified as having an increased likelihood of developing cancer. In some embodiments, the cancer is selected from a group consisting of; gastrointestinal cancer, prostate cancer, ovarian cancer, breast cancer, squamous cell carcinomas (SCC), head and neck cancer, lung cancer, non-small cell lung cancer, cancer of the nervous system, brain cancer, bone-marrow cancer, bone cancer, kidney cancer, retina cancer, skin cancer, bladder cancer, colon cancer, esophageal cancer, testicular cancer, leukemia, lymphoma, melanoma, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer. In other embodiments, the cancer is breast cancer is a triple-negative subtype breast cancer; or a cancer which lacks the expression of estrogen receptor (ER), the progesterone receptor (PR) and lacks Her-2 expression.

In some embodiments, the biological sample is serum plasma, blood or tissue sample, for example, wherein the biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample or primary ascite sample. In alternative embodiments, the biological sample includes, for example blood, plasma, serum, urine, spinal fluid, plural fluid, nipple aspirates, lymph fluid, external secretions of the skin, respiratory, internal and genitourinary tracts, bile, tears, sweat, saliva, organs, milk cells and primary ascite cells, biopsy tissue sample, a cancer biopsy tissue sample, an in vitro or ex vivo cultivated biopsy tissue sample.

In some embodiments, measuring the level of the expression or activity of Lin-28 and/or Lin-28B in a biological sample includes, for example measuring the level of gene transcript expression or mRNA expression of Lin-28, and/or measuring is measuring the level of protein expression of Lin-28 and/or Lin-28B and/or measuring the level of protein activity of Lin-28.

In some embodiments, protein expression can be measured by a method selected from the group consisting of; immunoblot analysis, immunohistochemical analysis; ELISA, isoform-specific chemical or enzymatic cleavage, protein array or mass spectrometry. In some embodiments, protein expression can be measured by contacting the biological sample with at least one protein binding agent selected from the group consisting of; antibodies; recombinant antibodies, chimeric antibodies, tribodies, midibodies, protein-binding agents, small molecule, recombinant protein, peptides, aptamers, avimers and derivatives or fragments thereof.

In some embodiments, gene expression can be measured by methods selected from the group comprising; reverse-transcription polymerase chain reaction (RT-PCR) or by quantitative RT-PCR (QRT-PCR) reaction.

Another aspect of the present invention related to a method for preventing the development of cancer in a subject, the method comprising assessing the risk of a subject to develop cancer by identifying if a subject has an increased likelihood of developing or having cancer by measuring the level of the expression or activity of Lin-28 and/or Lin-28B in a biological sample obtained from the subject, for example measuring protein expression and/or gene expression, where a clinician reviews the results and assesses the level of Lin-28 and/or Lin-28B protein or gene expression as compared to a reference level and if the clinical determines if expression or activity level of Lin-28 and/or Lin-28B is higher than the expression or activity of a reference level, the subject is identified as having an increased likelihood of developing cancer, the clinician then directs a subject to be treated with an appropriate anti-cancer therapy if the subject is at risk of developing cancer.

Another aspect of the present invention relates to a method for treating cancer in a subject comprising measuring the level of the expression or activity of Lin-28 and/or Lin-28B in a biological sample obtained from the subject, wherein a clinician reviews the results and if the expression or activity level of Lin-28 and/or Lin-28B is higher than the expression or activity of a reference level, the clinician directs the subject to be treated with an anti-cancer therapy and/or a pharmaceutical composition comprising an effective amount of at least one agent that inhibits the activity and/or expression of Lin-28.

extract (right) prior to processing reaction with Flag-Drosha immunoprecipitate, as described in herein in the Methods section of the Examples.

FIG. 2 shows recombinant Lin-28 protein selectively inhibits pri-miRNA processing in vitro. a, colloidal blue staining of bacterially expressed His-tagged recombinant Lin-28 (rLin-28) with BSA standard used to estimate rLin-28 protein concentration. b, in vitro pri-miRNA processing reaction using rLin-28 and either pri-let-7g (lanes 1-5) or pri-miR-15a/16-1 substrates (lanes 6-10). (*) pri-miRNA, (**), pre-miRNA. For both a and b, '1X' corresponds to 500 ng of protein.

FIG. 3 shows ectopic expression of Lin-28 selectively inhibits pri-miRNA processing in vivo. 293T cells were either untransfected (lane 1), co-transfected with pri-miRNA and 4 μg empty vector (lane 2), or co-transfected with pri-miRNA and full-length Lin-28 cDNA (lanes 3-5). Total RNA was collected 2d post-transfection and Northern blotted for miRNA. a, pri-let-7g b and c, pri-15a/16-1. Note that 293T cells contain endogenous miR-15a and miR-16-1 expression.

Figure 4C:
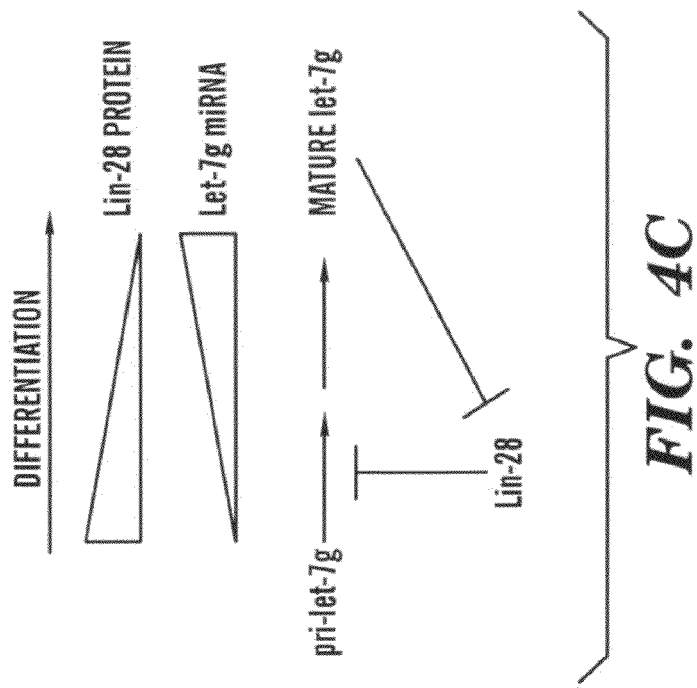

FIG. 4 shows knockdown of Lin-28 relieves the miRNA-processing block. P19 cells were transfected with control (GFPi) or pLKO.1-shRNA hairpins targeting Lin-28. Total RNA was collected 60-hrs post-transfection for analysis. a, quantitative PCR analysis for Lin-28 expression using beta-actin as an internal standard, and normalized to Lin-28 expression with control hairpin. b, Northern blot for let-7g. c, proposed model for Lin-28 action during ES/EC-cell differentiation.

Figures 5A, 5B:
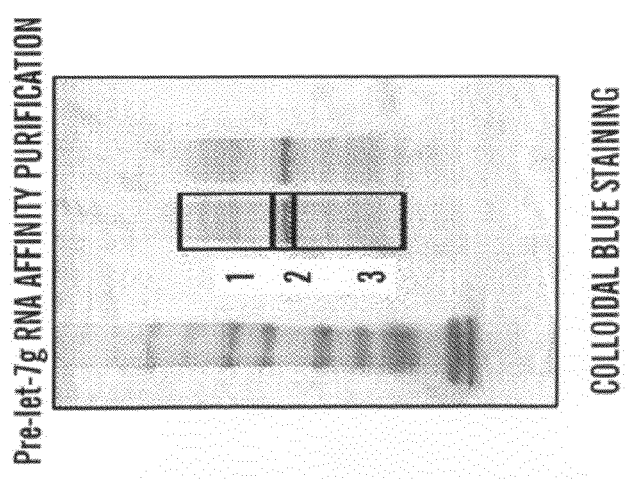

FIG. 5 shows Purification of pre-let-7g associated factors. FIG. 5a shows pre-let-7g was conjugated to agarose beads and used for affinity purification from 30 mg P19 whole cell extract. Eluted proteins were separated by SDS-PAGE and the gel was stained with colloidal blue as shown. Bands in the lane were processed for mass spectroscopic sequencing as the three samples indicated by boxes. FIG. 5b, a partial list of proteins identified by mass spectroscopy in each of the samples. Proteins in bold font were also identified during Flag-affinity purification of Drosha-containing complexes[1].

Figure 6:
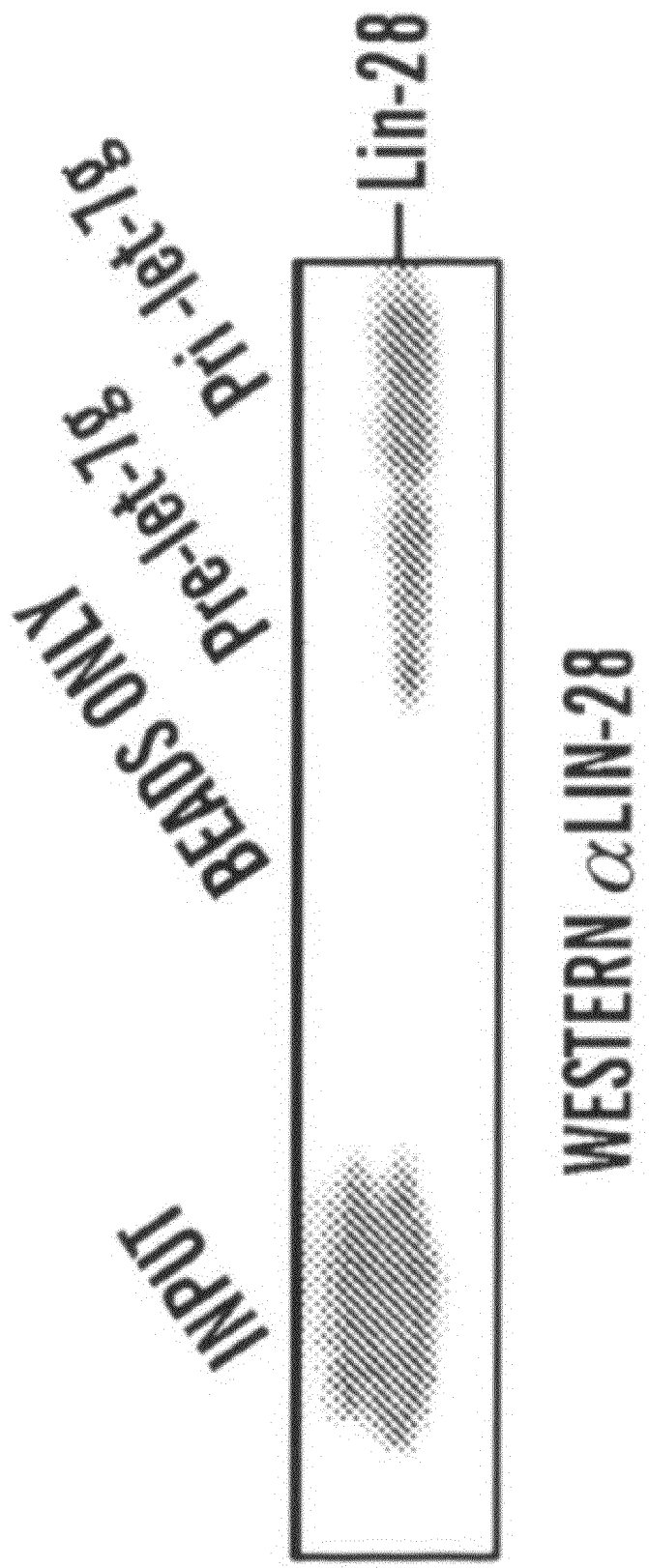

FIG. 6 shows Lin-28 binds pri-let-7g and pre-let-7g in vitro. Pri-let-7g (produced by in vitro transcription) or pre-let-7g (synthetic) was conjugated to agarose beads and used in a co-sedimentation assay from P19 whole cell extract. Eluate was separated by SDS-PAGE and western blot was done with α-Lin-28 antiserum.

FIG. 7 shows post-transcriptional control of pri-let-7g processing. FIG. 7a shows RT-PCR for pri-let-7g transcript (as described in ref. (7) during ES differentiation to embryoid bodies. Actin serves as control. FIG. 7b shows a Northern blot showing post-transcriptional induction of mature let-7g during embryoid body formation 5S rRNA serves as loading control. FIG. 7c shows in vitro pri-miRNA processing reaction using radiolabeled pri-let-7g as substrate. Pri-miRNA was pre-incubated with various amounts of P19 cell extract or mouse embryonic fibroblast (MEF) extract prior to processing reaction with Flag-Drosha immunoprecipitate, as described in Methods. The ratio of pre-miRNA to pri-miRNA was quantitated by densitometry and values were normalized to the Microprocessor only lane. FIG. 7d shows qPCR analysis of gene expression during embryoid body formation of a feeder-free mouse ES line (J1 ES). Top Panel: Pri-let-7g and mature let-7g; Middle Panel: Lin-28; Bottom Panel: pluripotency factors October-4 and Nanog.

FIG. 8 shows Lin-28 Inhibits pri-miRNA processing in vitro. FIG. 8a shows α-Flag-Western to confirm expression of Flag-tagged proteins for use in in vitro assays. FIG. 8b shows in vitro pri-miRNA processing reaction on pri-let-7g (left panel) and pri-let-7a (right panel) substrates in the presence of either Mock, Flag-Lin-28, Flag-hnRNPA1, or Flag-Msi-2 immunoprecipitate. Quantitation was normalized to the Microprocessor-only lane. FIG. 8c shows in vitro pri-miRNA processing reaction on pri-let-7g (left panel) and pri-miR-15a/16-1 (right panel) substrates in the presence of either mock or Flag-Lin-28 immunoprecipitate and competitor tRNA. Quantitation was normalized to the Mock-IP lane. FIG. 8d shows in vitro pri-miRNA processing reaction on pri-let-7g (left panel) and pri-let-7a (right panel) substrates in the presence of rHis-Lin-28. Quantitation was normalized to the Microprocessor-only lane.

FIG. 9 shows Ectopic expression of Lin-28 selectively inhibits pri-miRNA processing in vivo. Each panel in FIG. 9a shows 293T cells which were either untransfected (lane 1), co-transfected with the indicated pri-miRNA and 0.5 μg pCMV-Flag empty vector (lane 2), or co-transfected with the indicated pri-miRNA and 0.5 μg Flag-Lin-28 cDNA (lane 3). Total RNA was collected 40 h post-transfection and Northern blotted for the indicated miRNA. FIG. 9b shows qPCR analysis of pri-let-7g levels for sample in a) (top right panel). FIG. 9c shows mature let-7g levels upon co-transfection of 293T cells with pri-let-7g and either pCMV-Flag, Flag-Lin-28, Flag-hnRNPA1, Flag-hnRNPL, Flag-YBX-1, or Flag-Msi-2 cDNAs, as measured by quantitative PCR. First, the amount of mature let-7g in each sample was calculated relative to untransfected control cells, then Flag-protein co-transfected samples were normalized to the corresponding pCMV-Flag co-transfected samples. FIG. 9d shows qPCR showing changes in levels of endogenous mature miRNAs upon transfection of Flag-Lin-28 in 293T cells. FIG. 9e shows qPCR showing accumulation of endogenous pri-let-7g upon transfection of Flag-Lin-28 in 293T cells. For FIGS. 9c-9e, values are given as average+/−S.E.M. from two or more independent transfections.

FIG. 10 shows Knockdown of Lin-28 relieves the miRNA-processing block. P19 cells were transfected with control hairpin (GFPi), pLKO.1-shRNA hairpins targeting Lin-28, control siRNA (scrambled sequence), or Lin-28 siRNA. Total RNA was collected 60-hrs post-transfection for analysis. FIG. 10a shows quantitative PCR analysis of Lin-28 expression, normalized to Lin-28 expression with control hairpin or control siRNA, for samples in FIG. 10b. FIG. 10b shows Northern blot for mature let-7g. FIG. 10c shows confirmation of Lin-28 knockdown using Lin28-SI2 on samples analyzed in FIG. 10d. Error bars represent S.E.M. with N=3. FIG. 10d shows changes in mature miRNA levels upon knockdown of Lin-28 as analyzed by quantitative PCR. Error bars represent S.E.M. with N=3. FIG. 10e shows levels of pri-let-7g upon knockdown of Lin-28 in P19 cells. Error bars represent S.E.M. with N=3. FIG. 10f shows levels of the pluripotency markers Oct-4 and Nanog in P19 cells transfected with either control siRNA or Lin28-SI2. Error bars represent S.E.M. with N=3.

Figure 11:
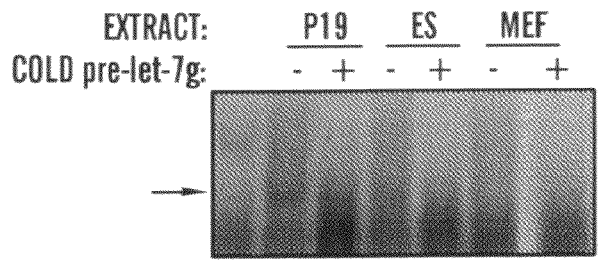

FIG. 11 shows P19 and ES Cells Possess a Unique Band-Shift. Pre-let-7g was used in a Gel-Shift assay with cell extracts from P19 Cells, ES cells, or MEFs. A unique shift (arrow) was observed with P19 and ES cell extract, and was specifically competed away with 100 pmol cold pre-let-7g. This band-shift was not observed using MEF cell extract.

Figure 12A:
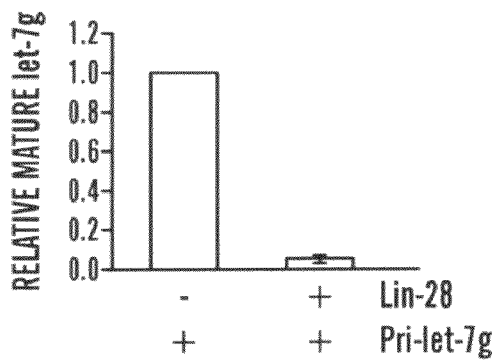
Figure 12B:
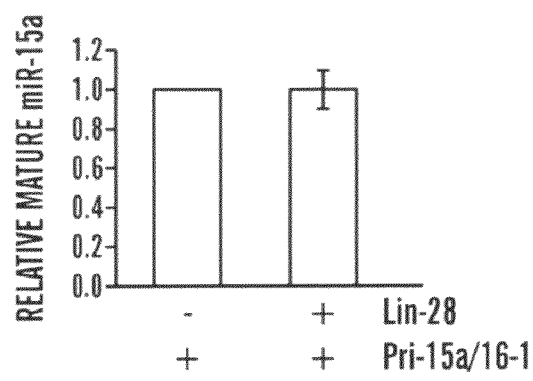

FIG. 12 shows Lin-28 selectively blocks the processing of let-7g. 293T cells were either untransfected or co-transfected with pri-let-7g (12a) or pri-miR-15a/16-1 (12b) and either empty vector (pCMV) or pFlag-Lin-28. RNA was collected at 40 h post-transfection and amount of mature let-7g (12a) or miR-15a (12b) was measured by quantitative PCR. Fold pri-miRNA induction over untransfected 293T cells was first calculated, and values for Lin-28 co-transfected samples were then normalized to values for the corresponding pCMV co-transfected samples. Values are given as average+/−S.E.M. with N=3.

Figure 13:
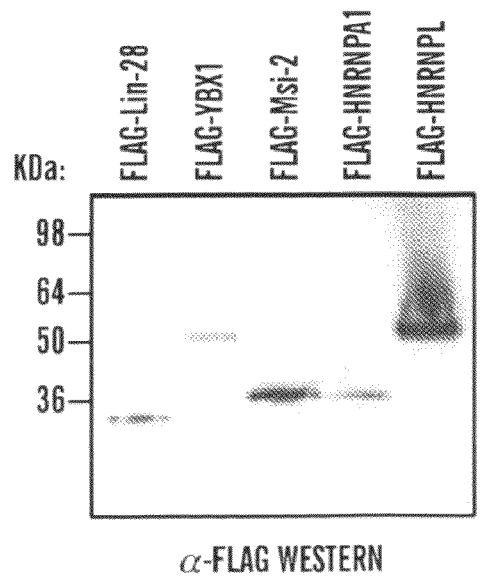

FIG. 13 shows Immunoblot using anti-Flag antibody showing comparable expression of Flag-Lin-28 and Flag-tagged control RNA-binding proteins when expressed in 293T Cells.

Figure 14C:
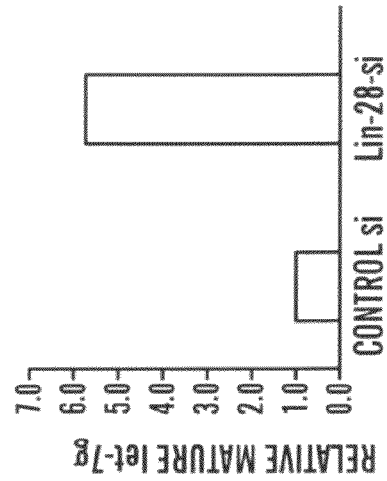
Figure 14A:
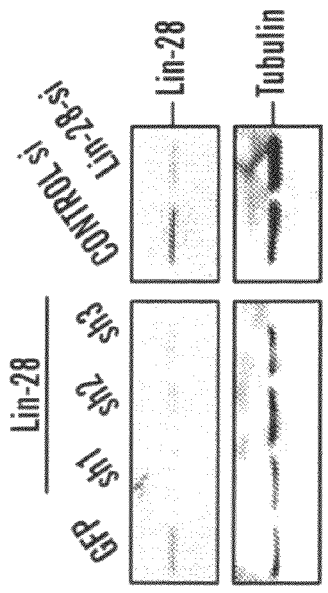
Figure 14B:
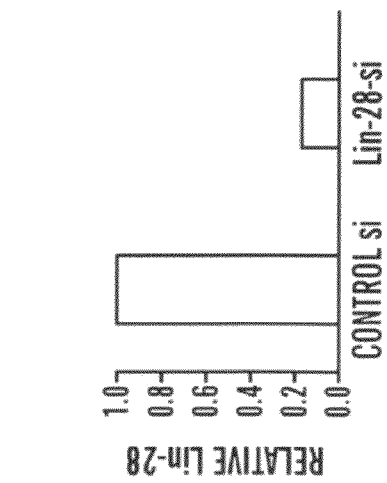

FIG. 14 shows Knockdown of Lin-28 relieves miRNA Processing Block in ES Cells. a, Depletion of Lin-28 protein upon transfection of Lin-28 knockdown constructs into feeder-free J1 ES cells. Immunoblot was performed on whole cell extracts using anti-Lin-28 antibody b, Knockdown of Lin-28 as assessed by qPCR using Lin-28-siRNA in a feeder free V6.5 mouse embryonic stem cell line. c, induction of mature let-7g upon Lin-28 knockdown as measured by qPCR.

Figure 15:
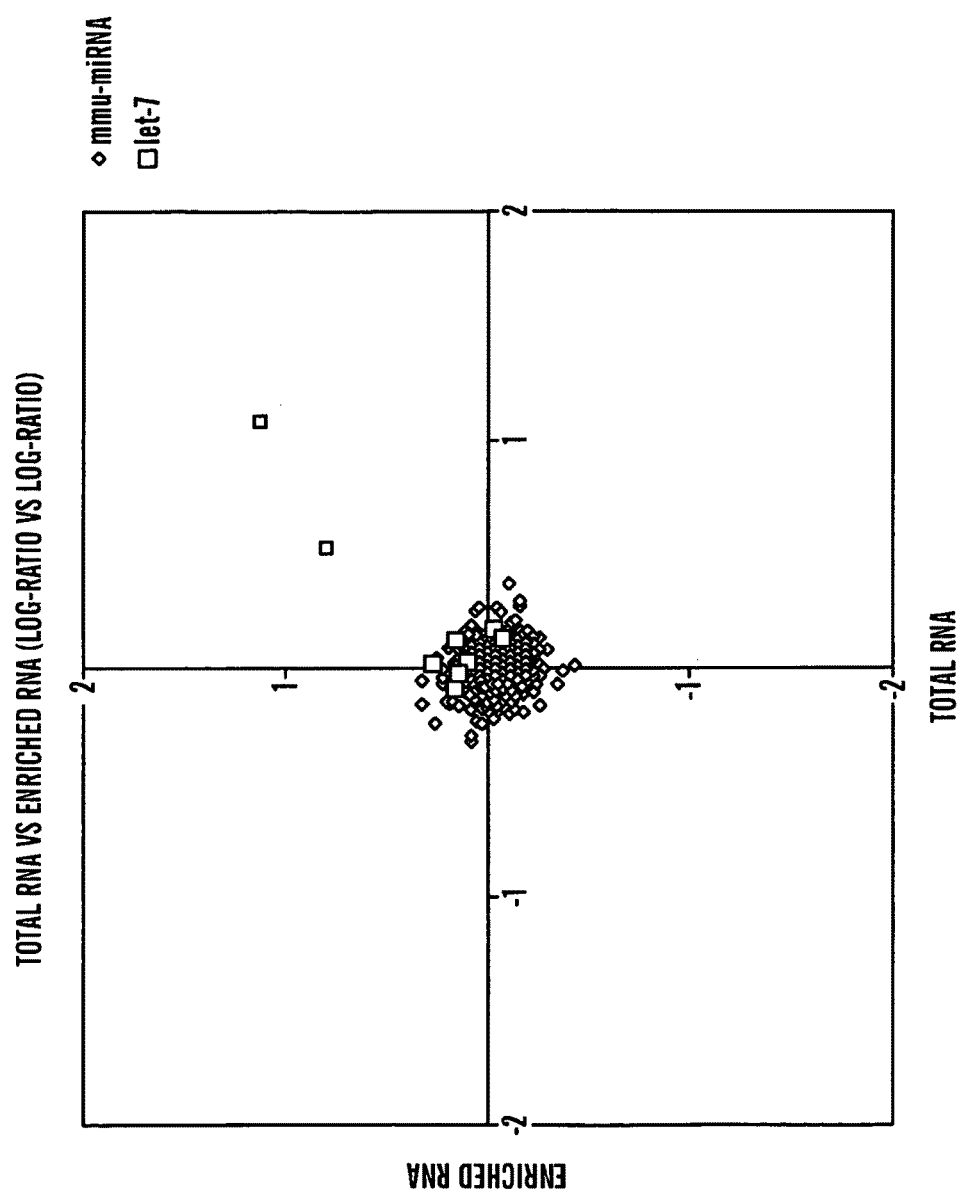

FIG. 15 shows Global miRNA Profiling. Global miRNA profiling was commercially performed (Exiqon) on RNA samples from P19 cells transfected with either control siRNA (scrambled sequence) or Lin-28 siRNA. Both total RNA and small-RNA-enriched fractions were used for analysis. Scatterplot shows ratio of miRNA expression in the Lin-28 siRNA sample condition to the scrambled siRNA control for both total RNA and small-RNA enriched samples. Expression of let-7 miRNAs is shown in pink while all other miRNAs are shown in blue. The data show that let-7a and let-7d are the most differentially regulated following siRNA knock-down of Lin-28. Because of the modest dynamic range of sensitivity for this assay, more subtle degrees of miRNA up-regulation may not be revealed.

Figure 16A:
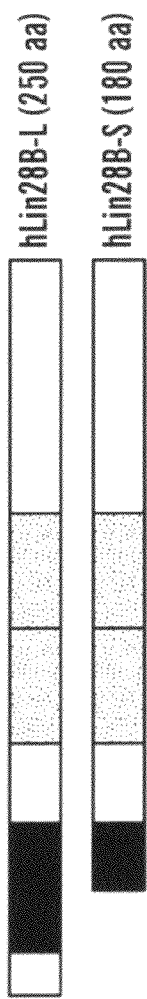
Figure 16C:
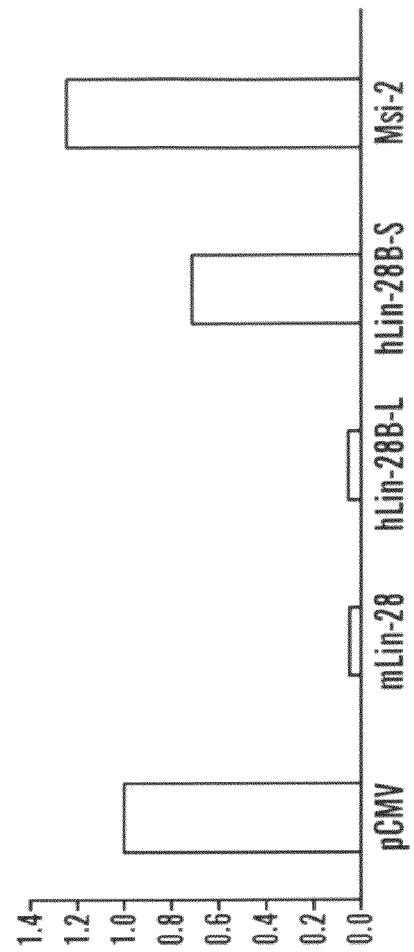
Figure 16B:
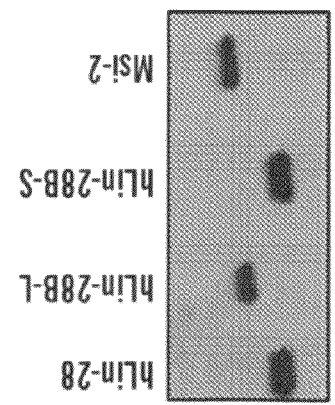

FIG. 16 shows Lin-28B also blocks let-7 Processing. FIG. 16a shows a Schematic of naturally occurring long and short Lin-28B isoforms. The cold-shock domain is shaded in black while the two CCHC motifs are shaded in grey. FIG. 16b shows an Immunoblot using anti-Flag antibody showing comparable expression of Flag-tagged RNA-binding proteins used in c. FIG. 16c shows 293T cells were either untransfected or co-transfected with pri-let-7g and either empty vector (pCMV) or plasmid encoding Flag-tagged Lin-28, Lin-28B-L, Lin-28B-S, or Msi-2. RNA was collected at 40 h post-transfection and amount of mature let-7g was measured by quantitative PCR. Fold pri-miRNA induction over untransfected 293T cells was first calculated, and values for Flag-tagged protein co-transfected samples were then normalized to value for the pCMV co-transfected sample.

FIG. 17 shows Lin28 and Lin28B expression in human tumors. FIG. 17A shows Lin28 and Lin28B expression in non-seminomatous male germ cell tumors as determined by microarray analysis. Lin28 and Lin28B signal is log-2 transformed and normalized to the average of the normal testes samples. T, tumor sample; N, normal testes. FIG. 17B shows immunohistochemical detection of Lin28/Lin28B in embryonal carcinoma tumor tissue. The right panel of FIG. 17B shows strong cytoplasmic immunoreactivity of embryonal carcinoma cells (between arrows), and also shows endodermal epithelial elements of teratoma (arrows) and tumoral stroma are not immunoreactive. The middle panel of FIG. 17B shows a higher magnification of immunoreactive embryonal carcinoma shown in the right panel of 17B showing that adjacent seminiferous tubules are negative (between arrows). The far left panel of 17B shows intratubular germ cell neoplasia strongly immunoreactive for Lin28/Lin28B. FIG. 17C shows Lin28 expression in a panel of 285 ovarian tumors as determined by microarray analysis. Log-2 transformed Lin28 signal was row-normalized. FIG. 17D shows Lin28B expression in a panel of 285 ovarian tumors as determined by microarray analysis. Log-2 transformed Lin28B signal was row-normalized. FIG. 17E shows immunohistochemical analysis of Lin28/Lin28B expression in ovarian tumor tissue. Tissue sections from ovarian carcinoma subtypes (17Ei-17Eiii) or normal ovary (17Eiv-17Evi) were stained with anti-Lin28/Lin28B antibody. 17E(i) shows Papillary Serous Carcinoma, 17E(ii) shows Clear Cell Carcinoma; 17E(iii) shows Endometriod Carcinoma; 17E(iv) shows Normal ovarian medulla, 17E(v) shows Normal ovarian cortex. Arrow, ovarian surface epithelium. 17E(vi) is a no primary antibody control.

FIG. 18 shows Lin28 cooperates with BCR-ABL to transform NIH/3T3 cells. FIG. 18A shows Western blot analysis of extracts from NIH/3T3 cells infected with pBabe.Puro, pBabe.Puro.BCR-ABL, and/or pMSCV.Neo.Lin28, selected with Puromycin and G418. FIG. 18B shows the levels of mature miR species in representative infection determined by quantitative PCR in NIH/3T3 cells infected with pMSCV.Neo or pMSCV.Neo.Lin28, and selected on G418. FIG. 18C shows the colony numbers in semisolid media for 50,000 NIH/3T3 cells infected with pBabe.Puro, pBabe.Puro.BCR-ABL, and/or pMSCV.Neo.Lin28, and selected with Puromycin and G418. Colonies were counted after 21d with five random fields per plate. Results are plotted as average colony number+/−S.E.M., N=3. FIG. 18D shows photomicrographs of representative fields from soft agar assay in the colony number assay shown in FIG. 18C.

FIG. 19 shows that Lin28 cooperates with c-Abl/G2A to transform Ba/F3 cells to factor independence. FIG. 19A shows Western blot analysis of extracts from Ba/F3 cells infected with pBabe.Puro or pBabe.Puro.Lin-28, selected on Puromycin. FIG. 19B shows the level of mature miR species in representative infection determined by quantitative PCR in Ba/F3 cells infected with pBabe.Puro or pBabe.Puro.Lin28, and selected on Puromycin. FIG. 19C shows Western blot analysis of extracts from Ba/F3 cells infected with pBabe.Puro, pEYK.Puro.Abl/G2A, pMSCV.Neo, and pMSCV.Neo.Lin-28, selected on Puromycin and G418, FIG. 19D shows Ba/F3 lines established in (C) were plated in media without IL-3 at 10,000 cells per well. Cells were stained with Trypan blue and counted 3d after plating. FIG. 19E shows Ba/F3 cells expressing Abl/G2A or Abl/G2A+Lin28 were plated at 50,000 cells per well in semisolid medium without IL-3. Colonies were stained with crystal violet and counted 2 weeks after plating. FIG. 19F shows the quantitation of colony number from soft agar assay. Results are plotted as average colony number per well+/−S.E.M., N=3.

FIG. 20 shows that Lin28 enhances transformation of LKR cells. FIG. 20A shows Western blot analysis performed on LKR cells infected with pBabe.Puro or pBabe.Puro.Lin28, and selected on Puromycin. FIG. 20B shows levels of mature miR species in representative infection determined by quantitative PCR of LKR cells infected with pBabe.Puro or pBabe.Puro.Lin28, and selected with Puromycin. FIG. 20C shows Proliferation of LKR cells infected with pBabe.Puro, pBabe.Puro.Lin28, or pMSCV.Neo.let-7g, and selected with Puromycin or G418, plated at 5000 cells per well and assayed over indicated time period. Cell counts are plotted as mean+/−S.E.M., n=3. FIG. 20D shows Representative plate from colony formation assay (n=3) of LKR cells infected with pBabe.Puro or pBabe.Puro.Lin28, selected on Puromycin, and plated at 2000 cells per 10 cm dish. Colonies were stained with crystal violet and counted after 5 d of growth.

FIG. 21 shows Lin28B is required for the growth of H1299 lung adenocarcinoma cells. FIG. 21A(i) shows the signal intensity of Lin28 expression in human cancer cell lines, as determined by microarray analysis. Signal intensity was normalized to HeLa cells, which do not express Lin28. FIG.

Figures 21B, 21C, 21D:
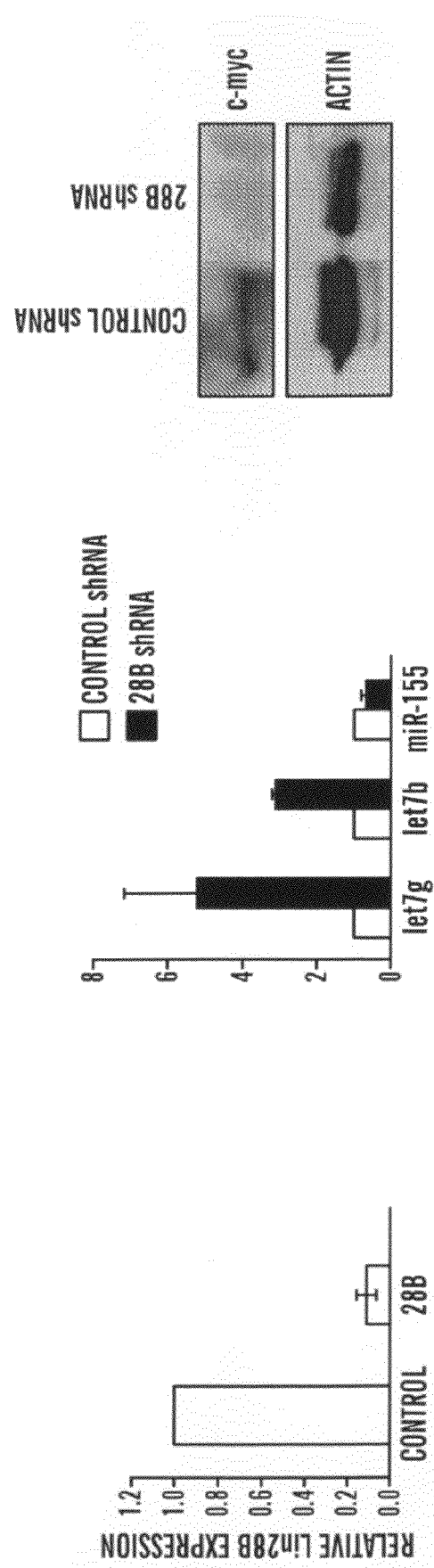
Figure 21F:
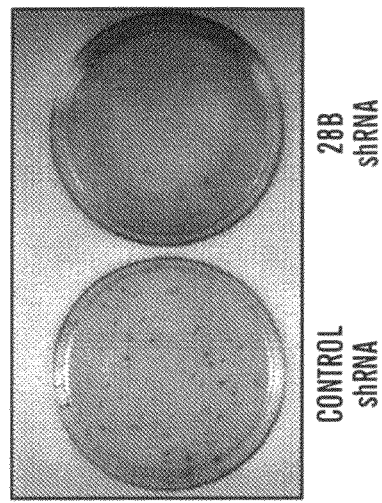
Figure 21H:
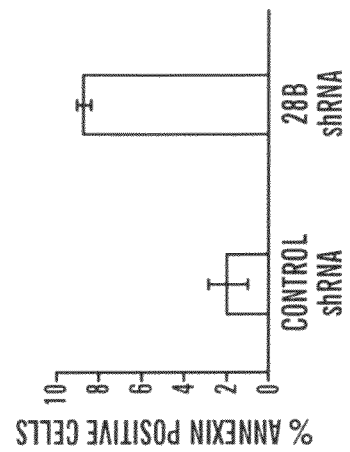
Figure 21E:
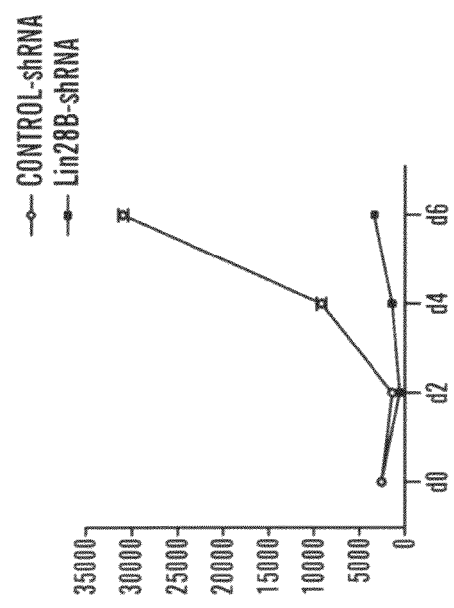
Figure 21G:
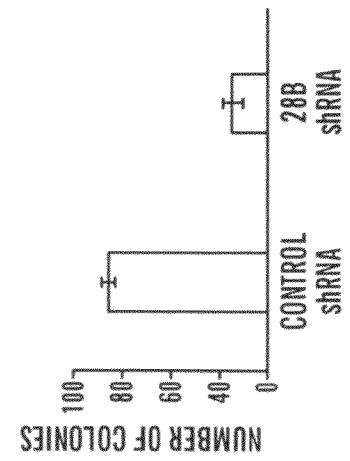

21A(ii) shows the signal intensity of Lin28B expression in human cancer cells, as determined by quantitative PCR. Expression levels were normalized to HeLa cells. FIG. 21B shows Lin28B expression measured by quantitative PCR in H1299 cells infected with pLKO.controlshRNA or pLKO.Lin28BshRNA, and selected on Puromycin. FIG. 21C shows the level of mature miR species in representative infection determined by quantitative PCR of H1299 cells infected with pLKO.controlshRNA or pLKO.Lin28BshRNA, and selected with Puromycin. FIG. 21D shows Western blot analysis on whole cell extracts from H1299 cells infected with pLKO.controlshRNA or pLKO.Lin28BshRNA and selected in Puromycin. FIG. 21E shows the proliferation of H1299 cells infected with pLKO.controlshRNA or pLKO.Lin28BshRNA and seeded at 2500 cells per well. Cells were counted over time and results are plotted as mean+/−S.E.M., n=3. FIG. 21F is a representative image of colony formation of H1299 cells infected with pLKO.controlshRNA or pLKO.Lin28BshRNA, selected on Puromycin, and plated at 2000 cells per 10 cm dish. After 7 d of growth, colonies were stained with crystal violet. FIG. 21G shows the quantitation of colony number from colony forming assay. Results are plotted as average number of colonies per plate+/−S.E.M., N=3. FIG. 21H shows H1299 cells which were infected with pLKO.controlshRNA or pLKO.Lin28BshRNA, stained with Annexin-PE and 7-AAD, and percentage of total Annexin positive cells for each condition was quantitated. Results are plotted as average number of Annexin positive cells+/−S.E.M., N=3.

Figure 22A:
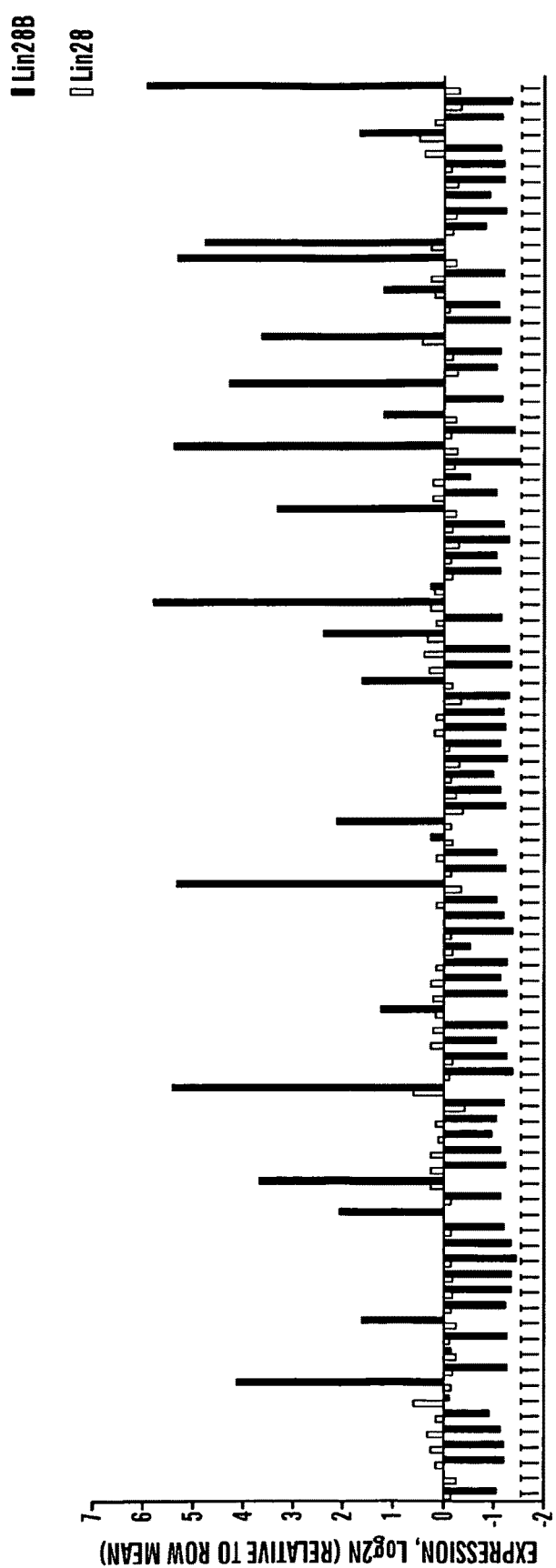
Figure 22B:
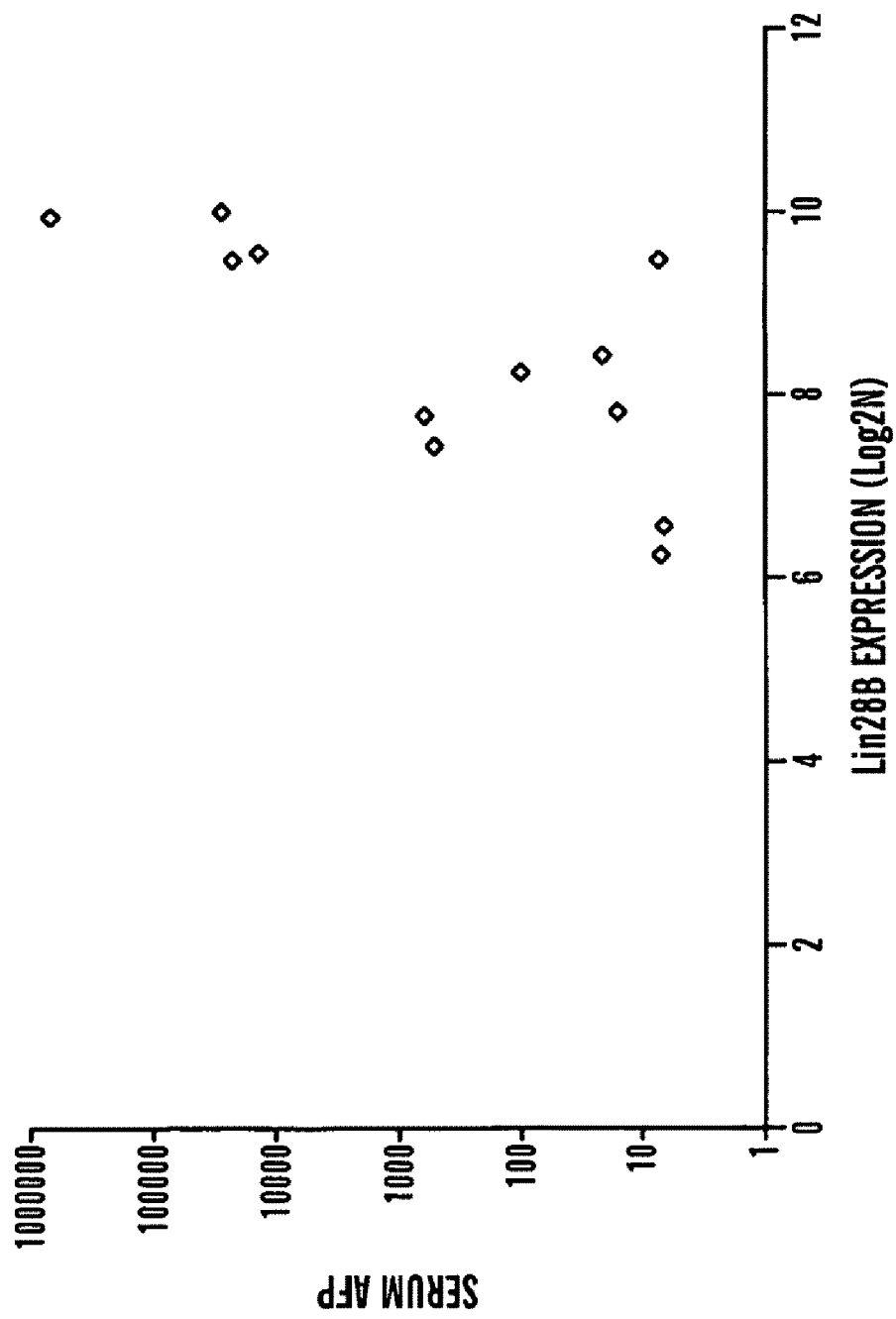
Figure 22C:
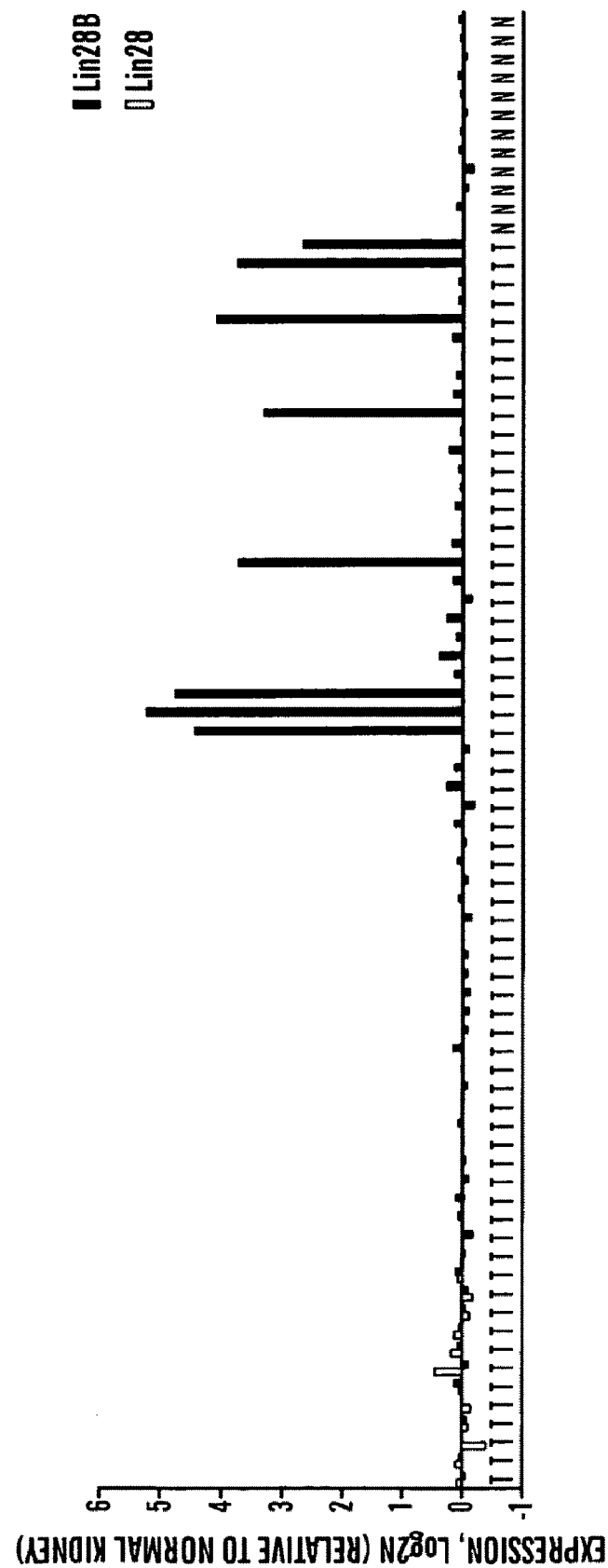

FIG. 22 shows Lin28/Lin28B Expression in Human Primary Tumors. FIG. 22A shows Lin28 and Lin28B expression in human hepatocellular carcinoma samples as determined by microarray analysis. Lin28 and Lin28B signal is log 2 transformed and row-normalized. T, tumor sample. N, normal liver. FIG. 22B shows serum AFP values were plotted against log 2-normalized Lin28B expression values for patients with log 2N signal >6.00. FIG. 22C shows Lin28 and Lin28B expression in human renal tumor samples as determined by microarray analysis. Lin28 and Lin28B signal is log 2 transformed and normalized to normal kidney. T, tumor sample; N, normal kidney.

Figure 23A:
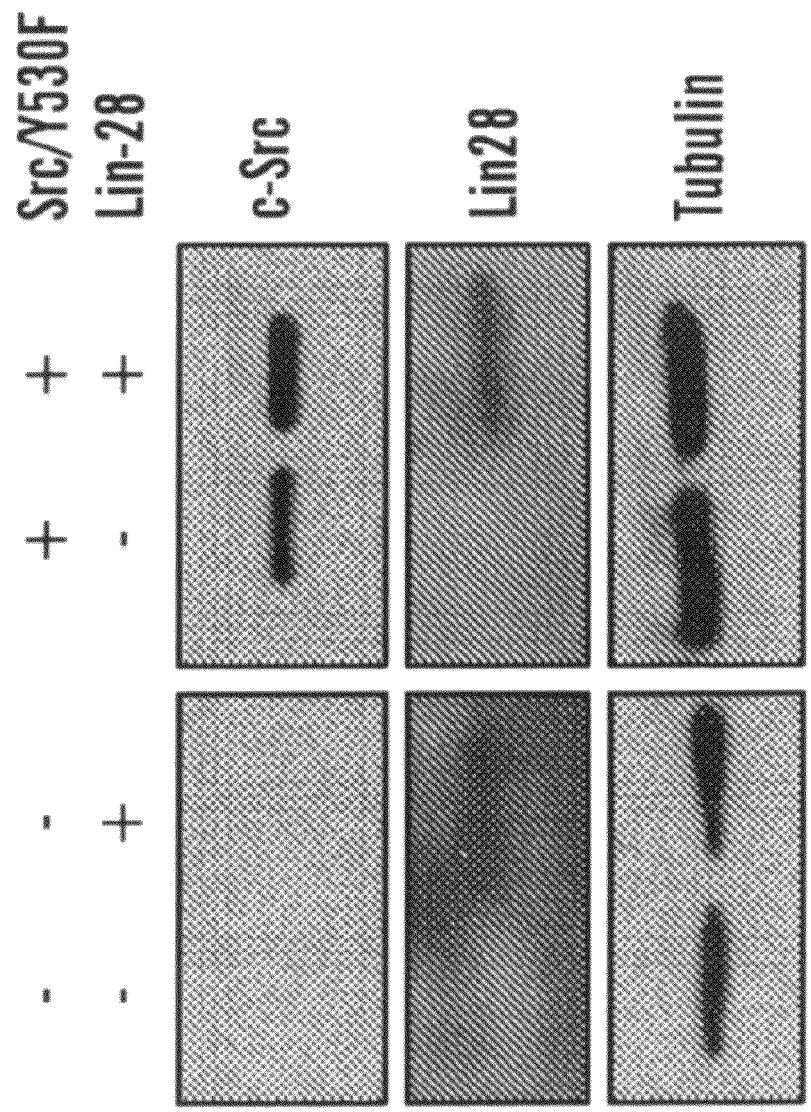
Figure 23B:
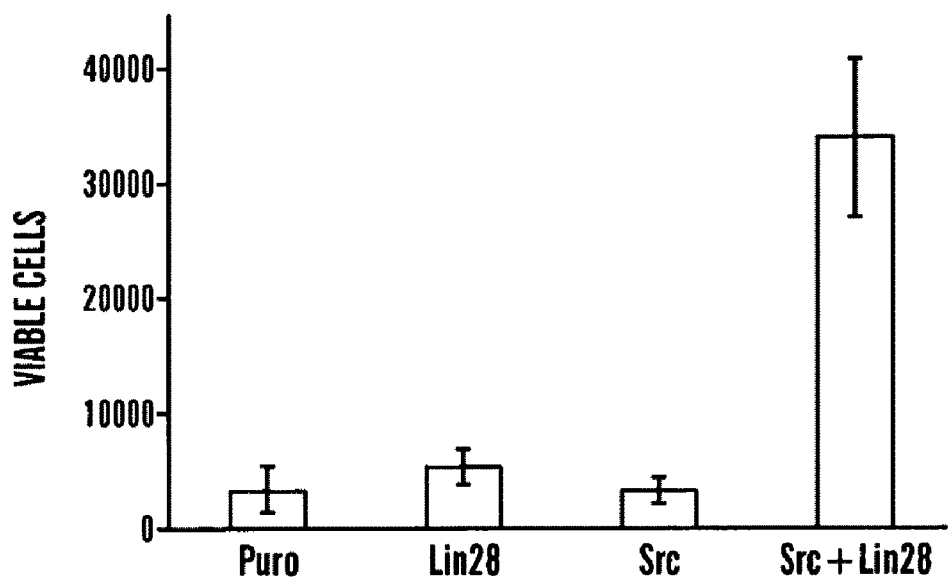
Figure 23C:
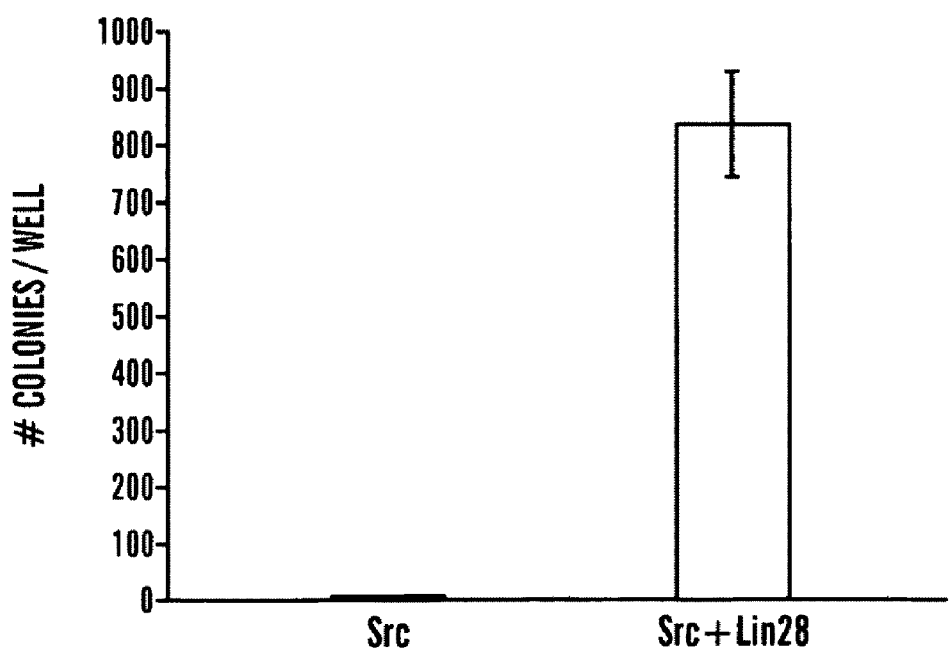

FIG. 23 shows Lin28 cooperates with c-Src/Y530F to transform Ba/F3 cells to factor independence. FIG. 23A shows Western blot analysis on cell extracts from BAF/3 cells infected with pEYK.Src/530F and pMSCV.Neo.Lin28, selected on puromycin and G418. FIG. 23B shows Ba/F3 lines (which were established in FIG. 23A), plated in media without IL-3 at 10,000 cells per well. Cells were stained with Trypan blue and viable cells were counted 6 d after plating. FIG. 23C shows colony formation of Ba/F3 cells expressing Src/Y530F or Src/Y530F+Lin28 in semisolid medium, plated at 50,000 cells per well in medium without IL-3. Quantitation of colony number from soft agar assay after 21 d of growth. Results are plotted as average colony number per well+/−S.E.M., N=3.

FIG. 24 shows Lin28B Knockdown Impairs Growth and Triggers Differentiation of K562 Cells. FIG. 24A shows the level of Lin28B expression determined by quantitative PCR in K562 cells infected with pLKO.controlshRNA or pLKO.Lin28BshRNA, and selected on Puromycin. FIG. 24B shows the levels of mature miR species determined by quantitative PCR in K562 cells were infected with pLKO.controlshRNA or pLKO.Lin28BshRNA, and selected on Puromycin. FIG. 24C shows Western blot analysis on cell extracts from K562 cells infected with pLKO.controlshRNA or pLKO.Lin28BshRNA and selected on Puromycin. FIG. 24D shows the cell proliferation of K562 cells infected with pLKO.controlshRNA or pLKO.Lin28BshRNA, selected on Puromycin, and seeded at 10000 cells per well. Results are plotted as average cell number per well+/−S.E.M. N=3. FIG. 24E shows a Wright-Giemsa stain on cytospin preparation of K562 cells infected with pLKO.controlshRNA or pLKO.Lin28BshRNA, selected on Puromycin.

Figure 25A:
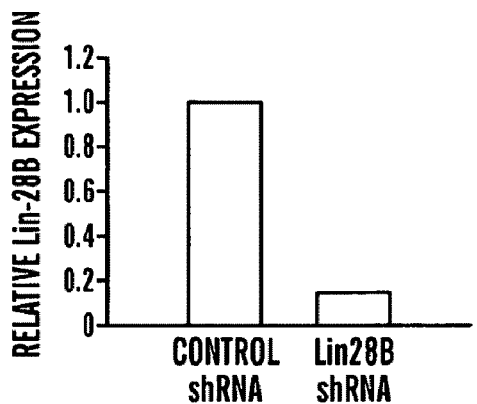
Figure 25B:
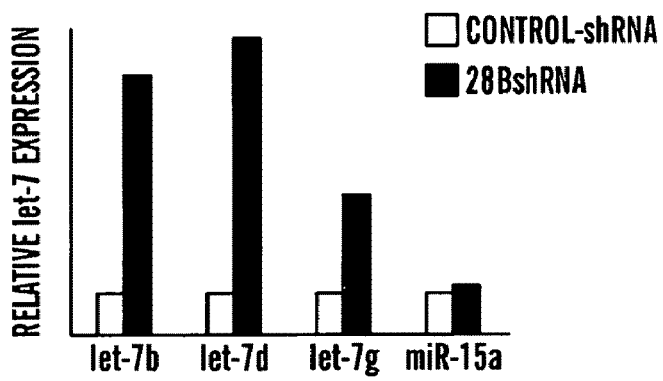
Figure 25C:
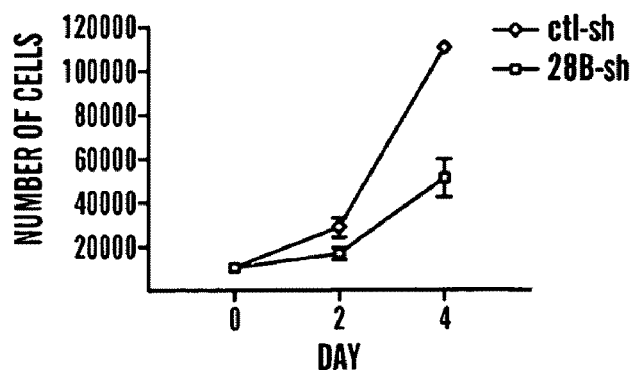

FIG. 25 shows Lin28B Knockdown Impairs Growth of Lama-84 Cells. FIG. 25A shows the level of Lin28B measured by quantitative PCR in Lama-84 cells infected with pLKO.controlshRNA or pLKO.Lin28BshRNA, and selected on Puromycin. FIG. 25B shows the level of mature miR species measured by quantitative PCR in Lama-84 cells infected with pLKO.controlshRNA or pLKO.Lin28BshRNA, and selected on Puromycin. Results from a representative infection are shown. FIG. 25C show the cell proliferation of Lama-84 cells infected with pLKO.controlshRNA or pLKO.Lin28BshRNA, selected on Puromycin, and seeded at 15000 cells per well. Results are plotted as average cell number per well+/−S.E.M. N=3.

Figure 26A:
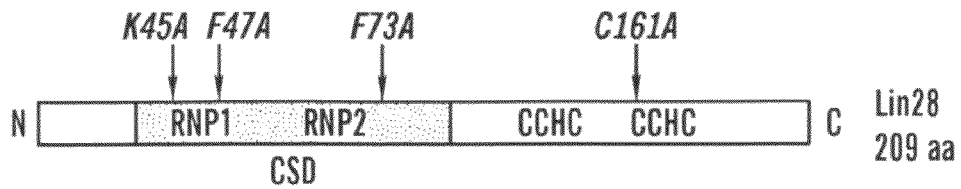
Figure 26B:
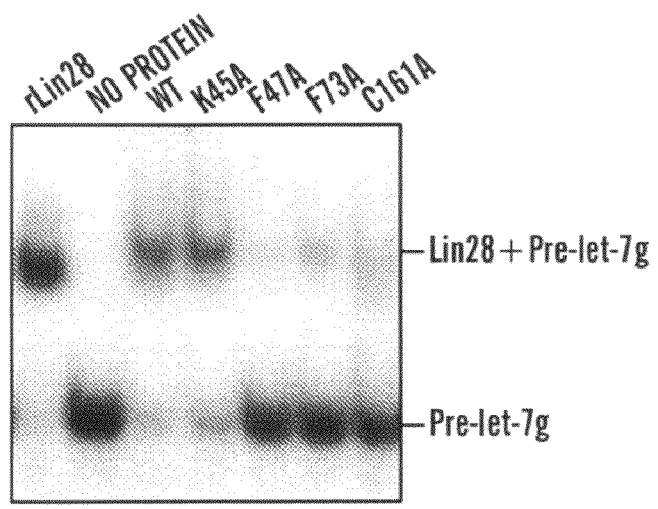
Figure 26C:
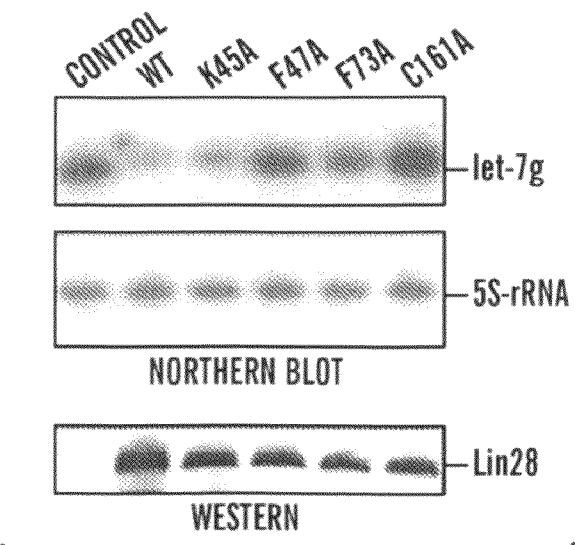

FIG. 26 shows that both the CSD and the zinc finger domains of Lin28 are required for pre-let-7 binding in vitro and processing inhibition in vivo. FIG. 26A shows a schematic representation of Lin28. (N, N terminus; C, C terminus). FIG. 26B shows EMSA performed with FLAG affinity-purified WT and mutant Lin28 proteins (K45A, F47A, F73A, C161A) expressed in HEK293 cells. FIG. 26C shows HEK293 cells which were co-transfected with the pri-let-7g plasmid and 0.5 μg of the pCMV-FLAG empty vector (lane 1) or co-transfected with the pri-let-7g plasmid and 0.5 μg of FLAG-Lin28 wild-type cDNA (lane 2) or the indicated mutant Lin28 (lanes 3-6). Total RNA was collected 40 h after transfection. 20 μg of total RNA from each sample was used for Northern blotting as described previously (Gregory et al., (2004) Nature 432, 235-24010)). Samples were also analyzed for FLAG-Lin28 expression by Western blot.

DETAILED DESCRIPTION OF THE INVENTION

In accordance with the present invention, the inventors have discovered that the developmentally regulated RNA-binding protein, Lin-28 and Lin28B or variants thereof selectively blocks miRNA processing in cells. The inventors have demonstrated using in vitro reconstitution assays and in vivo overexpression and siRNA knockdown studies, that Lin-28 and Lin-28B are endogenous inhibitors of miRNA processing and are necessary and sufficient for blocking microprocessor-mediated cleavage of pri-miRNAs, such as Let 7 miRNA family of miRNAs. Accordingly, the inventors have discovered that Lin-28 and Lin-28B are important negative regulators of miRNA biogenesis and that Lin-28 and Lin28B play a central role in blocking miRNA-mediated differentiation in stem cells and certain cancers.

Aberrant microRNA (also referred to herein as "miR") expression is a hallmark of many human malignancies. A number of human cancer cell lines and primary tumors express low levels of let-7 family miRs and correspondingly increased levels of the let-7 target oncogenes K-Ras, c-myc, and HMGA2. Herein, the inventors demonstrate that the RNA-binding proteins Lin28 and Lin28B block processing of primary let-7 transcripts to mature miRs. The inventors also demonstrate herein that aberrant or increased expression of Lin28/28B promotes oncogenesis. Herein, the inventors demonstrate that Lin28 and Lin28B are over-expressed in a number of human cancer cell lines and primary tumors, and that Lin28 promotes cellular transformation in multiple in vitro assays such as increase self-renewal capacity. The inventors also demonstrate that over-expression of Lin-28 and/or Lin-28B results in the down-regulation of levels of the let-7 family of tumor-suppressor miRs and leads to cancer malignancy. Conversely, the inventors also demonstrate that inhibition or depletion of Lin-28B levels by shRNA knock-down in a multiple human cancer cell lines (i.e. lung adreno-carcinoma and chronic myelogenous leukemia (CML) cell lines) which express Lin28B results in the increase in levels of members of the mature let-7 family of tumor-suppressor miRs and a decrease in cell growth, colony forming capacity and self-renewal capacity of the cells.

Accordingly, in discovering that Lin-28 and Lin28B are endogenous inhibitors of miRNA processing and contributes to biogenesis of miRNA which contribute to stem cell differentiation and cancer, the inventors have discovered that inhibition of Lin-28 is a useful target for the treatment and/or prevention of cancer and stem cell differentiation. Accordingly, one aspect of the present invention relates to a method to treat and/or prevent cancer by inhibition of Lin-28 and/or Lin-28B.

As disclosed herein, the inventors have discovered that knock-down of Lin-28, such as decreased expression or inhibition of the expression Lin-28 and/or Lin-28B, results in increase in the levels of mature let-7 miRNA in human cancer cells and a concomitantly decrease in the self-renewal capacity of such human cancer cells. Accordingly, one aspect of the present invention relates to the inhibition of the expression and/or activity of Lin-28, such as by inhibition of Lin-28 gene expression or inhibition of Lin-28 protein expression and/or protein activity, to increase the levels of mature miRNA levels in cells. In some embodiments, inhibition of Lin-28 is useful to increase the levels of miRNA molecules which function as tumor suppressors (i.e. example, miRNAs which repress the expression or negatively regulate the expression of oncogenes or pro-oncogenes). For example, one embodiment of the present invention to inhibition of Lin-28 is useful to increase the processing of pri-let-7 miRNA and therefore increase the level mature let-7 miRNA in cells so that it can function as a tumor suppressor to repress oncogenes, such as RAS and Hmga2. In other embodiments, inhibition of Lin-28 is useful to increase the level of other miRNAs which function as tumor suppressors, such as for example but not limited to miR-15a, miR-16-1, miR-143, miR-145 and other let-7 family members. Accordingly, one aspect of the present invention relates to methods for the treatment and/or prevention of cancer in a subject, the methods comprising administering to a subject an effective amount of at least one agent which inhibits Lin-28, for example inhibits the gene expression of Lin-28 or inhibits the activity of Lin-28 protein.

In some embodiments, the inhibitor agents of Lin-28 can be, for example but not limited to for example, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The inhibitors can be selected from a group of a chemical, small molecule, chemical entity, nucleic acid sequences, nucleic acid analogues or protein or polypeptide or analogue or fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide inhibitor or fragment thereof, can be, for example, but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, chimeric antibodies, modified proteins and fragments thereof.

The inventors have also discovered that increase in the expression of Lin-28 results in a decrease in the levels of mature miRNA in cells. In an alternative embodiment, another aspect of the present invention relates to the activation of expression or activity of Lin-28 such as increased expression of Lin-28 gene transcript or increase in Lin-28 protein expression and/or activity, to decrease the levels of mature miRNA levels in cells, such as to decrease the levels of oncogenic miRNAs where the miRNA molecules function as oncogenes (also referred to "oncoimers" or "oncomiR" by person of ordinary skill in the art) (Kerscher et al., Nat Rev Cancer; 6; 259-269, 2006). For example, one embodiment of the present invention relating to methods to activate Lin-28 is useful to decrease the level of oncogenic miRNAs in a cell, such as, for example to decrease the processing of oncogenic miRNAs. Accordingly, oncogenic miRNAs which can be reduced by the methods as disclosed herein include, for example but not limited to miR-21, BIC/miR-155, and mir-17-92 (also known as oncomiR-1). Accordingly, one aspect of the present invention relates to methods for the treatment and/or prevention of cancer in a subject, the methods comprising administering to a subject an effective amount of at least one agent which activates Lin-28, for example activates or increases gene expression of Lin-28 or activates the activity of Lin-28 protein.

The inventors have also discovered the presence of Lin-28 in a cell identifies a cell in a more primitive state, for example a precursor or stem-cell like state. Another aspect of the present invention relates to the methods to increase the expression or activation of Lin-28 in cells to direct them to dedifferentiate to become a more primitive differentiation state, for example to trigger the cell to become a precursor or stem-cell like cell.

The inventors have also discovered a method to identify subject having an increased likelihood of developing or having cancer. In some embodiments, the method comprises measuring the level of the expression or activity of Lin-28 in a biological sample obtained from the subject, for example measuring protein expression or gene expression, where the level is compared to a reference level and if the expression or activity level of Lin-28 is higher than the expression or activity of a reference level, the subject is identified as having an increased likelihood of developing cancer.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "Lin-28" as used herein is also referred to in the art as aliases LIN28, LIN-28A, FLJ12457, ZCCHC1, LIN28A, CSDD1 and Lin-28 homolog (*C. elegans*). Human Lin-28 is encoded by nucleic acid corresponding to GenBank Accession No: AF521099 (SEQ ID NO:10) or RefSeq ID: NM_024674 (SEQ ID NO:11), and the human Lin-28 corresponds to protein sequence corresponding to RefSeq ID:AAM77751 (SEQ ID NO:12). Human Lin-28 has a conserved Cold Shock Domain (CSD) between residues 39-112, and two CCHC domains; a type 1 CCHC domain between residues 137-154 and a type 2 CCHC domain between resides 159-176.

The term "Lin-28B" as used herein refers to a homologue of Lin-28, and is also known in the art as CSDD2, FLJ16517, or Lin-28.2. There are two isoforms of Lin-28B, differing in their 5' exons, have been reported, the long isoform (Lin-28B-L also known as isoform 1 or identifier: Q6ZN17-1, corresponding to SEQ ID NO: 26 herein) which has two retroviral-type CCHC zinc-finger motifs and a truncated cold-shock domain, and a short isoform (Lin-28B-S, also known as isoform 2 or identifier: Q6ZN17-2, corresponding to SEQ ID NO: 27 herein) which preserves the two retroviral-type CCHC zinc-finger motifs but contains a truncated cold-shock domain (i.e. lacks 70 N-terminal amino acids as compared to the Lin-28B-L isoform). Human Lin-28B-L has a conserved Cold Shock Domain (CSD) between residues 29-102, and two CCHC domains; a type 1 CCHC domain between residues 127-144 and a type 2 CCHC domain between residues 149-166. Human Lin-28B-L is encoded by nucleic acid corresponding to GenBank Accession No: AK131411 (SEQ ID NO: 28) or RefSeq ID: NM_001004317 (SEQ ID NO: 29), and the human Lin-28B corresponds to protein sequence corresponding to RefSeq ID: NP_001004317 (SEQ ID NO: 30).

The terms "microRNA" or "miRNA" or "miR" are used interchangeably herein refer to endogenous RNA molecules, which act as gene silencers to regulate the expression of protein-coding genes at the post-transcriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

During miRNA maturation in animals, the primary transcript is first processed to a stem-loop precursor and then the stem-loop is processed to yield a mature miRNA of about 22 nucleotides. These molecules can direct the cleavage of mRNA or they can interfere with productive translation of the mRNA, either of which results in reduced protein accumulation and hence the miRNAs are able to modulate gene expression and related cellular activities. miRNAs are important in development and differentiation, and thus the altered expression of miRNAs could be used to alter development and differentiation during tissue engineering and other applications. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. Mimetics of miRNAs include, artificial miRNAs, and siRNAs are inefficient and are not effective for many small RNA sequences.

The term "pri-miRNA" refers to a precursor microRNA molecule having a microRNA sequence in the context of microRNA flanking sequences. A precursor microRNA, also referred to as large RNA precursors, are composed of any type of nucleic acid based molecule capable of accommodating the microRNA flanking sequences and the microRNA sequence. Examples of precursor microRNAs and the individual components of the precursor (flanking sequences and microRNA sequence) are provided herein. The invention, however, is not limited to the examples provided. The invention is based, at least in part, on the discovery of an important component of precursor microRNAs, that is, the microRNA flanking sequences. The nucleotide sequence of the precursor and its components may vary widely. In one aspect a precursor microRNA molecule is an isolated nucleic acid; including microRNA flanking sequences and having a stem-loop structure with a microRNA sequence incorporated therein.

A precursor microRNA molecule may be processed in vivo or in vitro to produce a mature microRNA (miRNA). A precursor microRNA molecule is processed in a host cell by a ribonuclease enzyme or enzymes. One example of a ribonuclease enzyme which processes precursor microRNA molecules is the RNase II ribonuclease Dicer.

The term "pre-miRNA" refers to the intermediate miRNA species from the processing of a pre-miRNA to a mature miRNA. Pre-miRNAs are produced from the processing of a pri-miRNA in the nucleus into a pre-miRNA. Pre-miRNAs undergo additional processing in the cytoplasm to form mature miRNA. Pre-miRNAs are approximately 70 nucleotides long, but can be less than 70 nucleotides or more than 70 nucleotides.

The term "microRNA flanking sequence" as used herein refers to nucleotide sequences including microRNA processing elements. MicroRNA processing elements are the minimal nucleic acid sequences which contribute to the production of mature microRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure. Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2, 200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

The microRNA flanking sequences may be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. The artificial microRNA flanking sequences may be flanking sequences found naturally in the context of other microRNA sequences. Alternatively they may be composed of minimal microRNA processing elements which are found within naturally occurring flanking sequences and inserted into other random nucleic acid sequences that do not naturally occur as flanking sequences or only partially occur as natural flanking sequences. The microRNA flanking sequences within the precursor microRNA molecule may flank one or both sides of the stem-loop structure encompassing the microRNA sequence. Thus, one end (i.e., 5') of the stem-loop structure may be adjacent to a single flanking sequence and the other end (i.e., 3') of the stem-loop structure may not be adjacent to a flanking sequence. Preferred structures have flanking sequences on both lo ends of the stem-loop structure. The flanking sequences may be directly adjacent to one or both ends of the stem-loop structure or may be connected to the stem-loop structure through a linker, additional nucleotides or other molecules.

As used herein, "gene silencing" or "gene silenced" in reference to an activity of a RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example where a target gene is Lin-28 or Lin-28B. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches. In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base pairing may not include any mismatches.

As used herein, the term "let-7" refers to the nucleic acid encoding the let-7 miRNA family members and homologues and variants thereof including conservative substitutions, additions, and deletions therein not adversely affecting the structure or function. Preferably, let-7 refers to the nucleic acid encoding let-7 from *C. elegances* (NCBI Accession No. AY390762), most preferably, let-7 refers to the nucleic acid encoding a let-7 family member from humans, including but not limited to, NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The terms "polypeptide" and "protein" are used interchangeably to refer to a polymer of amino acid residues, and for the purposes of the invention are limited to a minimum length of at least 20 amino acids. Oligopeptides, oligomers multimers, and the like, typically refer to longer chains of amino acids and are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, for purposes of the present invention, a "polypeptide" refers to a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 15 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 15 amino acids in length.

The term "protein" or "polypeptide" as disclosed herein includes all proteins as described below. It will be appreciated that a protein or polypeptide often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in peptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-c arboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a polypeptide inhibitor of Lin-28 or Lin-28B can be comprised of D- or L-amino acid residues, as use of naturally occurring L-amino acid residues has the advantage that any break-down products should be relatively non-toxic to the cell or organism.

In yet a further embodiment, a polypeptide inhibitor of Lin-28 or Lin-28B can be a retro-inverso peptide. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

The term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a Lin-28 polypeptide, for example SEQ ID NO: 12 is meant to refer to a molecule substantially similar in structure and function, i.e. where the function is the ability to process pre-miRNA to mature miR.

For example, a variant of a Lin-28 polypeptide can contain a mutation or modification that differs from a reference amino acid in SEQ ID NO: 12. In some embodiments, a variant of SEQ ID NO: 12 is a fragment of SEQ ID NO: 12 as disclosed herein. In some embodiments, a variant can be a different isoform, for example a variant of Lin-28B (SEQ ID NO: 30) are, for example such as SEQ ID NO: 26 or SEQ ID NO: 27 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of a Lin-28 polypeptide to process the maturation of miRNA). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986);205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a Lin-28, for example a variant of SEQ ID NO: 12 is meant to refer to any molecule substantially similar in structure and function to either the entire molecule of SEQ ID NO: 12 or 30 or to a fragment thereof.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to a molecule such as a protein which possess a biological activity (either functional or structural) that is substantially similar to a biological activity of the entity or molecule its is a functional derivative or functional variant thereof. The term functional derivative is intended to include the fragments, analogues or chemical derivatives of a molecule.

A molecule is said to be "substantially similar" to another molecule if both molecules have substantially similar structures or if both molecules possess a similar biological activity, for example if both molecules are able to deliver a target antigen to the cytosol of a cell in the absence of PA and without being fused to the target antigen. Thus, provided that two molecules possess a similar activity, (i.e. a variant of an Lin-28 polypeptide which can inhibit the processing of pre-miR to mature miR similar to that of the Lin-28 which corresponds to SEQ ID NO: 12) are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical.

As used herein, the term "non-conservative" refers to substituting an amino acid residue for a different amino acid residue that has different chemical properties. The non-conservative substitutions include, but are not limited to aspartic acid (D) being replaced with glycine (G); asparagine (N) being replaced with lysine (K); or alanine (A) being replaced with arginine (R).

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

The term "tumor" or "tumor cell" are used interchangeably herein, refers to the tissue mass or tissue type of cell that is undergoing abnormal proliferation.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see Example VII) (see also Freshney, Culture of Animal Cells: A Manual of Basic Technique (3rd ed. 1994)).

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. Archival tissues, such as those having treatment or outcome history may also be used. As used herein, the term "biological sample" also refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples may be either paraffin-embedded or frozen tissue. The sample can be obtained by removing a sample of cells from a subject, but can also be accomplished by using previously isolated cells (e.g. isolated by another person), or by performing the methods of the invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples may be fresh, fixed, frozen, or embedded in paraffin.

The term "tissue" is intended to include intact cells, blood, blood preparations such as plasma and serum, bones, joints, muscles, smooth muscles, and organs.

The terms "patient", "subject" and "individual" are used interchangeably herein, and refer to an animal, particularly a human, to whom treatment including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e. g. 7 deaza-adenosine; O- and N-alkylated nucleotides, e.g. N6-methyl adenosine are suitable. The 2' OH-group can be replaced by a group selected from H. OR, R. halo, SH, SR, $NH_2$, NHR, $NR_2$ or CN, wherein R is C—C6 alkyl, alkenyl or alkynyl and halo is F. Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "target" as used herein may mean a polynucleotide that may be bound by one or more probes under stringent hybridization conditions.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "treating" includes reducing or alleviating at least one adverse effect or symptom of a condition, disease or disorder associated with inappropriate proliferation, for example cancer. As used herein, the term treating is used to refer to the reduction of a symptom and/or a biochemical marker of in appropriate proliferation, for example a reduction in at lease one biochemical marker of cancer by at least 10%. For example but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as affective treatments by the methods as disclosed herein.

The term "effective amount" as used herein refers to the amount of at least one agent of pharmaceutical composition to reduce or stop at least one symptom of the abnormal proliferation, for example a symptom of a cancer or malignancy. For example, an effective amount using the methods as disclosed herein would be considered as the amount sufficient to reduce a symptom of the abnormal proliferation, for example at least one symptom of a cancer or malignancy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the terms "administering," and "introducing" are used interchangeably and refer to the placement of the agents as disclosed herein into a subject by a method or route which results in at least partial localization of the agents at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "vectors" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

The term "gene product(s)" as used herein refers to include RNA transcribed from a gene, or a polypeptide encoded by a gene or translated from RNA.

The term "inhibition" or "inhibit" when referring to the gene expression and/or activity or protein of Lin-28 refers to a reduction or prevention in the level of its function or a reduction of its gene expression product.

In this specification and the appended claims, the singular forms "a," "an," and "the" include plural references unless the context clearly dictates otherwise, and therefore "a" and "an" are used herein to refer to one or to more than one (i.e., at least one) of the grammatical object of the article. By way of example, "an element" means one element or more than one element, and reference to a composition for delivering "an agent" includes reference to one or more agents.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination."

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the following examples which should not be construed as limiting. The contents of all references cited throughout this application, as well as the figures and tables are incorporated herein by reference. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Biogenesis of microRNA

Without being bound by theory, micro RNAs (also referred to as "miRNAs" or "miR") are small non-coding RNAs, belonging to a class of regulatory molecules found in plants and animals that control gene expression by binding to complementary sites (herein referred to as "target sequences") on target messenger RNA (mRNA) transcripts. miRNAs often function as "gene silencers" to suppress or repress the expression of the gene.

miRNAs are generated from large RNA precursors (termed pri-miRNAs) that are processed in the nucleus into approximately 70 nucleotide pre-miRNAs, which fold into imperfect stem loop structures (Lee, Y., et al., Nature (2003) 425(6956): 415-9). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34).

In other words, the biogenesis of mature miRNAs requires sequential processing steps and can be briefly summarized as involving the processing of pri-miRNA to pre-miRNA, which is subsequently cleaved to a miRNA:miRNA duplex, of which one strand of the duplex is retained as the mature miRNA. In the process of generation of mature miRNAs, large RNA precursors known as pri-miRNAs are processed in the nucleus by the RNase III enzyme, Drosha, and the double-stranded-RNA-binding protein, Pasha (also known as DGCR8), into ~70-nucleotide pre-miRNAs, which fold into imperfect stem-loop structures. The pre-miRNAs are then exported into the cytoplasm by the RAN GTP-dependent transporter exportin 5 and undergo an additional processing step in which a double-stranded RNA of ~22 nucleotides in length, referred to as the miRNA:miRNA* duplex, is excised from the pre-miRNA hairpin by another RNAse III enzyme, known as Dicer. Subsequently, the miRNA:miRNA* duplex is incorporated into the miRISC complex. The mature miRNA strand is retained in the functional miRISC complex and negatively regulates its target genes.

MicroRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the RISC complex. This mechanism of miRNA-mediated gene silencing has been observed mainly in plants (Hamilton, A. J. and D. C. Baulcombe, Science (1999) 286(5441):950-2 and Reinhart, B. J., et al., MicroRNAs in plants. Genes and Dev. (2002) 16:1616-1626), but an example is known from animals (Yekta, S., I. H. Shih, and D. P. Bartel, Science (2004) 304(5670):594-6). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Barter, D. P., Cell (2004) 116(2):281-97).

Hundreds of miRNAs have been identified in the fly, worm, plant and mammalian genomes. The biological role for the majority of the miRNAs remains unknown because almost all of these were found through cloning and bioinformatic approaches (Lagos-Quintana, M., et al., Curr Biol (2002) 12(9):735-9, Lagos-Quintana, M., et al., RNA (2003) 9(2): 175-179, Lagos-Quintana, M., et al., Science (2001) 294 (5543): 853-8; Lee, R. C. and V. Ambros, Science (2001) 294(5543):862-4; Lau, N. C., et al., Science (2001) 294(5543):858-62; Lim, L. P., et al., Genes Dev (2003) 17(8): 991 1008; Johnston, R. J. and O. Robert, Nature (2003) 426 (6968):845-9; and Chang, S., et al. Nature (2004) 430(7001): 785-9).

Lin-28: General Information

Lin-28 is also referred to in the art as aliases LIN-28, LIN28, FLJ12457, ZCCHC1, LIN28A, CSDD1 and Lin-28 homolog (C. elegans). Human Lin-28 is encoded by nucleic acid corresponding to GenBank Accession No: AF521099 (SEQ ID NO:10) or RefSeq ID: NM_024674 (SEQ ID NO:11), and the human Lin-28 corresponds to protein sequence corresponding to RefSeq ID:AAM77751 (SEQ ID NO:12).

The Lin-28 protein may play a role in regulation of cell fate in the developmental stage by binding to mRNA and participating in the translation from mRNA or the stability of mRNA (Moss, E. G. et al., Cell, 88, 637-646, 1997).

As disclosed herein, the inventors have discovered that Lin-28 and/or Lin-28B blocks the processing of pri-miRNA to mature miRNA. Accordingly, Lin-28 and/or Lin-28B was demonstrated to block the processing of the pri-miRNA for let-7 family members, such as but not limited to blocking the processing of pri-let-7g to mature let-7g miRNA. In one embodiment, the present invention relates to methods to increase the level of mature let-7 miRNA family members using agents that inhibit the expression and/or activity of Lin-28 and/or Lin-28B.

Without being bound by theory, let-7 is an endogenous miRNA which functions as a gene silencing molecule to regulate, at the post-transcriptional level, the expression of protein-coding genes that comprise a let-7 target sequence, which can be in the 5' UTR, the 3' UTR (3' untranslated region) or in the coding region of the mRNA transcript.

In some embodiments, the methods as disclosed herein relates to methods to increase the level of let-7 miRNA family members, such as for example but not limited to, let-7 from *C. elegances* (NCBI Accession No. AY390762), and let-7 family member from humans, including but not limited to, NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity. Let-7 also encompasses all isoforms of let-7, for example but not limited to let-7a (SEQ ID NO:13); let-7b (SEQ ID NO:14); hsa-let-7c (SEQ ID NO:15); hsa-let-7d (SEQ ID NO:16); hsa-let-7e (SEQ ID NO:17); hsa-let-7f (SEQ ID NO:18).

In one embodiment, inhibition of Lin-28 and/or Lin-28B using the methods as disclosed herein is useful to increase the level of let-7 family members, for example but not limited to; hsa-let-7a MIMAT0000062: 5'-UGAGGUAGUAGGUU-GUAUAGUU-3' (SEQ ID NO: 13); hsa-let-7b MIMAT0000063: 5'-UGAGGUAGUAGGUUGUGUG-GUU-3' (SEQ ID NO:14); hsa-let-7c MIMAT0000064: 5'-UGAGGUAGUAGGUUGUAUGGUU-3' SEQ ID NO:15); hsa-let-7d MIMAT0000065: 5'-AGAGGUAGUAG-GUUGCAUAGU-3' (SEQ ID NO:16); hsa-let-7e MIMAT0000066: 5'-UGAGGUAGGAGGUUGUAUAGU-3' (SEQ ID NO:17); hsa-let-7f MIMAT0000067: 5'-UGAG-GUAGUAGAUUGUAUAGUU-3 (SEQ ID NO:18). In some embodiments, the let-7 miRNA is let-7a isoform, of hsa-let-7a MIMAT0000062: 5'-UGAGGUAGUAGGUU-GUAUAGUU-3' (SEQ ID NO:13).

In some embodiments, the let-7 miRNA which biogenesis or processing is inhibited by Lin-28 and/or Lin-28B is let-7 pri-miRNA. In some embodiments, the let-7 miRNA is 5'-UGGGAUGAGGUAGUAGGUUGUAUAGU-UUUAGGGUCACACCCACCACUGGG AGAUAAC-UAUACAAUCUACUGUCUUUCCUA-3' (SEQ ID NO:19), also called MI0000060 herein.

Agents that Inhibit Lin-28

In some embodiments, agents which inhibit Lin-28 and/or Lin-28B useful in the methods as disclosed herein can be, for example but are not limited to, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The inhibitors can be selected from a group of a chemical, small molecule, chemical entity, nucleic acid sequences, nucleic acid analogues or protein or polypeptide or analogue or fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide inhibitor or fragment thereof, can be, for example, but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, chimeric antibodies, modified proteins and fragments thereof.

In some embodiments, the present invention relates to the inhibition of the expression of Lin-28 and/or Lin-28B gene transcript and/or inhibition of Lin-28 and/or Lin-28B protein activation or protein expression. In some embodiments, inhibition of Lin-28 and/or Lin-28B can be inhibition of nucleic acid transcripts encoding Lin-28, for example inhibition of messenger RNA (mRNA). In alternative embodiments, inhibition of Lin-28 and/or Lin-28B can be a decrease or inhibition of the expression and/or inhibition of activity of the Lin-28 and/or Lin-28B protein or Lin-28 gene product or isoforms thereof.

In some embodiments, inhibition of expression or activity of Lin-28 and/or Lin-28B is by an agent. One can use any agent, for example and agent useful in the methods as disclosed herein can be, but is not limited to nucleic acids, nucleic acid analogues, peptides, phage, phagemids, polypeptides, peptidomimetics, ribosomes, aptamers, antibodies, small or large organic or inorganic molecules, or any combination thereof. In some embodiments, agents useful in methods of the present invention include agents that function as inhibitors of Lin-28 and/or Lin-28B expression, for example inhibitors of mRNA encoding Lin-28.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

As used herein, agents useful in the method as inhibitors of Lin-28 and/or Lin-28B expression and/or inhibition of Lin-28 and/or Lin-28B protein function can be any type of entity, for example but are not limited to chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety. For example, in some embodiments, the chemical moiety is a pyrimidione-based compound as disclosed herein.

In alternative embodiments, agents useful in the methods as disclosed herein are proteins and/or peptides or fragment thereof, which inhibit the gene expression of Lin-28 and/or Lin-28B or the function of the Lin-28 and/or Lin-28B protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Alternatively, agents useful in the methods as disclosed herein as inhibitors of Lin-28 and/or Lin-28B can be a chemicals, small molecule, large molecule or entity or moiety, including without limitation synthetic and naturally-occurring non-proteinaceous entities. In certain embodiments the agent is a small molecule having the chemical moieties as disclosed herein.

Nucleic acid Inhibitors of Lin-28

In some embodiments, agents that inhibit Lin-28 and/or Lin-28B are nucleic acids. Nucleic acid inhibitors of Lin-28 and/or Lin-28B are for example, but not are limited to, RNA interference-inducing molecules, for example but are not limited to siRNA, dsRNA, stRNA, shRNA and modified versions thereof, where the RNA interference molecule silences the gene expression of Lin-28 and/or Lin-28B. In some embodiments, the nucleic acid inhibitor of Lin-28 and/or Lin-28B is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Lin-28 can be reduced by inhibition of the expression of Lin-28 and/or Lin-28B polypeptide or by "gene silencing" methods commonly known by persons of ordinary skill in the art.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" are defined as agents which function to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the Lin-28 and/or Lin-28B sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting Lin-28 and/or Lin-28B expression can be readily designed and tested. Accordingly, siRNAs useful for the methods described herein include siRNA molecules of about 15 to about 40 or about 15 to about 28 nucleotides in length, which are homologous to a Lin-28 and/or Lin-28B gene. Preferably, a Lin-28 and/or Lin-28B targeting siRNA molecules have a length of about 19 to about 25 nucleotides. More preferably, a Lin-28 targeting siRNA molecule can have a length of about 19, 20, 21, or 22 nucleotides. A Lin-28 targeting siRNA molecule can also comprise a 3' hydroxyl group. A Lin-28 targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the Lin-28 and/or Lin-28B targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the Lin-28 targeting RNA molecule is double stranded—one strand has a 3' overhang and the other strand can be blunt-ended or have an overhang. In the embodiment in which the Lin-28 targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Lin-28 mRNA has been successfully targeted using siRNAs and such siRNA or vectors for preparing them are commercially available, for example from Invitrogen. In some embodiments, assessment of the expression and/or knock down of Lin-28 and/or Lin-28B protein using such Lin-28 and/or Lin-28B siRNAs can be determined using methods commonly known by persons in the art, for example, immunoblot assays, western blots, ELISA, quantitative RT-PCR methods such as taqman or other real-time PCR methods or using commercially available kits.

In some embodiments, siRNA molecules which are useful in the methods and compositions as disclosed herein to inhibit Lin-28 and/or Lin28B are disclosed in the methods section of the Examples, such as, for example but not limited to SEQ ID NO:7, SEQ ID NO:8 and SEQ ID NO:9 or variants or homologues thereof, which are commercially available from Broad-TRC Collection (Sigma-Aldrich). In alternative embodiments, persons of ordinary skill in the art can readily prepare RNAi molecules based on the known sequence of the target mRNA. To avoid doubt, the sequence of a human Lin-28 cDNA is provided, at for example, GenBank Accession No: AF521099 (SEQ ID NO:10) or NM_024674 (SEQ ID NO:11). The sequence at NM_024674 (SEQ ID NO:11) is the following:

```
   1 gtgcggggga agatgtagca gcttcttctc cgaaccaacc ctttgccttc ggacttctcc
  61 ggggccagca gccgcccgac caggggcccg gggccacggg ctcagccgac gaccatgggc
 121 tccgtgtcca accagcagtt tgcaggtggc tgcgccaagg cggcagaaga ggcgcccgag
 181 gaggcgccgg aggacgcggc ccgggcggcg gacgagcctc agctgctgca cggtgcgggc
 241 atctgtaagt ggttcaacgt gcgcatgggg ttcggcttcc tgtccatgac cgcccgcgcc
 301 ggggtcgcgc tcgaccccccc agtggatgtc tttgtgcacc agagtaagct gcacatggaa
 361 gggttccgga gcttgaagga gggtgaggca gtggagttca cctttaagaa gtcagccaag
 421 ggtctggaat ccatccgtgt caccggacct ggtggagtat tctgtattgg gagtgagagg
 481 cggccaaaag gaaagagcat gcagaagcgc agatcaaaag gagacaggtg ctacaactgt
 541 ggaggtctag atcatcatgc caaggaatgc aagctgccac cccagcccaa gaagtgccac
 601 ttctgccaga gcatcagcca tatggtagcc tcatgtccgc tgaaggccca gcagggccct
 661 agtgcacagg gaaagccaac ctactttcga gaggaagaag aagaaatcca cagccctacc
 721 ctgctcccgg aggcacagaa ttgagccaca atgggtgggg gctattcttt tgctatcagg
 781 aagttttgag gagcaggcag agtggagaaa gtgggaatag ggtgcattgg ggctagttgg
 841 cactgccatg tatctcaggc ttgggttcac accatcaccc tttcttccct ctaggtgggg
 901 ggaaagggtg agtcaaagga actccaacca tgctctgtcc aaatgcaagt gagggttctg
 961 ggggcaacca ggaggggga atcaccctac aacctgcata ctttgagtct ccatccccag
1021 aatttccagc ttttgaaagt ggcctggata gggaagttgt tttccttttaa agaaggata
1081 tataataatt cccatgccag agtgaaatga ttaagtataa accagattc atggagccaa
1141 gccactacat tctgtggaag gagatctctc aggagtaagc attgtttttt tttcacatct
1201 tgtatcctca tacccacttt tgggataggg tgctggcagc tgtcccaagc aatgggtaat
1261 gatgatggca aaaagggtgt ttggggggaac agctgcagac ctgctgctct atgctcaccc
1321 ccgcccatt ctgggccaat gtgattttat ttatttgctc ccttggatac tgcaccttgg
1381 gtcccacttt ctccaggatg ccaactgcac tagctgtgtg cgaatgacgt atcttgtgca
1441 ttttaacttt ttttccttaa tataaatatt ctggttttgt attttttgtat attttaatct
1501 aaggccctca tttcctgcac tgtgttctca ggtacatgag caatctcagg gatagccagc
1561 agcagctcca ggtctgcgca gcaggaatta cttttttgttg ttttttgccac cgtgggagagc
1621 aactatttgg agtgcacagc ctattgaact acctcatttt tgccaataag agctggcttt
1681 tctgccatag tgtcctcttg aaaccccctc tgccttgaaa atgttttatg ggagactagg
1741 ttttaactgg gtggccccat gacttgattg ccttctactg gaagattggg aattagtcta
1801 aacaggaaat ggtggtacac agaggctagg agaggctggg cccggtgaaa aggccagaga
1861 gcaagccaag attaggtgag ggttgtctaa tcctatggca caggacgtgc tttacatctc
1921 cagatctgtt cttcaccaga ttaggttagg cctaccatgt gccacaggg gtgtgtgtgt
1981 ttgtaaaact agagttgcta aggataagtt taaagaccaa taccctgta cttaatcctg
2041 tgctgtcgag ggatggatat atgaagtaag gtgagatcct taacctttca aaattttcgg
2101 gttccaggga gacacacaag cgagggtttt gtggtgcctg gagcctgtgt cctgccctgc
2161 tacagtagtg attaatagtg tcatggtagc taaaggagaa aaaggggggtt tcgtttacac
2221 gctgtgagat caccgcaaac ctaccttact gtgttgaaac gggacaaatg caatagaacg
2281 cattgggtgg tgtgtgtctg atcctgggtt cttgtctccc ctaaatgctg ccccccaagt
2341 tactgtattt gtctgggctt tgtaggactt cactacgttg attgctaggt ggcctagttt
2401 gtgtaaatat aatgtattgg tcttctctccg tgttctttgg gggttttgtt tacaaacttc
```

-continued

```
2461 tttttgtatt gagagaaaaa tagccaaagc atctttgaca gaaggttctg caccaggcaa 2521 aaagatctga aacattagtt tgggggggcc tcttcttaaa gtggggatct tgaaccatcc 2581 tttcttttgt attccccttc ccctattacc tattagacca gatcttctgt cctaaaaact 2641 tgtcttctac cctgccctct tttctgttca cccccaaaag aaaacttaca cacccacaca 2701 catacacatt tcatgcttgg agtgtctcca caactcttaa atgatgtatg caaaaatact 2761 gaagctagga aaaccctcca tcccttgttc ccaacctcct aagtcaagac cattaccatt 2821 tctttctttc tttttttttt tttttttaaaa tggagtctca ctgtgtcacc caggctggag 2881 tgcagtggca tgatcggctc actgcagcct ctgcctcttg ggttcaagtg attctcctgc 2941 ctcagcctcc tgagtagctg ggatttcagg cacccgccac actcagctaa ttttttgtatt 3001 tttagtagag acggggtttc accatgttgt ccaggctggt ctggaactcc tgacctcagg 3061 tgatctgccc accttggctt cccaaagtgc tgggattaca ggcatgagcc accatgctgg 3121 gccaaccatt tcttggtgta ttcatgccaa acacttaaga cactgctgta gcccaggcgc 3181 ggtggctcac acctgtaatc ccagcacttt ggaaggctga ggcgggcgga tcacaaggtc 3241 acgagttcaa aactatcctg gccaacacag tgaaaccccg tctctactaa aatacaaaaa 3301 aattagccgg gtgtggtggt gcatgccttt agtcctagct attcaggagg ctgaggcagg 3361 ggaatcgctt gaacccgaga ggcagaggtt gcagtgagct gagatcgcac cactgcactc 3421 cagcctggtt acagagcaag actctgtctc aaacaaaaca aaacaaaaca aaaacacact 3481 actgtatttt ggatggatca aacctcctta attttaattt ctaatcctaa agtaaagaga 3541 tgcaattggg ggccttccat gtagaaagtg gggtcaggag gccaagaaag ggaatatgaa 3601 tgtatatcca agtcactcag gaactttat gcaggtgcta gaaactttat gtcaaagtgg 3661 ccacaagatt gtttaatagg agacgaacga atgtaactcc atgtttactg ctaaaaacca 3721 aagctttgtg taaaatcttg aatttatggg gcgggagggt aggaaagcct gtacctgtct 3781 gttttttttcc tgatcctttt ccctcattcc tgaactgcag gagactgagc cccttttgggc 3841 tttggtgacc ccatcactgg ggtgtgttta tttgatggtt gattttgctg tactgggtac 3901 ttccttttccc attttctaat cattttttaa cacaagctga ctcttcccttt cccttctcct 3961 ttccctggga aaatacaatg aataaataaa gacttattgg tacgcaaact gtca
``` siRNA sequences are chosen to maximize the uptake of the antisense (guide) strand of the siRNA into RISC and thereby maximize the ability of RISC to target human Lin-28 and/or Lin-28B mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human Lin-28 and/or Lin-28B mRNA.

In another embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, Lin-28. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, retroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In some embodiments, an agent is protein or polypeptide or RNAi agent that inhibits expression of Lin-28 and/or Lin-28B gene product, and/or alternatively inhibits the activity of Lin-28 and/or Lin-28B protein. In such embodiments cells can be modified (e.g., by homologous recombination) to provide increased expression of such an agent, for example by replacing, in whole or in part, the naturally occurring promoter with all or part of a heterologous promoter so that the cells express the natural inhibitor agent of Lin-28 and/or Lin-28B, for example protein or miRNA inhibitor of Lin-28 and/or Lin-28B at higher levels. The heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (W093/09222) by Selden et al.; and PCT/US90/06436 (WO91/06667) by Skoultchi et al. The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of the peptide or nucleic acid agent inhibitor of Lin-28 can also include an affinity column containing agents which will bind to the protein; one or more column steps over such affinity resins as concanavalin A-agarose, Heparin-Toyopearl™ or Cibacrom blue 3GA Sepharose; one or more steps involving hydrophobic interaction chromatography using such resins as phenyl ether, butyl ether, or propyl ether; immunoaffinity chromatography, or complementary cDNA affinity chromatography.

In one embodiment, a nucleic acid inhibitor of Lin-28 and/or Lin-28B can be obtained synthetically, for example, by chemically synthesizing a nucleic acid by any method of synthesis known to the skilled artisan. The synthesized nucleic acid inhibitors of Lin-28 can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), diinethylene-sulfoxide ($—CH_2—SO—CH_2$), dimethylene-sulfone ($—CH_2—SO_2—CH_2$), 2'-O-alkyl, and 2'-deoxy-2'-fluoro'phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci., USA* 98:8012-8017; and Tuschl, T. et al. (1999) *Genes & Development* 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) *Genes Dev.* 16:948-958; McManus, M. T. et al. (2002) *RNA* 8:842-850; Paul, C. P. et al. (2002) *Nat. Biotechnol.* 20:505-508; Miyagishi, M. et al.

(2002) *Nat. Biotechnol.* 20:497-500; Sui, G. et al. (2002) *Proc. Natl. Acad. Sci., USA* 99:5515-5520; Brummelkamp, T. et al. (2002) *Cancer Cell* 2:243; Lee, N. S., et al. (2002) *Nat. Biotechnol.* 20:500-505; Yu, J. Y., et al. (2002) *Proc. Natl. Acad. Sci., USA* 99:6047-6052; Zeng, Y., et al. (2002) *Mol. Cell* 9:1327-1333; Rubinson, D. A., et al. (2003) *Nat. Genet.* 33:401-406; Stewart, S. A., et al. (2003) *RNA* 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., a Lin-28 coding sequence of SEQ ID NO:10 and SEQ ID NO:11, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as Oligoengine®, can also be used to select siRNA sequences against EST libraries to ensure that only one gene is targeted.

In some embodiments, agents which inhibit Lin-28 can be endogenous miRNA molecules that have target sites in the Lin-28 nucleotide sequence which can result in gene silencing of Lin-28. Such endogenous miRNA molecules useful in the methods of the present invention include, for example but are not limited to, Lin-4, let-7 (as disclosed in U.S. Patent application 2006/247193, which is incorporated herein by reference) and or miR-125a (disclosed in International Patent Application WO07/025187, which is incorporated herein by reference), or synthetic miRNAs such as synthetic let-7b as disclosed in U.S. Patent application 2006/247193, or antagomirs thereof.

Delivery of RNA Interfering Agents:

Methods of delivering RNA interfering agents, e.g., an siRNA, or vectors containing an RNA interfering agent, to the target cells (e.g., cells of the brain or other desired target cells, for cells in the central and peripheral nervous systems), can include, for example (i) injection of a composition containing the RNA interfering agent, e.g., an siRNA, or (ii) directly contacting the cell, e.g., a cell of the brain, with a composition comprising an RNA interfering agent, e.g., an siRNA. In another embodiment, RNA interfering agents, e.g., an siRNA can be injected directly into any blood vessel, such as vein, artery, venule or arteriole, via, e.g., hydrodynamic injection or catheterization. In some embodiments inhibitory Lin-28 and/or Lin-28B agents such as a Lin-28 siRNA can delivered to specific organs, for example the liver, bone marrow or systemic administration.

Administration can be by a single injection or by two or more injections. RNA interfering agents can be delivered in a pharmaceutically acceptable carrier. One or more RNA interfering agents can be used simultaneously. The RNA interfering agents, e.g., the siRNAs targeting Lin-28 and/or Lin-28B mRNA, can be delivered singly, or in combination with other RNA interfering agents, e.g., siRNAs, such as, for example siRNAs directed to other cellular genes. Lin-28 siRNAs can also be administered in combination with other pharmaceutical agents which are used to treat or prevent cancers or malignancies associated with abnormal cellular proliferation.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into specific cells. For example, an antibody-protamine fusion protein when mixed with an siRNA, binds siRNA and selectively delivers the siRNA into cells expressing an antigen recognized by the antibody, resulting in silencing of gene expression only in those specific cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) *Nat Biotechnol* 20(10): 1006). Plasmid- or viral-mediated delivery mechanisms of shRNA can also be employed to deliver shRNAs to cells in vitro and in vivo as described in Rubinson, D. A., et al. ((2003) *Nat. Genet.* 33:401-406) and Stewart, S. A., et al. ((2003) *RNA* 9:493-501).

RNA interfering agents, for e.g., an siRNA, can also be introduced into cells via the vascular or extravascular circulation, the blood or lymph system, and the cerebrospinal fluid.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi molecules do not have to match perfectly to their target sequence. Preferably, however, the 5' and middle part of the antisense (guide) strand of the siRNA is perfectly complementary to the target nucleic acid sequence.

Accordingly, the RNAi molecules functioning as nucleic acid inhibitors of Lin-28 and/or Lin-28B useful in the present invention are for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297:2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of Lin-28 and/or Lin-28B is any agent which binds to and inhibits the expression of Lin-28 mRNA, where the expression of Lin-28 mRNA or a product of transcription of nucleic acid encoded by SEQ ID NO:10, 11, or 30 is inhibited.

In another embodiment of the invention, an agent which inhibits Lin-28 and/or Lin-28B is a catalytic nucleic acid construct, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of Lin-28 and/or Lin-28B or homologues or variants thereof can be achieved by techniques well known to those skilled in the art (for example Lleber and Strauss, (1995) Mol Cell Biol 15:540.551, the disclosure of which is incorporated herein by reference).

Proteins and Peptide Inhibitors of Lin-28

In some embodiments, an agent which inhibits Lin-28 or Lin-28B is a protein and/or peptide inhibitor or fragment inhibitor of Lin-28, for example, but not limited to mutated proteins of Lin-28; therapeutic proteins and recombinant proteins. Proteins and peptides inhibitors can also include for example mutated proteins, genetically modified proteins, peptides, synthetic peptides, recombinant proteins, chimeric proteins, antibodies, humanized proteins, humanized antibodies, chimeric antibodies, modified proteins and fragments thereof.

In some embodiments, an agent which inhibits Lin-28 and/or Lin-28B is a dominant negative variants of Lin-28 and/or Lin-28B, for example a non-functional variant of Lin-28 and/or Lin-28B. For example, and as disclosed herein in the Examples, a useful dominant negative inhibitor of Lin-28 and/or Lin-28B is a mutant Lin-28 or Lin-28B polypeptide with at least one amino acid change in the Cold Shock Domain (CSD) and/or the CCHC domain. In some embodiments, a useful dominant negative Lin-28 or Lin-28B polypeptide useful in the methods and compositions as disclosed herein is a Lin-28 polypeptide or fragment thereof which has at least one of the following mutations; F47A, or F73A or C161A which results in the abolishing of the let-7 binding and abolishing the inhibition of miR processing.

Antibodies

In some embodiments, inhibitors of genes and/or gene products useful in the methods of the present invention include, for example, antibodies, including monoclonal, chimeric humanized, and recombinant antibodies and antigen-binding fragments thereof. In some embodiments, neutralizing antibodies can be used as inhibitors of the Lin-28 and/or Lin-28B protein. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies.

In one embodiment of this invention, the inhibitor to Lin-28 and/or Lin-28B can be an antibody molecule or the epitope-binding moiety of an antibody molecule and the like. Antibodies which provide high binding avidity and unique specificity to a wide range of target antigens and haptens are desirable. Monoclonal antibodies useful in the practice of the present invention include whole antibody and fragments thereof and are generated in accordance with conventional techniques, such as hybridoma synthesis, recombinant DNA techniques and protein synthesis.

In some embodiments, a neutralizing antibody useful as an inhibitor to Lin-28 and/or Lin-28B is an antibody which binds with high binding avidity and affinity to a functional domain of Lin-28, for example to a portion or a few residues within the CSD domain and/or a CCHC domain of Lin-28, for example, where residues 39-112 are the CSD domain and a type 1 CCHC domain is between residues 137-154 and a type 2 CCHC domain between residues 159-176. In one embodiment, an antibody useful in the methods and compositions as disclosed herein is an antibody which binds with specific affinity to a region of the Lin-28 or Lin-28B polypeptide which comprises at least one of the following residues A47, F72 or C161.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)$_2$, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarily-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Bioassay for Identifying Lin-28 Inhibitors:

In some embodiments, the methods of the present invention relate to use of inhibitors of Lin-28 and/or Lin-28B for the treatment or prevention of cancers or abnormal proliferation. Where necessary, an agent useful in the methods and compositions as disclosed herein can be assessed for its ability to function as an inhibitor of Lin-28 and/or Lin-28B protein. One such assessment is assessed using a bioassay such as the one disclosed in the Examples herein, wherein the level of mature let-7 miRNA is measured in the presence of an agent which inhibits Lin-28 and/or Lin-28B (or knockdown its expression, such as, for example shRNA of SEQ ID NO: 7, 8 and 9) as is compared with the level of mature let-7 miRNA in the absence of such agents. An increase in the level of mature let-7 miRNA and/or a decrease in Lin-28 and/or Lin-28B protein and/or a decrease in Lin-28 and/or Lin-28B mRNA transcript level indicates the agent functions as an inhibitor of Lin-28, an is useful in the methods as disclosed herein. Alternatively, the level of mature let-7 miRNA in the presence of an agent which inhibits Lin-28 and/or Lin-28B can be compared with the level of mature let-7 miRNA in the presence of a positive control (i.e. an agent known to inhibit Lin-28 such as shRNAs of SEQ ID NO: 7-9) or in the presence of a negative control which is known not to have an effect on Lin-28.

Where the test agent inhibitor of Lin-28/Lin-28B results in a substantially similar, i.e. about at least 60%, or at least about 70%, or at least about 80% or at least about 90% or more increase in the level of let-7 miRNA expression as compared to the positive control, indicates that the agent functions as an inhibitor of Lin-28, an is useful in the methods as disclosed herein the agent.

Alternatively, an agent useful in the methods and compositions as disclosed herein can be assessed for its ability to function as an inhibitor of Lin-28 and/or Lin-28B protein by assessing the cell proliferation (or cell growth) of a cancer cell line, such as the H1299 lung adrenocarcinoma or chronic myelogenous leukemia (CML) cell lines (as disclosed herein in the Examples) in the presence of the inhibitor of Lin-28. An decrease in the cell proliferation rate (or cell growth) in the presence of the inhibitor of Lin-28 and/or Lin-28B as compared to in the absence of an agent, or a negative control indicates the agent functions as an inhibitor of Lin-28, an is useful in the methods as disclosed herein. Alternatively, a substantially similar i.e. about at least 60%, or at least about 70%, or at least about 80% or at least about 90% or more cell proliferation rate (or cell growth) in the presence of the inhibitor of Lin-28 and/or Lin-28B as compared to the presence of a positive control (i.e. an agent known to inhibit Lin-28 such as shRNAs of SEQ ID NO: 7-9) indicates the agent functions as an inhibitor of Lin-28, an is useful in the methods as disclosed herein.

Methods to Identify Subjects Amenable for Treatment with Inhibitors of Lin-28:

Subjects amenable to treatment using the methods as disclosed herein include subjects at risk of a cancer, as well as subjects at risk of developing cancer.

In some embodiments, subjects amenable to treatment of inhibitors of Lin-28 and/or Lin-28B using the methods as disclosed herein include subjects identified with or having increased risk of cancer, for example subjects identified to carry a genetic mutation or polymorphism associated with an increase risk of developing cancer. Such mutations and genetic susceptibility genes and loci are commonly known by persons skilled in the art, for example some of the more commonly known genes where a mutation is associated with increase in cancer include, but are not limited to; BRAC1, BRAC2, EGFR, EIF4A2, ERBB2, RB1, CDKN2A, P53, INK4a, APC, MLH1, MSH2, MSH6, WTI, NF1, NF2, and VHL (see world-wide web at web site: cancer.org/docroot/ETO/content/ETO_1_4x_oncogenes_and_tumor_suppressor_genes-dot-asp).

In some embodiments, subjects can be screened for their likelihood of having or developing cancer based on a number of biochemical and genetic markers or other biomarkers. Biomarkers are defined as cellular, biochemical, molecular or genetic alterations by which a normal, abnormal or simply biologic process can be recognized or monitored. Biomarkers are measurable in biological media, such as human tissues, cells or fluids. Biomarkers could be used to identify pathological processes before individuals become symptomatic or to identify individuals who are susceptible to cancer.

Several classes of biomarkers in cancer cells and bodily fluids have been studied, mostly in laboratories examining specific observations but also in limited clinical settings. Several biomarkers have shown only limited utility: e.g., CD44, telomerase, transforming growth factor-α (TGF-α)3, transforming growth factor-β (TGF-β), epidermal growth factor receptor erbB-2 (erbB-2), epidermal growth factor receptor erbB-3 (erbB-3), mucin 1 (MUC1), mucin 2 (MUC2) and cytokeratin 20 (CK20). Other biomarkers are used in clinical practice and include, for example Prostate specific antigen (PSA) and cancer antibody or tumor marker 125 (CA125). Several protein markers can be used as cancer biomarkers, for example but not limited to, Fecal occult blood test (FOBT), which is a protein biomarker shown to decrease cause-specific mortality in cancer screens.

In one embodiment, subjects amenable to treatment using the methods as disclosed herein include subjects with a high level of Lin-28 and/or Lin-28B in a biological sample from the subject as compared to a reference level of Lin-28, and thus have reduced processing of tumor suppressor miRNAs, such as let-7 miRNA. In some embodiments, the subject is assessed if they are at risk of having cancer by identifying the level of Lin-28 and/or Lin-28B in a biological sample from the subject and comparing the level of Lin-28 and/or Lin-28B with a reference level of Lin-28. For example, if the level of Lin-28 and/or Lin-28B in a biological sample from the subject is above a reference level, the subject is at risk of having a metastasis or a malignant cancer. In some embodiments, the biological sample obtained from the subject is from a biopsy tissue sample, and in some embodiments, the sample is from a tumor or cancer tissue sample. The level of Lin-28 and/or Lin-28B can be determined by any method known by one of ordinary skill in the art, for example by northern blot analysis or RT-PCR for mRNA expression levels, or ELISA or western blot analysis for protein expression levels.

In some embodiments, a reference level of Lin-28 and/or Lin-28B is the level of Lin-28 and/or Lin-28B that does not result in malignancy or a malignant cancer. In some embodiments, the reference level of Lin-28 the based on the level of Lin-28 expression or protein activity in a normal tissue sample, where in the tissue sample is a biological tissue sample from a tissue matched, species matched and age matched biological sample. In some embodiments, the reference level of Lin-28 is based on a biological sample is from a non-malignant matched tissue sample. In some embodiments, the reference level of Lin-28 is based on a biological sample from normal tissue, for example non-cancer tissue, or a non-stem cell cancer tissue sample.

In alternative embodiments, a subject amenable to treatment using the methods as disclosed herein include subjects with a low level of Let-7 miRNA family members in a biological sample from the subject as compared to a reference level of Let-7 miRNA, and thus have reduced suppression of oncogenes expression. In some embodiments, the subject is assessed if they are at risk of having cancer by identifying the level of let-7 miRNA in a biological sample from the subject and comparing the level of let-7 miRNA with a reference level of let-7 miRNA. For example, if the level of let-7 miRNA in a biological sample from the subject is below a reference level, the subject is at risk of having a metastasis or a malignant cancer. In some embodiments, the biological sample obtained from the subject is from a biopsy tissue sample, and in some embodiments, the sample is from a tumor or cancer tissue sample. The level of let-7 miRNA can be determined by methods known by the skilled artisan, for example by northern blot analysis or RT-PCR. In some embodiments, the reference level of let-7 miRNA is the level of let-7 miRNA that does not result in malignancy or a malignant cancer. In some embodiments, the reference level of let-7 miRNA is the based on the level of let-7 miRNA expression in a normal tissue sample, where in the tissue sample is a biological tissue sample from a tissue matched, species matched and age matched biological sample. In some embodiments, the reference level of let-7 miRNA is based on a biological sample is from a non-malignant matched tissue sample. In some embodiments, the reference level let-7 miRNA is based on a biological sample from a non-stem cell cancer tissue sample.

Assessment of Inhibitors of Lin-28 in Models of Cancer and/or Abnormal Proliferation.

In some embodiments, an agent inhibiting Lin-28 and/or Lin-28B can be assessed in animal models for effect on inhibiting Lin-28 and/or Lin-28B or reducing a symptom of cancer or abnormal proliferation. For example, one can use both an in vivo animal model of cancer or in vitro models of cancer, which are commonly known to persons of ordinary skill in the art.

In some embodiments, in vitro models can be used to determine the effective doses of the inhibitor agents of Lin-28 and/or Lin-28B to knock down Lin-28 and/or Lin-28B expression by the methods as disclosed herein as a cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models are also useful to determine the effect of an inhibitor agent of Lin-28 and/or Lin-28B for the treatment and/or prevention of cancer using the methods as disclosed herein, and are the preferred models to determine the effective doses of Lin-28 and/or Lin-28B inhibitors for use as cancer treatments using the methods as disclosed herein. Suitable in vivo models include, but are not limited to, mice that carry a mutation in the KRAS oncogene (Lox-Stop-Lox K-RasGi2D mutants, Kras24TYj) available from the National Cancer Institute (NCI) Frederick Mouse Repository. Other mouse models known in the art and that are available include but are not limited to models for breast cancer, gastrointestinal cancer, hematopoietic cancer, lung cancer, mammary gland cancer, nervous system cancer, ovarian cancer, prostate cancer, skin cancer, cervical cancer, oral cancer, and sarcoma cancer (see the world-wide-web at //emice.nci.nih. gov/mouse_models/).

Animals administered an agent inhibiting Lin-28 and/or Lin-28B as disclosed herein can be evaluated for symptoms relative to animals not administered agents inhibiting Lin-28. A measurable change in the severity a symptom (i.e., a decrease in at least one symptom, i.e. 10% or greater decrease), or a delay in the onset of a symptom, in animals treated with an inhibitor of Lin-28 and/or Lin-28B versus untreated animals is indicative of therapeutic efficacy.

Use of Agents that Inhibit Lin-28

In some embodiments, the method as disclosed herein are useful for the treatment of any disease or disorder characterized by lack or reduced expression of tumor suppressor miR-NAs, for example but not limited to let-7 family miRNA.

In alternative embodiments, the methods as disclosed herein are useful for the treatment of any disease or disorder characterized by increased of Lin-28 and/or Lin-28B as compared to a reference level. In some embodiments, the subject is assessed if they have increased level of Lin-28 and/or Lin-28B in a biological sample from the subject as compared to a reference level of Lin-28 and/or Lin-28B in a reference biological sample, and such subjects where the level of Lin-28 and/or Lin-28B in a biological sample is greater than the reference level are amenable to administration of Lin-28 and/or Lin-28B inhibitors as disclosed herein.

In alternative embodiments, the methods as disclosed herein are useful for the treatment of any disease or disorder characterized by a decrease in let-7 miRNA as compared to a reference level. In some embodiments, the subject is assessed if they have decreased level of let-7 miRNA in a biological sample from the subject as compared to a reference level of let-7 miRNA in a reference biological sample, and such subjects where the level of let-7 miRNA in a biological sample is lower than the reference level are amenable to administration of Lin-28 and/or Lin-28B inhibitors as disclosed herein.

In some embodiments, the biological sample obtained from the subject is from a biopsy tissue sample, and in some embodiments, the sample is from a tumor or cancer tissue sample. The level of Lin-28 and/or Lin-28B or let-7 can be determined by methods known by the skilled artisan, for example by northern blot analysis or RT-PCR, or using the methods as disclosed in the methods section of the Examples.

In some embodiments, the disease is cancer. In some embodiments, the cancer comprise a population of cancer stem cells. Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness.

In some embodiments, a pharmaceutical composition as disclosed herein comprises at least one agent which is an inhibitor of Lin-28 and/or Lin-28B and can be used for the treatment of adult and/or pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In one embodiment, a pharmaceutical composition as disclosed herein comprises at least one agent which is an inhibitor of Lin-28 and/or Lin-28B can be administered for treatment or prevention of breast cancer. In some embodiments, the pharmaceutical composition as disclosed herein which comprises at least one agent inhibitor of Lin-28 and/or Lin-28B can be administered for treatment or prevention of, for example but not limited to; lung cancer, hepatic cancer or leukemia, for example but not limited to lung carcinoma, chronic myelogenous leukemia (CML) and HCC (hepatic cell carcinoma). I In addition, the agents and pharmaceutical compositions as disclosed herein comprising inhibitors of Lin-28 and/or Lin-28B can also be used for prophylactic treatment of cancer. There are hereditary conditions and/or environmental situations (e.g. exposure to carcinogens) known in the art that predispose an individual to developing cancers, or subjects identified to have increased expression of Lin-28 and/or Lin-28B as compared to a reference sample. Under these circumstances, it may be beneficial to treat these individuals with therapeutically effective doses of an agent which inhibit Lin-28 and/or Lin-28B to reduce the risk of developing cancers.

In one embodiment, the agents and pharmaceutical compositions as disclosed herein comprising inhibitors of Lin-28 and/or Lin-28B are useful to be administered to a subject who has cancer regression. In another embodiment, the agents and pharmaceutical compositions as disclosed herein comprising inhibitors of Lin-28 and/or Lin-28B are useful to be administered to a subject who has a therapy-resistant cancer, for example a chemotherapy resistant cancer. In some embodiments, the agents and pharmaceutical compositions as disclosed herein comprising inhibitors of Lin-28 and/or Lin-28B are useful to be administered to a subject who has cancer and has been exposed to adjuvant cancer therapies.

In another embodiment, the agents and pharmaceutical compositions as disclosed herein comprising inhibitors of Lin-28 and/or Lin-28B are useful to be administered to a subject with a malignant cancer. In some embodiments, the agents and pharmaceutical compositions as disclosed herein comprising inhibitors of Lin-28 and/or Lin-28B are also useful to be administered to and for the treatment of a subject with a cancer or tumor comprising a cancer stem cell.

Most therapeutic strategies for cancer are aimed at reducing or eliminating the tumor or tumor. In some embodiments, agents that inhibit Lin-28 and/or Lin-28B as disclosed herein are also useful in the treatment of other disease or disorders associated with abnormal cellular proliferation or differentiation of stem cells. Thus, treatment can be directed to a subject who is affected but asymptomatic with cancer, for example, a disease of an organ or tissue in a subject characterized by poorly controlled or uncontrolled multiplication of normal or abnormal cells in that tissue and its effect on the body as a whole. Cancer diseases which can be treated or prevented by inhibitors of Lin-28 and/or Lin-28B as disclosed herein include, for example but are not limited to, benign neoplasms, dysplasias, hyperplasias as well as neoplasms showing metastatic growth or any other transformations like e.g. leukoplakias which often precede a breakout of cancer.

To determine efficacy of an agent that inhibits Lin-28 and/or Lin-28B for the treatment and/or prevention of cancer, the determination of a baseline value of a cancer biomarker as disclosed herein is useful, or the baseline level of Lin-28 or Lin-28B expression before administering a dosage of agent, and comparing this with a value for cancer biomarker or level of Lin-28/Lin-28B in a biological before and after treatment. A decrease, for example a 10% decrease in the level Lin-28 or Lin-28B expression or protein indicates a positive treatment outcome (i.e., that administration of the agent has achieved or augmented a decrease in Lin-28). If the value for level of expression of Lin-28 or Lin-28B in the biological sample does not significantly change, or increases, a negative treatment outcome is indicated. In general, subjects undergoing an initial course of treatment with an agent are expected to show a decrease in Lin-28 and/or Lin-28B with successive dosages of an agent as described herein.

In other methods to determine efficacy of treatment, a reference value (i.e. a control value or a mean and standard deviation) of Lin-28 or Lin-28B is determined for a control population. Typically the individuals in the control population have not received prior treatment and do not suffer from cancer or abnormal proliferation. Measured values of Lin-28 and/or Lin-28B in a biological sample from a subject after administering an inhibitor agent of Lin-28/Lin-28 as disclosed herein are then compared with a reference level. A decrease in the level of Lin-28/Lin-28B in the biological sample from the subject relative to the reference level (i.e. a decrease of at least 10% of Lin-28/Lin-28B in a subject) signals a positive treatment outcome. A lack of significant decrease signals a negative treatment outcome.

In one embodiment, the subject is assessed if they are at risk of having a metastasis or malignant cancer, the method comprising assessing a level of Lin-28 or Lin-28B in a biological sample, and if the levels of Lin-28 or Lin-28B in a biological sample in the subject are above a reference level of Lin-28 or Lin-28B, the subject is at risk of having a metastasis or a malignant cancer. In some embodiments, the biological sample is obtained from a biopsy tissue sample, and in some embodiments, the sample is from a tumor or cancer tissue sample. The level of Lin-28 or Lin-28B can be determined by methods known by the skilled artisan, for example by northern blot analysis or RT-PCR. In some embodiments, the reference level is the level of Lin-28 or Lin-28B that does not result in malignancy or a malignant cancer. In some embodiments, the reference level the based on the level of Lin-28 or Lin-28B expression in a normal tissue sample, where in the tissue sample is a biological tissue sample from a tissue matched, and species matched and age matched biological sample. In some embodiments, the reference level is based on a reference sample is from a non-malignant matched tissue sample. In some embodiments, the reference level is based on a reference sample from a non-stem cell cancer tissue sample.

In other methods, a reference level of Lin-28 or Lin-28B is determined from a control population of subjects who have undergone treatment with a therapeutic agent that is effective at reducing the cancer biomarker or reducing level or expression Lin-28 or Lin-28B. Measured levels of Lin-28 or Lin-28B in the subject are compared with the reference level.

In another embodiment, the present invention provides methods to determine whether a resumption of cancer treatment is required. For example, a subject who is not presently receiving treatment by an agent which inhibits Lin-28 or Lin-28B is disclosed herein but where the subject has undergone a previous course of treatment can be monitored for level or expression or activity of Lin-28 or Lin-28B. The measured level of Lin-28 or Lin-28B a biological sample from the subject at a second timepoint can be compared with the reference level of Lin-28 or Lin-28B measured at earlier timepoint (i.e. a first timepoint) which can be, for example the level of Lin-28 or Lin-28B previously measured in a biological sample obtained from the subject after a previous course of treatment. A significant decrease in level of Lin-28 or Lin-28B relative to the previous measurement (i.e., a decrease of at least 10%) is an indication that treatment is effective. Alternatively, the level of Lin-28 or Lin-28B in a biological sample from the subject can be compared with a reference level of Lin-28 or Lin-28B from a population of subjects after undergoing a course of treatment. Alternatively, the level of Lin-28 or Lin-28B in a biological sample from a subject can be compared with a reference level in populations of prophylactically treated subjects who remain free of symptoms of disease, in particular free of symptoms of cancer or abnormal cellular proliferation.

In some embodiments, the agents and pharmaceutical compositions as disclosed herein comprising at least one inhibitor of Lin-28 or Lin-28B can be administered in therapeutically effective dosages alone or in combination with at least one other adjuvant cancer therapy such as surgery, chemotherapy, radiotherapy, thermotherapy, immunotherapy, hormone therapy, anti-cancer agent or laser therapy, to provide a beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer.

The term "anti-cancer agent" or "anti-cancer drug" is any agent, compound or entity that would be capably of negatively affecting the cancer in the subject, for example killing cancer cells, inducing apoptosis in cancer cells, reducing the growth rate of cancer cells, reducing the number of mestatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. Anti-cancer therapy includes biological agents (biotherapy), chemotherapy agents, and radiotherapy agents. The combination of chemotherapy with biological therapy is known as biochemotherapy.

In one embodiment, an anti-cancer treatment is a let-7 miRNA. Accordingly, the present invention encompasses the administration of at least one agent inhibitor of Lin-28 and/or Lin-28B with a let-7 miRNA, where administration of an agent inhibitor of Lin-28 and/or Lin-28B the can be concurrent, or sequential or alternating to the administration of a let-7 miRNA. Accordingly, the present invention provides methods to promote the efficacy of a let-7 miRNA as a therapeutic agent by suppressing Lin-28-mediated let-7 miRNA inhibition.

Cancer therapy can also include prophylaxis, including agents which slow or reduce the risk of cancer in a subject. In other embodiments, a cancer therapy is any treatment or any means to prevent the proliferation of cells with abnormal proliferation or cancerous cells. In some embodiments, then anti-cancer treatment is an agent which suppresses the EGF-EGFR pathway, for example but not limited to inhibitors and agents of EGFR. Inhibitors of EGFR include, but are not limited to, tyrosine kinase inhibitors such as quinazolines, such as PID 153035, 4-(3-chloroanilino)quinazoline, or CP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines (Traxler et al., (1996) J. Med Chem 39:2285-2292), curcumin (diferuloyl methane) (Laxmin arayana, et al., (1995), Carcinogen 16:1741-1745), 4,5-bis (4-fluoroanilino)phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO05/018677 (Wyeth); W099/09016 (American Cyanamid); W098/43960 (American Cyanamid); WO 98/14451; WO 98/02434; W097/38983 (Warener Labert); W099/06378 (Warner Lambert); W099/06396 (Warner Lambert); W096/30347 (Pfizer, Inc.); W096/33978 (Zeneca); W096/33977 (Zeneca); and W096/33980 (Zeneca), WO 95/19970; U.S. Pat. App. Nos. 2005/0101618 assigned to Pfizer, 2005/0101617, 20050090500 assigned to OSI Pharmaceuticals, Inc.; all herein incorporated by reference. Further useful EGFR inhibitors are described in U.S. Pat. App. No. 20040127470, particularly in tables 10, 11, and 12, and are herein incorporated by reference.

In another embodiment, the anti-cancer therapy includes a chemotherapeutic regimen further comprises radiation therapy. In an alternate embodiment, the therapy comprises administration of an anti-EGFR antibody or biological equivalent thereof.

In some embodiments, the anti cancer treatment comprises the administration of a chemotherapeutic drug selected from the group consisting of fluoropyrimidine (e.g., 5-FU), oxaliplatin, CPT-11, (e.g., irinotecan) a platinum drug or an anti EGFR antibody, such as the cetuximab antibody or a combination of such therapies, alone or in combination with surgical resection of the tumor. In yet a further aspect, the treatment compresses radiation therapy and/or surgical resection of the tumor masses. In one embodiment, the present invention encompasses administering to a subject identified as having, or increased risk of developing RCC an anti-cancer combination therapy where combinations of anti-cancer agents are used, such as for example Taxol, cyclophosphamide, cisplatin, gancyclovir and the like. Anti-cancer therapies are well known in the art and are encompassed for use in the methods of the present invention. Chemotherapy includes, but is not limited to an alkylating agent, mitotic inhibitor, antibiotic, or antimetabolite, anti-angiogenic agents etc. The chemotherapy can comprise administration of CPT-11, temozolomide, or a platin compound. Radiotherapy can include, for example, x-ray irradiation, w-irradiation, γ-irradiation, or microwaves.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cisplatinum, methotrexate, and alkaloids such as vindesine and vinblastine.

In another embodiment, the present invention encompasses combination therapy in which subjects identified as having, or increased risk of developing cancer by having increased levels of Lin-28 protein or expression as compared to a reference level using the methods as disclosed herein are administered an anti-cancer combination therapy where combinations of anti-cancer agents are used are used in combination with cytostatic agents, anti-VEGF and/or p53 reactivation agent. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics include inhibitors of matrix metalloproteinases such as marimastat, growth factor antagonists, signal transduction inhibitors and protein kinase C inhibitors.

Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog #F1028), an angio-inhibitory compound secreted by *Aspergillus fumigates*.

As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æterna Zentaris Inc; Quebec City, Calif.) and combinations thereof.

The compositions as disclosed herein used in connection with the treatment methods of the present invention are administered and dosed in accordance with good medical practice, taking into account the clinical condition of the individual subject, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art.

The methods of the present invention are useful for the early detection of subjects susceptible to developing cancers by detecting an increased level of Lin-28 or Lin-28 expression or protein as compared to a reference level. Thus, treatment may be initiated early, e.g. before or at the beginning of the onset of symptoms, for example before the onset of cancer. In alternative embodiments, the treatment may be administered to a subject that has, or is at risk of developing cancer. In alternative embodiments, the treatment may be administered prior to, during, concurrent or post the development of cancer. The effective amount or dosage required at these early stages will typically be lower than those needed at later stages of disease where the symptoms of cancer are severe. Such dosages are known to those of skill in the art and can be determined by a physician.

Methods to Identify Subjects at Risk of Cancer

The inventors have also discovered a method to identify subject having an increased likelihood of developing or having cancer. In some embodiments, the method comprises measuring the level of the expression or activity of Lin-28 in a biological sample obtained from the subject, for example measuring protein expression or gene expression, where the level is compared to a reference level and if the expression or activity level of Lin-28 is higher than the expression or activity of a reference level, the subject is identified as having an increased likelihood of developing cancer.

In some embodiments, a reference level of Lin-28 and/or Lin-28B the based on the level of Lin-28 and/or Lin-28B expression or protein activity in a normal tissue sample, where in the tissue sample is a biological tissue sample from a tissue matched, species matched and age matched biological sample. In some embodiments, a reference level of and/or Lin-28B is based on a biological sample is from a non-malignant matched tissue sample. In some embodiments, the reference level of and/or Lin-28B is based on a biological sample from a non-stem cell cancer tissue sample.

Formulations of Compositions

An agent which inhibits Lin-28 and/or Lin-28B as disclosed herein, can be used as a medicament or used to formulate a pharmaceutical composition with one or more of the utilities disclosed herein. In some embodiments, an agent which inhibits Lin-28 and/or Lin-28B can be administered in vitro to cells in culture, in vivo to cells in the body, or ex vivo to cells outside of an individual that can later be returned to the body of the same individual or another. Such cells can be disaggregated or provided as solid tissue.

In some embodiments, an agent which inhibits Lin-28 and/or Lin-28B as disclosed herein can be used to produce a medicament or other pharmaceutical compositions. Use of the compositions as disclosed herein comprising an agent inhibiting Lin-28 and/or Lin-28 can further comprise a pharmaceutically acceptable carrier and/or additional components useful for delivering the composition to a subject. Such pharmaceutically acceptable carrier and/or additional components are well known in the art. Addition of such carriers and other components to the agents as disclosed herein is well within the level of skill in this art.

Pharmaceutical compositions can be administered as a formulation adapted for passage through the blood-brain barrier or direct contact with the endothelium. In some embodiments, the compositions may be administered as a formulation adapted for systemic delivery. In some embodiments, the compositions may be administered as a formulation adapted for delivery to specific organs, for example but not limited to the liver, bone marrow, or systemic delivery.

Alternatively, pharmaceutical compositions can be added to the culture medium of cells ex vivo. In addition to the active compound, such compositions can contain pharmaceutically-acceptable carriers and other ingredients known to facilitate administration and/or enhance uptake (e.g., saline, dimethyl sulfoxide, lipid, polymer, affinity-based cell specific-targeting systems). The composition can be incorporated in a gel, sponge, or other permeable matrix (e.g., formed as pellets or a disk) and placed in proximity to the endothelium for sustained, local release. The composition can be administered in a single dose or in multiple doses which are administered at different times.

Pharmaceutical compositions can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration can be made with the goals of achieving a favorable response in the subject with cancer, for example a subject with cancer or a subject at risk thereof (i.e., efficacy), and avoiding undue toxicity or other harm thereto (i.e., safety). Therefore, "effective" refers to such choices that involve routine manipulation of conditions to achieve a desired effect.

A bolus of the formulation administered to an individual over a short time once a day is a convenient dosing schedule. Alternatively, the effective daily dose can be divided into multiple doses for purposes of administration, for example, two to twelve doses per day. Dosage levels of active agents or ingredients in a pharmaceutical composition can also be varied so as to achieve a transient or sustained concentration of the compound or derivative thereof in an individual, especially in and around vascular endothelium of the brain, and to result in the desired therapeutic response or protection. But it is also within the skill of the art to start doses at levels lower than required to achieve the desired therapeutic effect and to gradually increase the dosage until the desired effect is achieved.

The amount of an agent inhibiting Lin-28 and/or Lin-28B to be administered to a subject is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

The term "treatment", with respect to treatment of a subject with cancer or risk of developing cancer refers to, inter alia, preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is free therefrom as well as slowing or reducing progression of existing disease. For a given subject, improvement in a symptom, its worsening, regression, or progression can be determined by an objective or subjective measure. Reduction of tumor size or attenuation of tumor size increase or modification of one or more biochemical markers for cancer, for example but not limited to, CD44, telomerase, TGF-α, TGF, erbB-2, erbB-3, MUC1, MUC2, CK20, PSA, CA125, FOBT can be measured.

In some embodiments, efficacy of treatment can also be measured as an improvement or beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer. In alternative embodiments, efficacy of treatment can be measured as an improvement in morbidity or mortality (e.g., lengthening of survival curve for a selected population). Prophylactic methods (e.g., preventing or reducing the incidence of relapse) are also considered treatment In some embodiments, treatment can also involve combination with other existing modes of treatment, for example existing agents for treatment of cancer, or other anti-cancer agents, for example but are not limited to other cancer therapies such as surgery, chemotherapy, radiotherapy, thermotherapy, immunotherapy, hormone therapy, administration of anti-cancer agents or laser therapy, to provide a beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer.

In some embodiments, agents that inhibit Lin-28 and/or Lin-28B as disclosed herein can be combined with other agent, for example therapeutic agent to prevent and/or treat cancer. Such agents can be any agent currently in use or being developed for the treatment and/or prevention of cancer, where the agent can have a prophylactic and/or a curative effect and/or reduce a symptom of a cancer.

In embodiments where an inhibitor agent of Lin-28 and/or Lin-28B as disclosed herein is used for the prevention and/or treatment of cancer, an inhibitor agent of Lin-28/Lin28B can be used in combination with medicaments commonly known by person of ordinary skill in the art that are claimed to be useful as symptomatic treatments of cancer. Examples of such medicaments are disclosed and are referred to as anticancer agents herein, and include, but are not limited to, temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cis-platinum, methotrexate, and alkaloids such as vindesine and vinblastine.

In some embodiments, an inhibitor agent of Lin-28/Lin28B can be used in combination with a let-7 miRNA. Thus, combination treatment with one or more agents that inhibit Lin-28/Lin-28B with one or more other medical procedures can also be practiced.

In addition some embodiments, the methods and compositions as disclosed herein can comprise multiple agents to inhibit Lin-28 expression or activity. For example, the multiple agents can be selected from a variety of agents, such as for example, use of nucleic acids, nucleic acid analogues, peptides, phage, phagemids, polypeptides, peptidomimetics, ribosomes, aptamers, antibodies, small or large organic or inorganic molecules, or any combination thereof which inhibit Lin-28 and/or Lin-28B. In some embodiments, agents useful in methods of the present invention include agents that function as nucleic acid inhibitors of Lin-28/Lin-28B expression, such as for example inhibitors of Lin-28 mRNA. For example, as the 3'UTR of the Lin-28 gene comprises target sequences or target sites for transcriptional regression by let-7, lin-4 and miR-125a miRNAs. Since expression of Lin-28 is negatively regulated by let-7 family members, lin-4 and miR-125a, use of antagoimers (anti-miRNA oligonucleotides which silence endogenous miRNAs) to let-7 family members, lin-4 and miR-125a are useful in the methods and compositions as disclosed herein to inhibit the expression of Lin-28.

The amount of the pharmaceutical composition comprising an agent inhibitor of Lin-28 and/or Lin-28B is preferably administered to a subject in an amount that does not induce toxic effects which outweigh the advantages which result from its administration. Further objectives are to reduce in number, diminish in severity, and/or otherwise relieve suffering from the symptoms of the disease in the individual in comparison to recognized standards of care.

Production of the compositions according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results aimed at agents that inhibit Lin-28 and/or Lin-28B expression and/or activity can vary. Thus, minimum and maximum effective dosages vary depending on the method of administration. Suppression of the clinical and histological changes of cancer can occur within a specific dosage range, which, however, varies depending on the organism receiving the dosage, the route of administration, whether an agent inhibitor of Lin-28/Lin-28B is administered in conjunction with other co-stimulatory molecules, and the specific regimen of inhibitor of Lin-28/Lin-28B administration. For example, in general, nasal administration requires a smaller dosage than oral, enteral, rectal, or vaginal administration.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

Examples of solid carriers include starch, sugar, bentonite, silica, and other commonly used carriers. Further non-limiting examples of carriers and diluents which can be used in the formulations of the present invention include saline, syrup, dextrose, and water.

Administration

In one aspect, the invention provides a method of administering any agent inhibitors of Lin-28 and/or Lin-28B as disclosed herein to a subject. When administered, agent inhibitors of Lin-28 and/or Lin-28B are applied in a therapeutically effective, pharmaceutically acceptable amount as a pharmaceutically acceptable formulation. As used herein, the term "pharmaceutically acceptable" is given its ordinary meaning. Pharmaceutically acceptable compounds are generally compatible with other materials of the formulation and are not generally deleterious to the subject. Any of the compositions of the present invention may be administered to the subject in a therapeutically effective dose. A "therapeutically effective" or an "effective" as used herein means that amount necessary to delay the onset of, inhibit the progression of, halt altogether the onset or progression of, diagnose a particular condition being treated, or otherwise achieve a medically desirable result, i.e., the amount which is capable of at least partially preventing, reversing, reducing, decreasing, ameliorating, or otherwise suppressing the particular condition being treated.

A therapeutically effective amount can be determined on an individual basis and will be based, at least in part, on consideration of the species of mammal, the mammal's age, sex, size, and health; the compound and/or composition used, the type of delivery system used; the time of administration relative to the severity of the disease; and whether a single, multiple, or controlled-release dose regiment is employed. A therapeutically effective amount can be determined by one of ordinary skill in the art employing such factors and using no more than routine experimentation.

The terms "treat," "treated," "treating," and the like, when used herein, refer to administration of the systems and methods of the invention to a subject, which may, for example, increase the resistance of the subject to development or further development of cancers, to administration of the composition in order to eliminate or at least control a cancer, and/or to reduce the severity of the cancer. When administered to a subject, effective amounts will depend on the particular condition being treated and the desired outcome. A therapeutically effective dose may be determined by those of ordinary skill in the art, for instance, employing factors such as those further described below and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parental administration, in some cases, may be from one to several orders of magnitude lower dose per day, as compared to oral doses. For example, the dosage of an active compound when parentally administered may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day. In some embodiments, the concentration of the active compound(s), if administered systemically, is at a dose of about 1.0 mg to about 2000 mg for an adult of kg body weight, per day. In other embodiments, the dose is about 10 mg to about 1000 mg/70 kg/day. In yet other embodiments, the dose is about 100 mg to about 500 mg/70 kg/day. Preferably, the concentration, if applied topically, is about 0.1 mg to about 500 mg/gm of ointment or other base, more preferably about 1.0 mg to about 100 mg/gm of base, and most preferably, about 30 mg to about 70 mg/gm of base. The −25 specific concentration partially depends upon the particular composition used, as some are more effective than others. The dosage concentration of the composition actually administered is dependent at least in part upon the particular physiological response being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously affect the mammal. The dosage can be determined by one of ordinary skill in the art employing such factors and using no more than routine experimentation. In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels within the subject or within the active site of the subject. In some cases, dosing amounts, dosing schedules, routes of administration, and the like may be selected as described herein, whereby therapeutically effective levels for the treatment of cancer are provided.

In certain embodiments where cancers are being treated, agent inhibitors of Lin-28 and/or Lin-28B as disclosed herein can be administered to a subject who has a family history of cancer, or to a subject who has a genetic predisposition for cancer, for example breast cancer. In other embodiments, agent inhibitors of Lin-28 and/or Lin-28B as disclosed herein can be administered to a subject who has reached a particular age, or to a subject more likely to get cancer. In yet other embodiments, agent inhibitors of Lin-28 and/or Lin-28B as disclosed herein are administered to subjects who exhibit symptoms of cancer (e.g., early or advanced). In still other embodiments, the composition may be administered to a subject as a preventive measure.

In some embodiments, the agent inhibitors of Lin-28 and/or Lin-28B as disclosed herein are administered to a subject based on demographics or epidemiological studies, or to a subject in a particular field or career. In some embodiments, agent inhibitors of Lin-28 and/or Lin-28B as disclosed herein are administered to a subject that has had a prior therapy, for example cancer therapy. Examples of such therapies are, but not limited to, surgery, chemotherapy, radiotherapy, thermotherapy, immunotherapy, hormone therapy and laser therapy.

Administration of agent inhibitors of Lin-28 and/or Lin-28B as disclosed herein to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects.

Where agent inhibitors of Lin-28 and/or Lin-28B is a nucleic acid agent, methods to deliver such nucleic acid agent inhibitors of Lin-28 and/or Lin-28B to the cell or subject are well known in the art, and include chemical transfection using lipid-based, amine based and polymer based techniques, viral vectors and can combinations thereof (see, for example, products from Ambion Inc., Austin, Tex.; and Novagen, EMD Biosciences, Inc, an Affiliate of Merck KGaA, Darmstadt, Germany).

Other described ways to deliver nucleic acid agent inhibitors of Lin-28 and/or Lin-28B is from vectors, such as lentiviral constructs, and introducing siRNA molecules into cells using electroporation. However, feline FIV lentivirus vectors which are based on the feline immunodeficiency virus (FIV) retrovirus and the HIV lentivirus vector system, which is base on the human immunodeficiency virus (HIV), carry with them problems related to permanent integration. Electroporation is also useful in the present invention, although is generally only used to deliver siRNAs into cells in vitro.

The target cell types, to which nucleic acid agent inhibitors of Lin-28 and/or Lin-28B can be delivered include eukaryotic cells including, but not limited to hepatocytes, myocytes, neural cells, lipocytes, lymphocytes, macrophages, cardiac cells, endothelial cells, epithelial cells, and the like. In one embodiment, the target cell type is a tumor cell or a cancer cell including, but not limited to lung cancer cell, retinal cancer cell, breast cancer cell, ovarian cancer cell, prostate cancer cell, head and neck cancer cell, lymphoma cell, melanoma cell, glioma cell, bladder cancer cell, genital-urinary cancer cell, stomach cancer cell, pancreatic cancer cell, liver cancer cell, kidney cancer cell, HCC cell, gastrointestinal cancer and the like. In some embodiment, the target cells are cancer stem cells. In alternative embodiments, the target cells are selected from the group consisting of human lymphocytes, human dendritic cells, human adult stem cells, cancer stem cells and embryonic stem cells.

In one embodiment, nucleic acid agent inhibitors of Lin-28 and/or Lin-28B can be present in a vector. These vectors include a sequence encoding nucleic acid agent inhibitors of Lin-28 and/or Lin-28B and in vivo expression elements.

In some embodiments, agent inhibitors of Lin-28 and/or Lin-28B as disclosed herein can be delivered in vivo and in vitro. The in vivo delivery as used herein means delivery of agent inhibitors of Lin-28 and/or Lin-28B as disclosed herein into a living subject, including human. The in vitro delivery as used herein means delivery of agent inhibitors of Lin-28 and/or Lin-28B as disclosed herein into cells and organs outside a living subject.

Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; marine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include rekoviruses, the life cycle of which involves reverse transcription of genomic viral RNA into DNA with subsequent proviral integration into host cellular DNA.

Retroviruses have been approved for human gene therapy trials. Genetically altered retroviral expression vectors have general utility for the high efficiency transduction of nucleic acids in viva. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular L Biology," vol. 7, Humana Press, Inc., Cliffton, N.J. (1991).

In some embodiments the "in vivo expression elements" are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter and/or a tissue specific promoter. Examples of which are well known to one of ordinary skill in the art. Constitutive mammalian promoters include, but are not limited to, polymerase promoters as well as the promoters for the following genes: hypoxanthine phosphoribosyl transferase (HPTR), adenosine deaminase, pyruvate kinase, and beta.-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydroylase (CYP-7) promoter, beta-galactosidase alpha-2,6 sialylkansferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamma enolase (neuron-specific enolase, NSE) promoter. Exemplary tissue-specific expression elements for the brain include, but are not limited to, the neurofilament heavy chain (NF-H) promoter. Exemplary tissue-specific expression elements for lymphocytes include, but are not limited to, the human CGL-1/granzyme B promoter, the terminal deoxy transferase (TdT), lambda 5, VpreB, and 1ck (lymphocyte specific tyrosine protein kinase p561ck) promoter, the humans CD2 promoter and its 3' transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter.

In some embodiments, tissue-specific expression elements for breast cells are for example, but are not limited to, the human alpha-lactalbumin promoter. Exemplary tissue-specific expression elements for the lung include, but are not limited to, the cystic fibrosis transmembrane conductance regulator (CFTR) gene promoter.

Other elements aiding specificity of expression in a tissue of interest can include secretion leader sequences, enhancers, nuclear localization signals, endosmolytic peptides, etc. Preferably, these elements are derived from the tissue of interest to aid specificity. In general, the in vivo expression element shall include, as necessary, 5' non-transcribing and 5' non-translating sequences involved with the initiation of transcription. They optionally include enhancer sequences or upstream activator sequences.

In some embodiments, nucleic acid agent inhibitors of Lin-28 and/or Lin-28B as disclosed herein can be expressed as a viral vector and can be delivered using any delivery system such as topical administration, subcutaneous, intramuscular, intraperitoneal, intrathecal and intravenous injections, catheters for delivering an agent inhibitor of Lin-28/Lin28-B as disclosed herein into, for example, a specific organ, such as breast, brain, liver, heart or kidneys, or into, for example, a specific location having a cancer or cancer stem cell, and/or affected with malignant growth or cancer. In some embodiments, an agent inhibitor of Lin-28 and/or Lin-28B as disclosed herein can be complexed to a targeting moiety to target the agent to a cancer cell. Such a targeting moiety can be, for example, an antibody which recognizes and bind with specific affinity to a cell surface receptor on a cancer cell. Such cell surface markers are well known in the art and are encompassed for use herein.

The "pharmaceutically acceptable carrier" means any pharmaceutically acceptable means to mix and/or deliver agent inhibitors of Lin-28 and/or Lin-28B as disclosed herein, either alone or complexed to targeting moieties to a subject. In some embodiments, for clinical use, an agent inhibitor of Lin-28 and/or Lin-28B as disclosed herein can be formulated into pharmaceutical formulations or compositions for oral, rectal, vaginal, parenteral, topical, intravenous or other mode of administration. The pharmaceutical formulation contains at least one agent inhibitor of Lin-28 and/or Lin-28B as disclosed herein in combination with one or more pharmaceutically acceptable ingredients. The carrier may be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration.

In the preparation of pharmaceutical formulations or compositions containing an agent inhibitor of Lin-28/Lin-28B as disclosed herein in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention in vegetable oil, fat, or other suitable vehicle for soft gelatin capsules. Hard gelatin capsules may contain granules of the active compound. Hard gelatin capsules may also contain an agent inhibitor of Lin-28/Lin-28B as disclosed herein in combination with solid powdered ingredients such as lactose, saccharose, sorbitol, mannitol, potato starch, corn starch, arnylopectin, cellulose derivatives or gelatin.

Dosage units for rectal or vaginal administration may be prepared (i) in the form of suppositories which contain the active substance, i.e. an agent inhibitor of Lin-28 and/or Lin-28B as disclosed herein mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The methods of the present invention to also encompass delivery an agent inhibitor of Lin-28 and/or Lin-28B as disclosed herein orally in granular form including sprayed dried particles, or complexed to form micro or nanoparticles.

The subject or individual as referred to herein and throughout the specification includes mammals, such as murine, specifically mice and rats, bovine, and primates, such as human.

Any medically acceptable method may be used to administer a composition to the subject. The administration may be localized (i.e., to a particular region, physiological system, tissue, organ, or cell type) or systemic, depending on the condition being treated. For example, an agent inhibitor of Lin-28 and/or Lin-28B as disclosed herein can be administered orally, vaginally, rectally, buccally, pulmonary, topically, nasally, transdermally, through parenteral injection or implantation, via surgical administration, or any other method of administration where suitable access to a target is achieved. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred in some embodiments because of the convenience to the subject as well as the dosing schedule. Compositions suitable for oral administration may be presented as discrete units such as hard or soft capsules, pills, cachettes, tablets, troches, or lozenges, each containing a predetermined amount of an agent inhibitor of Lin-28 and/or Lin-28B.

Other oral agent inhibitor of Lin-28 and/or Lin-28B as disclosed herein for use with the invention include solutions or suspensions in aqueous or non-aqueous liquids such as a syrup, an elixir, or an emulsion. In another set of embodiments, an agent inhibitor of Lin-28 and/or Lin-28B as disclosed herein may be used to fortify a food or a beverage.

Injections can be e.g., intravenous, intratumoral, intradermal, subcutaneous, intramuscular, or interperitoneal. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

In some embodiments, an agent inhibitor of Lin-28 and/or Lin-28B as disclosed herein can be administered which enables tissue-specific uptake of the agent. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

In further embodiments, an agent inhibitor of Lin-28 and/or Lin-28B as disclosed herein can also be delivered using a bioerodible or bioresorbable implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, lo hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), i poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic; acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and 2s hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules, (1993) i 26:581-587, the teachings of which are incorporated herein, polyhyaluronic acids, casein, gelatin, glutin, polyanhydrides, polyacrylic acid, alginate, chitosan, poly(methyl I methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In certain embodiments of the invention, the administration of an agent inhibitor of Lin-28 and/or Lin-28B as disclosed herein can be designed so as to result in sequential exposures to the composition over a certain time period, for example, hours, days, weeks, months or years. This may be accomplished, for example, by repeated administrations of an agent inhibitor of Lin-28 and/or Lin-28B as disclosed herein by one of the methods described above, or by a sustained or controlled release delivery system in which an agent inhibitor of Lin-28 and/or Lin-28B is delivered over a prolonged period without repeated administrations. Administration of an agent inhibitor of Lin-28 and/or Lin-28B using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time release, delayed release, sustained release, or controlled release delivery systems. Such systems may avoid repeated administrations in many cases, increasing convenience to; the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neuka1 fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and 295,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, s the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Examples of systems in which release occurs in bursts includes, e. g., systems in which the composition is entrapped in liposomes which are encapsulated in a polymer matrix, the liposomes being sensitive to specific stimuli, e.g., temperature, pH, light or a degrading enzyme and systems in which the composition is encapsulated by a tonically-coated microcapsule with a microcapsule core degrading enzyme. Examples of systems in which release of the inhibitor is gradual and continuous include, e.g., erosional Is systems in which the composition is contained in a forth within a matrix and effusional systems in which the composition permeates at a controlled rate, e.g., through a polymer. Such sustained release systems can be e.g., in the form of pellets, or capsules.

Examples of systems in which release occurs in bursts includes, e. g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an tonically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some; embodiments of the invention. "Long-term release," as used herein, means that the implant containing an agent inhibitor of Lin-28 and/or Lin-28B as disclosed herein are constructed and arranged to deliver therapeutically effective levels of the composition for at least 30 or 45 days, and preferably at least 60 or days, or even longer in some cases. Long-term release implants are well known to those of ordinary skill in the art, and include some of the release systems described above.

As In some embodiments, an agent inhibitor of Lin-28 and/or Lin-28B as disclosed herein can include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients, include diluents such as calcium carbonate, sodium carbonate, lactose, kaolin, calcium I phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric lo acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and; emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or all-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, so sterile, fixed oils are conventionally employed as a solvent or suspending medium. For i this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. Those of skill in the art can readily determine the various parameters for preparing and formulating the compositions of the invention without resort to undue experimentation.

In some embodiments, a pharmaceutical composition comprising an agent inhibitor of Lin-28 and/or Lin-28B as disclosed herein can comprise a suitable carrier, and optionally comprise one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product. In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as; alkaline metal salts, such as lithium, sodium, or potassium salts, or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorus acids and the like.

Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the agent inhibitor of Lin-28 and/or Lin-28B employed and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more nucleic acids are optionally tested in one or more appropriate in vitro and/or in viva animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the $LD_{50}$ of the relevant formulation, and/or observation of any side-effects of the nucleic acids at various concentrations, e.g., as applied to the mass and overall health of the patient. Administration can be accomplished via single or divided doses.

The dose administered to a 70 kilogram subject is typically in the range equivalent to dosages of currently-used therapeutic antisense oligonucleotides such as Vikavene (fomivirsen sodium injection) which is approved by the FDA for treatment of cytomegaloviral RNA, adjusted for the altered activity or serum half-life of the relevant composition.

In some embodiments, an agent inhibitor of Lin-28 and/or Lin-28B as disclosed herein can supplement the treatment of any known additional therapy, including, but not limited to, antibody administration, vaccine administration, administration of cytotoxic agents, natural amino acid polypeptides, nucleic acids, nucleotide analogues, and biologic response modifiers. In some embodiments, additional therapy is, for example, surgery, chemotherapy, radiotherapy, thermotherapy, immunotherapy, hormone therapy and laser therapy. In some embodiments, the additional therapy is chemotherapy. Two or more combined compounds may be used together or sequentially with an agent inhibitor of Lin-28 and/or Lin-28B as disclosed herein. An agent inhibitor of Lin-28 and/or Lin-28B can be administered before the additional therapy, after the additional therapy or at the same time as the additional therapy. In some embodiments, an agent inhibitor of Lin-28 and/or Lin-28B can also be administered a plurality of times, and in other embodiments, the additional therapies are also administered a plurality of times.

In some embodiments, an agent inhibitor of Lin-28 and/or Lin-28B as disclosed herein can also be administered in therapeutically effective amounts as a portion of an anti-cancer cocktail. An anti-cancer cocktail is mixture, for example of a least one agent inhibitor of Lin-28 and/or Lin-28B with one or more anti-cancer agents in addition to a pharmaceutically acceptable carrier for delivery. The use of anti-cancer cocktails as a cancer treatment is routine. Anti-cancer agents that are well known in the art and can be used as a treatment in combination with an agent inhibitor of Lin-28 and/or Lin-28B as disclosed herein include, but are not limited to: let-7 miRNA, Actinomycin D, Aminoglutethimide, Asparaginase, Bleomycin, Busulfan, Carboplatin, Carmustine, Chlorambucil, Cisplatin (cis-DDP), Cyclophospharnide, Cytarabine HCl (Cytosine arabinoside), Dacarbazine, Dactinomycin, Daunorubicin HCl, Doxorubicin HCl, Estramustine phosphate sodium, Etoposide (V16-213), Flosuridine, S-Fluorouracil (5-Fu), Flutamide, Hydroxyurea (hydroxycarb amide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Ockeotide, Paclitaxel; Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate, and analogues thereof.

In certain embodiments, the pharmaceutical compositions comprising a an agent inhibitor of Lin-28 and/or Lin-28B as disclosed herein can optionally further comprise one or more additional therapies or agents. In certain embodiments, the additional agent or agents are anti-cancer agents. In some embodiments, the therapeutic agents are chemotherapeutic agents, for example cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

Enteric Coated Formulation.

As regards formulations for administering the small chemical entities for an agent inhibitor of Lin-28 and/or Lin-28B, one particularly useful embodiment is a tablet formulation comprising an agent inhibitor of Lin-28 and/or Lin-28B with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-, 3,4-diepoxybutane. The casing can also include starch and/or dextrin.

Preferred enteric coating materials are the commercially available EUDRAGIT® enteric polymers such as EUDRAGIT® L, EUDRAGIT® S and EUDRAGIT® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX® or CITROFLEX® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In that example, lactose monohydrate, microcrystalline cellulose, the active ingredient, the hydroxypropyl methyl cellulose and half of the croscarmellose sodium were screened into a 10 Liter Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric-coated preparations of this sort can be prepared by one skilled in the art, using these materials or their equivalents.

The present invention may be defined in any of the following numbered paragraphs:

1. A method for promoting miRNA processing of pri-miRNA to mature miRNA in a cell, the method comprising contacting a cell with at least one agent which inhibits the activity or expression of Lin-28 polypeptide or a variant or homologue thereof.
2. The method of paragraph 1, wherein the cell is a cancer cell.
3. The method of paragraph 1, wherein the cancer cell is a cancer cell line.
4. The method of paragraph 1, wherein the cell is a human cell.
5. The method of paragraph 1, wherein the cell is in vitro, in vivo, in a subject or ex vivo.
6. The method of paragraph 1, wherein the mature miRNA is a member of the let-7 miRNA family.
7. The method of paragraph 1, wherein the mature miRNA is a tumor suppressor miRNA.
8. The method of paragraph 1, wherein the agent is selected from the group consisting of: a small molecule, nucleic acid, nucleic acid analogue, aptamer, ribosome, peptide, protein, antibody, or variants and fragments thereof.
9. The method of paragraph 1, wherein the cancer cell is s selected from the group consisting of: a breast cancer cell, a lung cancer cell, a head and neck cancer cell, a bladder cancer cell, a stomach cancer cell, a nervous system cancer cell, a bone cancer cell, a bone marrow cancer cell, a brain cancer cell, a colon cancer cell, a colorectal cancer cell, a esophageal cancer cell, a endometrial cancer cell, a gastrointestinal cancer cell, a genital-urinary cancer cell, a stomach cancer cell, a lymphomas cell, a melanoma cell, a glioma cell, a bladder cancer cell, a pancreatic cancer cell, a gum cancer cell, a kidney cancer cell, a retinal cancer cell, a liver cancer cell, a nasopharynx cancer cell, an ovarian cancer cell, an oral cancer cell, a bladder cancer cell, a hematological neoplasm cell, a follicular lymphoma cell, a cervical cancer cell, a multiple myeloma cell, a B-cell chronic lymphcylic leukemia cell, a B-cell lymphoma cell, an osteosarcoma cell, a thyroid cancer cell, a prostate cancer cell, a colon cancer cell, a prostate cancer cell, a skin cancer cell, a stomach cancer cell, a testis cancer cell, a tongue cancer cell and an uterine cancer cell.

10. The method of paragraph 1, wherein the cancer cell is a breast cancer cell or lung cancer cell.

11. The method of paragraph 1, wherein the cancer cell is a lung adrenocarcinoma cell or a chronic myelogenous leukemia (CML) cell.

12. The method of paragraph 1, wherein the cancer cell is a pre-cancer cell, a malignant cancer cell, a therapy resistant cancer cell or a cancer stem cell.

13. A method of treating or preventing a cancer in a subject, comprising administering to a subject a pharmaceutical composition comprising an effective amount of at least one agent that inhibits the activity and/or expression of Lin-28.

14. The method of paragraph 13, wherein the subject is identified to have, or be at risk of an increase in the level of expression and/or activity of Lin-28 or Lin-28B in a biological sample obtained from the subject as compared to a reference level.

15. The method of paragraphs 13 or 14, wherein the subject is identified to have, or be at risk of a reduction of the level or expression and/or activity, or loss of expression of a tumor suppressor miRNA in a biological sample as compared to a reference level.

16. The method of paragraph 15, wherein the tumor suppressor miRNA is a member of the let-7 miRNA family.

17. The method of paragraph 15, wherein the tumor suppressor miRNA is selected from the group consisting of: miR-16-1, miR-143 and miR-145.

18. The method of any of the paragraphs 13 to 17, wherein the cancer is selected from the group consisting of breast cancer, lung cancer, head and neck cancer, bladder cancer, stomach cancer, cancer of the nervous system, bone cancer, bone marrow cancer, brain cancer, colon cancer, colorectal cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, B-cell chronic lymphcylic leukemia, B-cell lymphoma, osteosarcomas, thyroid cancer, prostate cancer, colon cancer, prostate cancer, skin cancer, stomach cancer, testis cancer, tongue cancer, or uterine cancer.

19. The method of any of the paragraphs 13 to 18, wherein the cancer is breast cancer or lung cancer.

20. The method of any of the paragraphs 13 to 18, wherein the cancer cell is a lung adrenocarcinoma cell or a chronic myelogenous leukemia (CML) cell.

21. The method of any of the paragraphs 13 to 18, wherein the cancer is a pre-cancer, malignant cancer, therapy resistant cancer or a cancer comprising cancer stem cells.

22. The method of paragraph 13, wherein the agent is selected from the group consisting of: a small molecule, nucleic acid, nucleic acid analogue, aptamer, ribosome, peptide, protein, antibody, or variants and fragments thereof.

23. The method of paragraphs 13 or 22, wherein the antibody is a recombinant antibody, humanized antibody, chimeric antibody, modified antibody, monoclonal antibody, polyclonal antibody, miniantibody, dimeric miniantibody, minibody, diabody or tribody or variants, analogues or modified versions thereof.

24. The method of paragraphs 13 or 22, wherein the agent is DNA, RNA, nucleic acid analogue, peptide nucleic acid (PNA), pseudo-complementary PNA (pcPNA), locked nucleic acid (LNA), antagomir or analogue thereof.

25. The method of any of paragraphs 13 to 22, wherein the agent is a small inhibitory RNA (RNAi), siRNA, microRNA, shRNA, miRNA and analogues and homologues and variants thereof.

26. The method of any of paragraphs 1 to 25, wherein the agent comprises nucleic acids of an SEQ ID NO:7, 8 or 9.

27. The method of any of paragraphs 1 to 26, wherein the agent binds to the let-7 target site in the 3'UTR of Lin-28.

28. The method of paragraph 13, wherein administering is intravenous, intradermal, intramuscular, intraarterial, intralesional, percutaneous, subcutaneous, or by aerosol.

29. The method of paragraph 13, further comprising administering to the subject one or more additional therapies.

30. The method of paragraph 29, wherein additional therapies are selected from the group consisting of surgery, chemotherapy, radiotherapy, thermotherapy, immunotherapy, hormone therapy or laser therapy.

31. The method of any of the paragraphs 13 to 30, wherein the subject is a human.

32. Use of an agent which inhibits the expression and/or activity of Lin-28 protein for the preparation of a medicament for the treatment and/or prevention of a cancer or malignancy, wherein the cancer or malignancy is characterized by the reduction in level of, or loss of a tumor suppressor miRNA.

33. The use of an agent of paragraph 32, wherein the tumor suppressor miRNA is a member of the let-7 miRNA family.

34. The use of an agent of paragraph 32, wherein the subject is identified to have, or be at risk of an increase in the level of expression and/or activity of Lin-28 or Lin-28B in a biological sample obtained from the subject as compared to a reference level.

35. The use of an agent of paragraph 32, wherein the tumor suppressor miRNA is a member of the let-7 miRNA family.

36. The use of an agent of paragraph 32, wherein the tumor suppressor miRNA is selected from the group consisting of: miR-16-1, miR-143 and miR-145.

37. The use of an agent of paragraph 32, wherein the cancer is selected from the group consisting of: breast cancer, lung cancer, head and neck cancer, bladder cancer, stomach cancer, cancer of the nervous system, bone cancer, bone marrow cancer, brain cancer, colon cancer, colorectal cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, B-cell chronic lymphcylic leukemia, B-cell lymphoma, osteosarcomas, thyroid cancer, prostate cancer, colon cancer, prostate cancer, skin cancer, stomach cancer, testis cancer, tongue cancer and uterine cancer.
38. The use of an agent of paragraph 32, wherein the cancer is a breast cancer or a lung cancer.
39. The use of an agent of paragraph 32, wherein the cancer is a pre-cancer, malignant cancer, therapy resistant cancer or a cancer comprising cancer stem cells.
40. The use of an agent of paragraph 32, wherein the cancer is lung adrenocarcinoma cell or chronic myelogenous leukemia (CML).
41. The use of an agent of paragraph 32, wherein the agent is selected from the group consisting of: a small molecule, nucleic acid, nucleic acid analogue, aptamer, ribosome, peptide, protein, antibody, or variants and fragments thereof.
42. The use of an agent of paragraph 41, wherein the antibody is a recombinant antibody, humanized antibody, chimeric antibody, modified antibody, monoclonal antibody, polyclonal antibody, miniantibody, dimeric miniantibody, minibody, diabody or tribody or variants, analogues or modified versions thereof.
43. The use of an agent of paragraph 41, wherein the agent is DNA, RNA, nucleic acid analogue, peptide nucleic acid (PNA), pseudo-complementary PNA (pcPNA), locked nucleic acid (LNA), antagomir or analogue thereof.
44. The use of an agent of paragraph 41, wherein the agent is a small inhibitory RNA (RNAi), siRNA, microRNA, shRNA, miRNA and analogues and homologues and variants thereof.
45. The use of an agent of paragraph 41, wherein the agent comprises nucleic acids of an SEQ ID NO:7, 8 or 9.
46. The use of an agent of paragraph 32, wherein the agent binds to the let-7 target site in the 3'UTR of Lin-28.
47. The use of an agent of paragraph 32, wherein the subject is a human.
48. A method for identifying a subject having increased likelihood of developing or having cancer, the methods comprising measuring the level of the expression or activity of Lin-28 of a variant thereof in a biological sample obtained from the subject, wherein if the expression or activity level of Lin-28 is higher than the expression or activity of a reference level, the subject is identified as having an increased likelihood of developing cancer.
49. The method of paragraph 48, wherein the variant of Lin-28 is Lin-28B.
50. The method of paragraph 48, wherein the biological sample is serum plasma, blood or tissue sample.
51. The method of paragraph 48, wherein the biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample and primary ascite sample.
52. The method of paragraph 48, wherein the biological sample is selected from the group consistent of blood, plasma, serum, urine, spinal fluid, plural fluid, nipple aspirates, lymph fluid, external secretions of the skin, respiratory, internal and genitoururinary tracts, bile, tears, sweat, siliva, organs, milk cells and primary ascite cells.
53. The method of paragraph 49, wherein the tissue sample is a biopsy tissue sample.
54. The method of paragraph 48, wherein the biological sample is a cancer biopsy tissue sample.
55. The method of paragraph 48, wherein the biological sample is a in vitro or ex vivo cultivated biopsy tissue sample.
56. The method of paragraph 48, wherein measuring is measuring the level of gene transcript expression or mRNA expression of Lin-28.
57. The method of paragraph 48, wherein measuring is measuring the level of protein expression of Lin-28.
58. The method of paragraph 48, wherein measuring is measuring the level of protein activity of Lin-28.
59. The method of paragraphs 48 or 56, wherein measuring protein expression is by a method selected from the group consisting of; immunoblot analysis, immunohistochemical analysis; ELISA, isoform-specific chemical or enzymatic cleavage, protein array or mass spectrometry.
60. The method of paragraphs 48, 55 or 57, wherein protein expression is measured by contacting the biological sample with at least one protein binding agent selected from the group consisting of; antibodies; recombinant antibodies, chimeric antibodies, tribodies, midibodies, protein-binding agents, small molecule, recombinant protein, peptides, aptamers, avimers and derivatives or fragments thereof.
61. The method of paragraph 54, wherein measuring gene expression is by methods selected from the group comprising; reverse-transcription polymerase chain reaction (RT-PCR) or by quantitative RT-PCR (QRT-PCR) reaction.
62. The method of paragraphs 48, wherein the cancer is selected from a group consisting of; gastrointestinal cancer, prostate cancer, ovarian cancer, breast cancer, squamous cell carcinomas (SCC), head and neck cancer, lung cancer, non-small cell lung cancer, cancer of the nervous system, brain cancer, bone-marrow cancer, bone cancer, kidney cancer, retina cancer, skin cancer, bladder cancer, colon cancer, esophageal cancer, testicular cancer, leukemia, lymphoma, melanoma, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer.
63. The method of paragraphs 48, wherein the cancer is breast cancer is a triple-negative subtype breast cancer; or a cancer which lacks the expression of estrogen receptor (ER), the progesterone receptor (PR) and lacks Her-2 expression.
64. The method of paragraph 48, wherein the cancer is lung adrenocarcinoma cell or chronic myelogenous leukemia (CML).
65. A method for preventing the development of cancer in a subject, the method comprising assessing the risk of a subject to develop cancer according to the method of paragraph 48, wherein the clinician directs a subject to be treated with an appropriate anti-cancer therapy if the subject is at risk of developing cancer.
66. A method for treating cancer in a subject, the method comprising measuring the level of the expression or activity of Lin-28 in a biological sample obtained from the subject, wherein a clinician reviews the results and if the expression or activity level of Lin-28 is higher than the expression or activity of a reference level, the clinician directs the subject to be treated with an anti-cancer therapy and/or a pharmaceutical composition comprising an effective amount of at least one agent that inhibits the activity and/or expression of Lin-28 according to paragraphs 13-31.

EXAMPLES

The examples presented herein relate to the methods and compositions for the prevention and/or treatment of cancer or malignancy by inhibition of Lin-28. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Plasmids and Cloning.

Full-length mouse Lin-28 cDNA was purchased from Open Biosystems. The open reading frame was subcloned into pETDuet (Novagen) for bacterial expression. Pri-miRNA substrates were amplified from CD-1 mouse genomic DNA and cloned into the PCR-4-Topo vector (Invitrogen) for direct use in in vitro transcription. For transfection experiments, pri-miRNAs were subcloned into pcDNA3.

Cell Culture and Transfection.

ES cell culture and embryoid body differentiation were as described[20]. P19 cells were cultured in αMEM supplemented with 10% FCS. Transient transfections were performed using Lipofectamine 2000 (Invitrogen) per manufacturer's instructions.

Northern Blotting.

20 μg total RNA from each sample was used for Northern blotting as previously described[4]. Probes for miRNA detection were antisense, end-labeled DNA oligonucleotides to the mature miRNA sequence.

In vitro Processing Assays.

Processing reactions were performed as described previously[1]. 10,000 cpm pri-miRNA was pre-incubated on ice with cell extracts or rLin-28 for 60 min. Flag-Drosha IP was then added and processing reaction was performed at 37° C. for 90 min. Samples were resolved on a 15% TBE-Urea gel and visualized by autoradiography.

Affinity Purification.

Synthetic pre-let-7g (Dharmacon) was conjugated to agarose beads and incubated with 30 mg of P19 whole cell extract as described[21]. After pull-down, eluate was subjected to SDS-PAGE, followed by colloidal blue staining and mass spectroscopic sequencing of bands. Recombinant His-Lin-28 was expressed in BL-21 E. coli and purified by standard procedures.

RNA Interference.

pLKO.1-shRNA plasmids targeting Lin-28 were from the Broad-TRC collection (Sigma-Aldrich). TRC numbers for hairpins used are: sh1 (TRCN0000102575) (SEQ ID NO:7), sh2 (TRCN0000102578) (SEQ ID NO:8), and sh3 (TRCN0000102579) (SEQ ID NO:9). For knockdown experiments, 1 μg shRNA plasmid or control shRNA plasmid targeting GFP was transiently transfected into P19 cells. Total RNA was collected at 60 hours post-transfection. Knockdown was quantitated by quantitative PCR for Lin-28 with beta-actin as an internal standard. Primer sequences are available in Table 2.

TABLE 2

Primer Sequences for RT-PCR and quantitative PCR.

| Primer Name | Sequence | Comment |
|---|---|---|
| Let-7gF | GTACGGTGTGGACCTCATCA (SEQ ID NO: 1) | For amplification of pri-let-7g as described in ref. 5 |
| Let-7gR | TCTTGCTGTGTCCAGGAAAG (SEQ ID NO: 2) | For amplification of pri-let-7g as described in ref. 5 |
| ActinF | CAGAAGGAGATTACT GCTCTGGCT (SEQ ID NO: 3) | |
| ActinR | TACTCCTGCTTGCTG ATCCACATC (SEQ ID NO: 4) | |
| Lin28qPCRF | AGGCGGTGGAGTTCACCTTTAAGA (SEQ ID NO: 5) | |
| Lin28qPCRR | AGCTTGCATTCCTTGGCATGATGG (SEQ ID NO: 6) | |

Plasmids and Cloning.

Full-length mouse Lin-28, hnRNPA1, hnRNPL, and Msi-2 cDNAs were purchased from Open Biosystems and open reading frames were subcloned into pFlag-CMV2. Lin-28 was subcloned into pETDuet (Novagen) for bacterial expression. Pri-let-7g and pri-miR-15a/16-1 substrates were amplified from CD-1 mouse genomic DNA and cloned into the PCR-4-Topo vector (Invitrogen) for direct use in in vitro transcription. For transfection experiments, pri-miRNAs were subcloned into pcDNA3.

ES Cell Culture and Transfection.

ES cell culture and embryoid body differentiation were as described in Gregory, et al. (Nature 432, 235-240 (2004) which is incorporated herein in its entirety by reference). P19 cells were cultured in αMEM supplemented with 10% FCS. Transient transfections were performed using Lipofectamine 2000 (Invitrogen) per manufacturer's instructions. Flag-tagged proteins were produced by transient transfection of 293T cells.

Cell Line Culture.

Cell lines were originally obtained from ATCC and cultured under standard conditions. BaF3/AblG2A and Baf3/SrcY530F lines have been described elsewhere (Azam, M., Seeliger, M. A., Gray, N. S., Kuriyan, J., & Daley, G. Q. Nat. Struct. Mol. Biol. (2008), which is incorporated in its entirety herein by reference). LKR cells were derived from a mouse adenocarcinoma (Johnson, L. et al. Nature 410, 1111-1116 (2001) which is incorporated in its entirety herein by reference).

Quantitative PCR.

Quantitative RT-PCR was used for detection of mature miR species as described previously in Viswanathan et al., (Science 320, 97-100 (2008) which is incorporated in its entirety herein by reference). Levels of mature miRNA species were measured by quantitative PCR using commercially available Taqman probes (Applied Biosystems) per manufacturer's instructions with sno142 RNA or U47 RNA used as an internal standards for normalization. Quantitative PCR of gene expression was done using SYBR green using beta-actin as an internal standard for normalization. Relative fold changes were calculated using the ΔΔCt method (Gregory et al., Nature 432, 235-240 (2004) and Denli, et al., Nature 432, 231-235 (2004)).

Northern Blotting.

20 μg total RNA from each sample was used for Northern blotting as previously described (Chendrimada et al., Nature 436, 740-744 (2005)). Probes for miRNA detection were antisense, end-labeled DNA oligonucleotides to the mature miRNA sequence.

RNA Gel-Shift Assay.

RNA Gel-shift assays were conducted using 2×105 cpm end-labeled pre-let-7g probe, 1.5 μg cell extract, and 100 pmol cold pre-let-7g competitor. Binding reactions were conducted in 10 μl total volume with 160 ng tRNA competitor and 5 μg/μl heparin. Binding buffer contained 60 mM KCl, 10 mM HEPES, pH 7.6, 3 mM MgCl2, 5% glycerol, and 1 mM DTT. RNA-protein complexes were resolved on native 5% polyacrylamide gels.

In Vitro Processing Assays.

Processing reactions were performed as described previously (4). 10,000 cpm pri-miRNA was pre-incubated on ice with cell extracts, rLin-28, or Flag-immunoprecipitates for 60 min. Flag-Drosha IP was then added and processing reaction was performed at 37° C. for 90 min. Samples were resolved on a 15% TBE-Urea gel and visualized by autoradiography.

Affinity Purification.

Synthetic pre-let-7g (Dharmacon) was conjugated to agarose beads and incubated with 30 mg of P19 whole cell extract as described (Obernosterer, et al., RNA 12, 1161-1167 (2006)). After pull-down, eluate was subjected to SDS-PAGE, followed by colloidal blue staining and mass spectroscopic sequencing of bands. Recombinant His-Lin-28 was expressed in BL-21 *E. coli* and purified by standard procedures (Gregory, et al., Cell 123, 631-640 (2005).

RNA Interference.

pLKO.1-shRNA plasmids targeting Lin-28 were from the Broad-TRC collection (Sigma-Aldrich). TRC numbers for hairpins used are: sh1 (TRCN0000102575), sh2 (TRCN0000102578), and sh3 (TRCN0000102579). The sequence of Lin-28 siRNA was as previously described (Lin-28 SI-2) (Mineno et al., Nucl. Acids Res. 34, 1765-1771 (2006)). For knockdown experiments, 1 μg shRNA plasmid or control shRNA plasmid targeting GFP was transiently transfected into P19 cells. Total RNA was collected at 60 hours post-transfection. Knockdown was quantitated by quantitative PCR for Lin-28 with beta-actin as an internal standard. Primer sequences are available in Table 3. Protein knockdown was also verified by immunoblotting using anti-Lin-28 antibody (R&D).

TABLE 3

Primer Sequences

| Primer Name | Sequence | Comment |
| --- | --- | --- |
| Let-7gF | GTACGGTGTGGACCTCATCA (SEQ ID NO: 1) | For amplification of pri-let-7g as described in ref. (5) |
| Let-7gR | TCTTGCTGTGTCCAGGAAAG (SEQ ID NO: 2) | For amplification of pri-let-7g as described in ref. (5) |
| ActinF | CAGAAGGAGATTACTGCTCTGGCT (SEQ ID NO: 3) | RT-PCR Primers |
| ActinR | TACTCCTGCTTGCTGATCCACATC (SEQ ID NO: 4) | RT-PCR Primers |
| Lin28qPCRF | AGGCGGTGGAGTTCACCTTTAAGA (SEQ ID NO: 5) | RT-PCR Primers |
| Lin28qPCRR | AGCTTGCATTCCTTGGCATGATGG (SEQ ID NO: 6) | RT-PCR Primers |
| IVPlet7gF | CTCCAAATATGGTAAAGATGAGGCAAATGTGTGG (SEQ ID NO: 20) | For detection and cloning of pri-let-7g |

TABLE 3-continued

Primer Sequences

| Primer Name | Sequence | Comment |
|---|---|---|
| IVPlet7gR | GACAACCACAATGCATTTCTG GTTATTCTAGTGCC (SEQ ID NO: 21) | For detection and cloning of pri-let-7g |
| IVP15a/16-1F | GGAAATACTTTTTATTCTGCTG AAAGCCTATAAAATTATGC (SEQ ID NO: 22) | For cloning of pri-miR-15a/16-1 |
| IVP15a/16-1R | GTATTGCCAACCTTACTTCAGC AGCACAGTCAATACTGG (SEQ ID NO: 23) | For cloning of pri-miR-15a/16-1 |

Antibodies.

The following antibodies were used for immunoblotting: c-myc (Santa Cruz, sc-764), KRas (Santa Cruz, sc-30), Abl-K12 (Santa Cruz, sc-131), c-Src (Cell Signaling, #2110). Anti-lin28 (Proteintech group) was used for immunohistochemistry.

Cloning and Plasmid Construction.

Mouse Lin28 cDNA was subcloned into pBabe.Puro and pMSCV.Neo retroviral vectors. pMSCV.Neo.let-7g construct was previously described (Kumar, M. S., et al., Nat. Genet. 39, 673-677 (2007) which is incorporated in its entirety herein by reference.) Lin28B shRNA in lentiviral plasmid was purchased from Sigma-Aldrich (TRCN0000122599). Control shRNA was commercially purchased (SHC002V, Sigma-Aldrich)

Immunohistochemistry.

Sections of tissues were deparaffinized with xylene and rehydrated with graded series of ethanol (absolute, 95%, 80% and 50%, respectively, and distilled water), followed by two washes of 5 min each in PBS-T. Antigen retrieval for 20 min in sodium citrate buffer (10 mM pH 6) at 90-100 C. Wash with PBST 1×5 min. Tissue sections were then incubated for 10 min in 3% (v/v) hydrogen peroxide in methanol to block endogenous peroxidase activity. Sections were then washed for 5 min in PBS-T and blocked at room temperature for 1 h by using 2% normal goat serum, 2% bovine serum albumin (BSA) and 0.1% triton-X in PBS. Tissue sections were then incubated in humidified chamber for overnight incubation at 4° C. with primary antibody (1/200 in TBST). Sections were subsequently washed with PBS-T (3×5 min) and incubated at room temperature for 1 h with secondary antibody (goat anti rabbit). After a wash with PBS-T (3×5 min), sections were incubated with ready to use streptavidin peroxidase (Lab Vision, Fremont, Calif.) for 10 min at room temperature and then color was developed by using a DAB kit (Vector laboratories, Burlingame, Calif.). Sections were counterstained with hematoxylin.

Viral Production.

For ecotropic viral production, retroviral plasmid DNA and pCL-Eco were transfected into 293T cells in a 1:1 mass ratio and virus harvested after 48 h. For VSV-G pseudotyped lentivirus, viral plasmid, lentiviral gag/pol, and VSV-G were transfected in a ratio 1:0.9:0.1, and virus was harvested after 72 hrs. 1 mL of unconcentrated viral supernatant was used to infect 50,000 cells. Infected cells were selected on antibiotic for a minimum of 48 hrs prior to subsequent analysis.

Transformation and Growth Assays.

Soft agar assays and were performed as described previously with 50,000 cells seeded per well. Colonies were stained with 0.005% crystal violet and counted after 21 d of growth (Lee, J. C. et al. PLoS. Med. 3, e485 (2006)).

Microarray Data Analysis.

The following are Gene expression Omnibus accession numbers for analyzed microarray datasets: GSE11024, GSE6222, GSE9843, GSE3218, GSE9891. $Log_2$ transformed expression data were normalized to the average expression signal for normal tissue (where available), or row-normalized for the GSE9843 and GSE9891 datasets. Cutoff for over-expression was taken as a normalized expression value of 2 or greater.

Electromobility Shift Assays (EMSA).

EMSA was conducted using ~$2\times10^5$ cpm 5'-end-labeled pre-miRNA probe, together with the indicated amounts of competitor RNA and recombinant Lin28 that was prepared as described previously (Viswanathan et al., (2008) Science 320, 97-10018). Binding reactions were conducted in 20 µl of total volume with 30 µg of yeast tRNA. Binding buffer contained 100 mM NaCl, 50 mM Tris (pH 7.6), 5% glycerol, 20 units of RnaseOUT, and 10 mM β-mercaptoethanol. Bound complexes were resolved on native 5% polyacrylamide gels. Band intensities of scanned gels were quantified using Adobe PhotoShop software. The data were fitted to a hyperbolic function of the nonlinear curve fitting method of GraphPad Prism. The total amount of probe in each binding reaction was normalized against the unbound probe (in the absence of recombinant Lin28 protein (rLin28)) and used to calculate the fraction bound by rLin28. Dissociation constants of pre-let-7g and the let-7g terminal loop were derived from a fit to the equation: Fraction bound=$B_{max}$([rLin28])/(Kd % [rLin28]), where $B_{max}$ represents the observed maximum fraction of probe bound, [rLin28] represents protein concentration, and Kd is the dissociation constant.

Quantitative PCR and Mutagenesis.

Levels of mature miRNA species were measured by quantitative PCR using commercially available TaqMan probes (Applied Biosystems) per the manufacturer's instructions with sno142 RNA or U47 RNA used as internal standards for normalization. The plasmid for expression of let-7g loop/miR-21 was generated using the QuikChange kit (Stratagene) and the following primers to amplify from the pcDNA3-pri-let-7g plasmid: forward, 5'-CTGAGGTAGTAGTTTGTA-CAGTTCTGTTGAATCTCATGGACTGTACAGGCCAC TGCCTTG-3' (SEQ ID NO: 24), and reverse, 5'-CAAG-GCAGTGGCCTGTACAGTCCATGAGAT-TCAACAGAACTGTACAAACTAC TACCTCAG-3' SEQ ID NO: 25). Plasmids for the expression of the Lin28 proteins containing single amino acid substitutions were generated by site-directed mutagenesis of the pCMV2-Lin28 using the QuikChange kit (Stratagene).

Northern Blotting.

20 μg of total RNA from each sample was used for Northern blotting as described previously (Viswanathan et al., (2008) Science 320, 97-10018). Probes for miRNA detection were antisense, end-labeled DNA oligonucleotides to the mature miRNA sequence.

Example 1

Figure 1B:
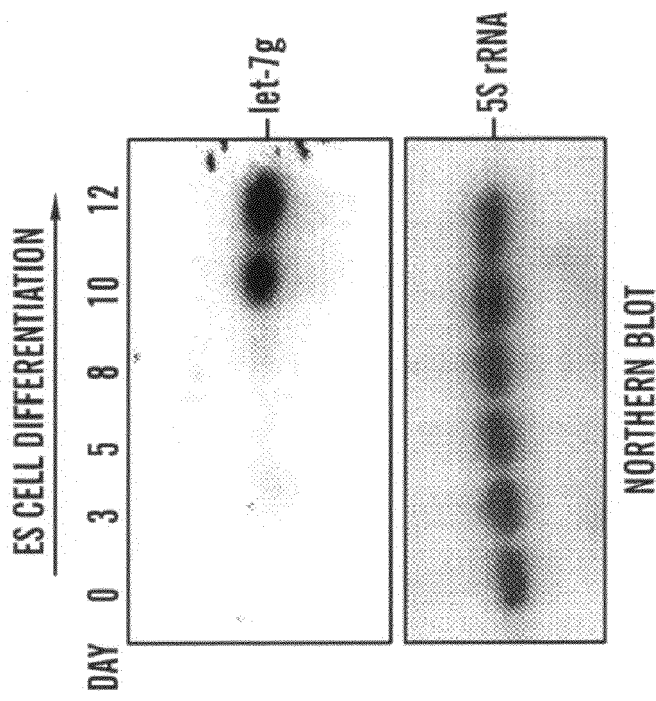
FIG. 1 shows post-transcriptional control of pri-let-7g processing. a, RT-PCR for pri-let-7g transcript (as described in ref. 5) during ES differentiation to embryoid bodies. b, Northern blot showing mature let-7g induction during embryoid body formation. c, in vitro pri-miRNA processing reaction using radiolabelled pri-let-7g as substrate. Pri-miRNA was preincubated with various amounts of P19 cell extract (left), ES extract (middle), or mouse embryonic fibroblast (MEF)
Figure 1A:
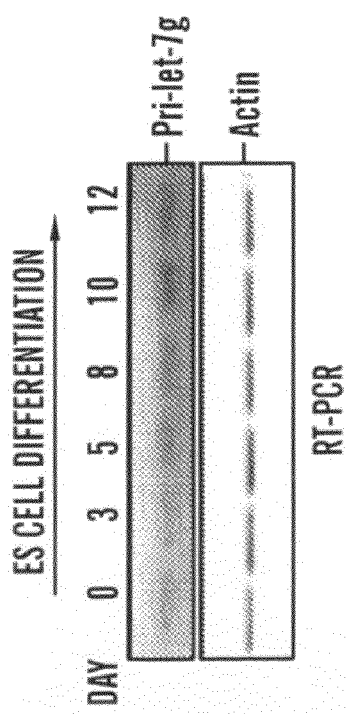

The inventors investigated the biogenesis of let-7 family of miRNAs in ES and EC cells. The inventors demonstrate that pri-let-7g transcript is readily detectable in ES and EC cells and remains at relatively constant levels over the course of differentiation (FIG. 1a). In contrast, mature let-7g is undetectable in undifferentiated EC and ES cells but upregulated several thousand-fold as differentiation proceeds[5] (FIG. 1b). A post-transcriptional induction of let-7g expression has also been reported during the differentiation of P19 EC cells with retinoic acid[5].

Figure 1C:
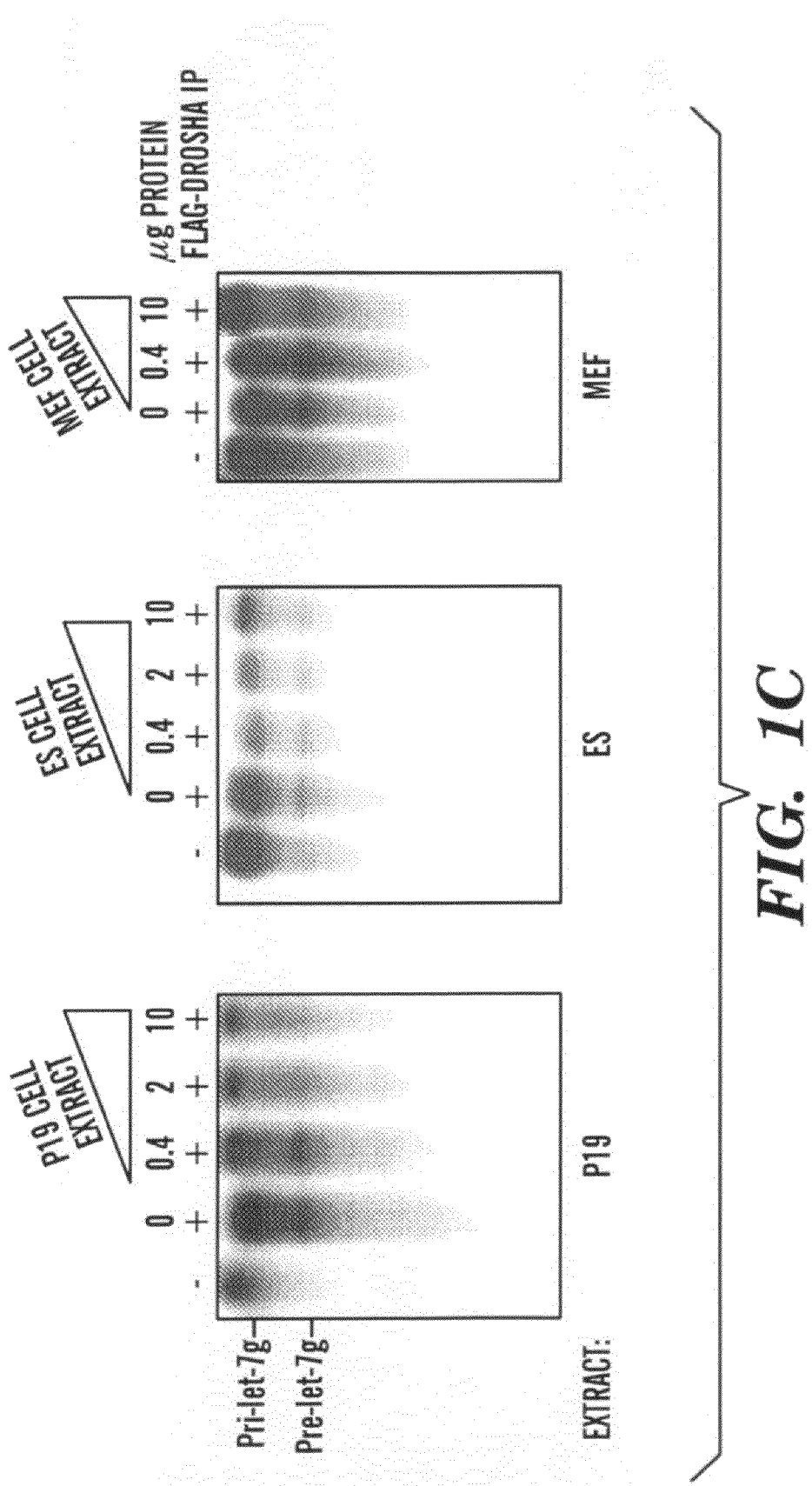

In order to understand the mechanism for the post-transcriptional block in miRNA processing in EC and ES cells, the inventors first compared cell extracts from different cell types for their ability to inhibit Drosha-mediated cleavage of pri-miRNA substrates to the corresponding pre-miRNAs in vitro (FIG. 1c). Radiolabeled pri-miRNA substrates were preincubated with cell extract and subsequently subjected to processing by affinity-purified Drosha complex. While extracts from undifferentiated ES and P19 cells readily inhibited Drosha-mediated cleavage of pri-let-7g to pre-let-7g, cell extracts from differentiated mouse embryonic fibroblasts (MEFs) did not inhibit cleavage. HeLa cell extracts also had no inhibitory activity in this assay (data not shown). Thus, the specificity of the in vivo Drosha processing block is recapitulated in this in vitro assay.

The inventors identify and demonstrate that a protein factor or factors present in ES and EC cells inhibits Drosha-mediated processing of pri-miRNAs by employing a biochemical approach. Using gel-shift assays with a labeled pre-let-7g probe enabled the inventors to identify a specific band shift present with P19 and ES extract, but not with MEF extract (data not shown), demonstrating that pre-let-7g could be used as an effective affinity reagent for purification of the factor(s) responsible for the Drosha processing block. Pre-let-7g was conjugated to agarose beads and incubated with whole cell extract from P19 cells. The affinity eluate was subjected to SDS-polyacrylamide electrophoresis (PAGE) followed by colloidal staining. Bands were excised and subjected to mass spectroscopic sequencing in three segments (FIG. 5). Sequencing revealed a number of RNA-binding proteins co-purifying with pre-let-7g. Interestingly, a number of these proteins were previously identified as members of a large Drosha-containing protein complex[1] (FIG. 5).

The inventors identified that one of the pre-let-7g-interacting proteins was the small, highly-conserved RNA-binding protein, Lin-28. The inventors further investigated the role of Lin-28 in inhibition of processing of pri-miRNAs, as Lin-28 has the following: 1) mutations within its RNA-binding domain have been shown to impair developmental timing regulation in C. elegans[9]; 2) it is expressed specifically in undifferentiated P19 cells, mouse ES cells[10], and human ES cells[11], and down-regulated upon differentiation; and 3) a mammalian Lin-28 homologue, Lin-28 B, is overexpressed in hepatocellular carcinoma, and overexpression of this gene promotes cancer cell proliferation in vitro[12].

Figures 2A, 2B:
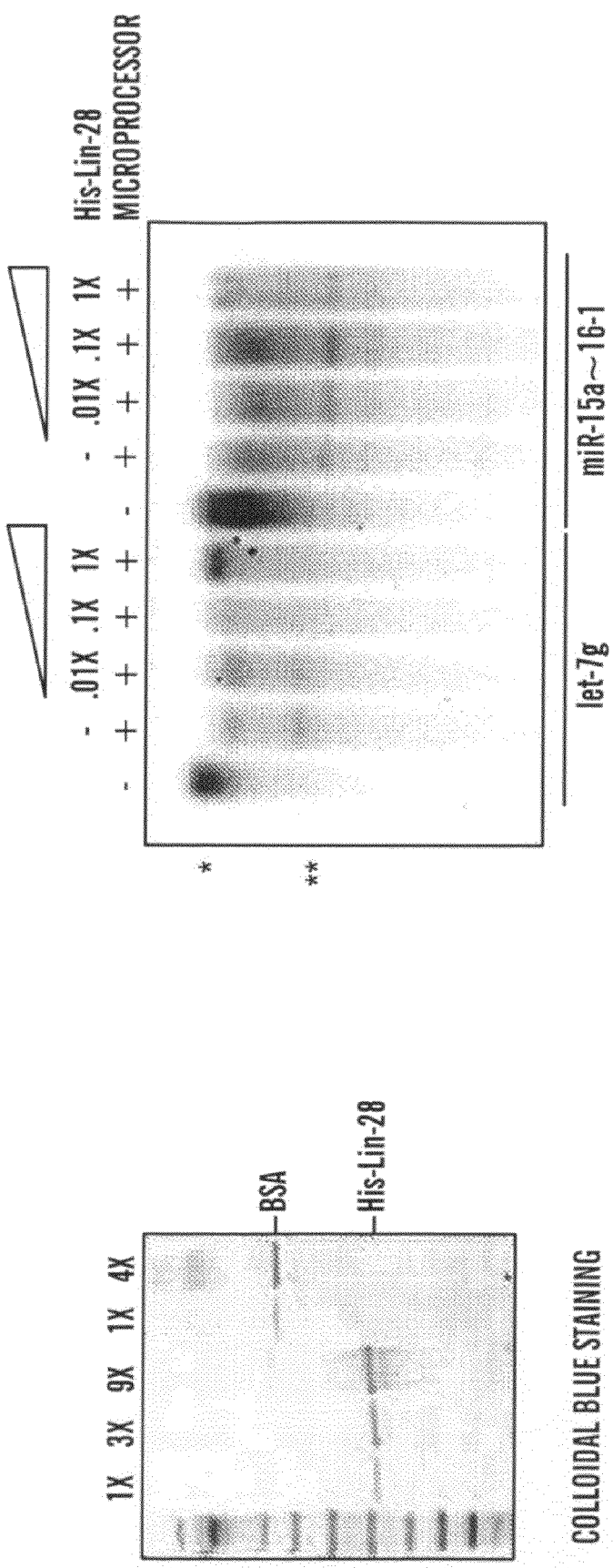

The inventors confirmed that Lin-28 is capable of binding both pre-let-7g and pri-let-7g in a co-sedimentation assay (FIG. 6). To examine whether Lin-28 is sufficient to functionally block pri-miRNA processing, the inventors next purified bacterially-expressed His-Lin-28 FIG. 2a) and tested this recombinant Lin-28 (rLin-28) for its ability to block processing of either pri-let-7g or pri-miR-15a/16-1. While 50 ng of rLin-28 is able to completely block processing of pri-let-7g, processing of pri-miR-15a/16-1 is unaffected when up to 500 ng rLin-28 is added (FIG. 2b). Therefore, the inventors demonstrated that Lin-28 is sufficient to cause a selective blockade in miRNA processing at the Drosha step.

To determine whether Lin-28 is capable of blocking miRNA processing in vivo, pri-let-7g was transiently transfected into 293T cells in either the presence or absence of mouse Lin-28. In the absence of Lin-28, ectopic pri-let-7g is efficiently processed into the mature let-7g miRNA (FIG. 3a, lane 2). In contrast, co-transfection of pri-let-7g with full-length Lin-28 cDNA led to an almost complete block in processing of pri-let-7g to the mature species (FIG. 3a, lanes 3-5). To demonstrate that Lin-28 does not merely cause a nonspecific blockade of miRNA processing, the inventors confirmed that Lin-28 had no inhibitory effect on processing of miR-15a and miR-16-1 (FIGS. 3b and 3c).

Figure 4A:
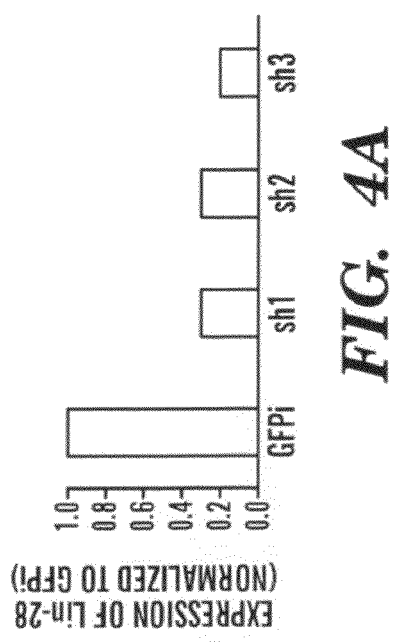
Figure 4B:
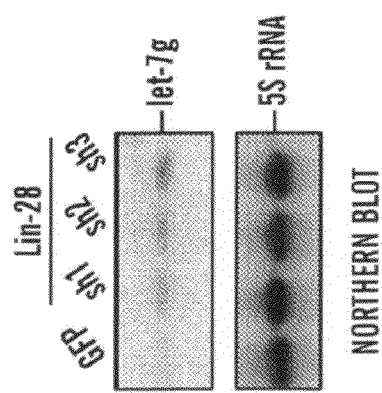

Finally, to demonstrate that Lin-28 is an endogenous blocker of miRNA processing in embryonal carcinoma cells, the inventors used shRNA hairpins targeting Lin-28 to knock down endogenous Lin-28 in P19 cells. Three different hairpins targeting Lin-28 gave comparable levels of knockdown (FIG. 4A). Knockdown of Lin-28 was shown to lead to an induction of mature let-7g, demonstrating that Lin-28 serves to inhibit miRNA processing in vivo (FIG. 4B). Induction of mature let-7g induction occurs within 60 hours of Lin-28 knockdown, while let-7g is normally induced only after several days of ES and P19 differentiation (FIG. 1a, and ref. Obernosterer, et al., RNA 12, 1161-1167 (2006)). Therefore, the induction of mature let-7g when Lin-28 is knocked down demonstrates a direct effect of Lin-28 on pri-miRNA processing.

Accordingly, the inventors have discovered and demonstrated that Lin-28 is necessary and sufficient for selective blockade of pri-miRNA processing both in vitro and in vivo.

There are several possible reasons why ES and EC cells possess a mechanism for post-transcriptional regulation of miRNA expression. First, post-transcriptional activation of miRNA processing would allow for rapid induction of a host of miRNAs by downregulation of a single factor. Second, miRNAs may be important for silencing the self-renewal machinery[13]. Therefore, post-transcriptional control of miRNA expression could prevent even small amounts of let-7 from being produced in ES and EC cells, therefore tightly maintaining them in an undifferentiated state[5]. Third, post-transcriptional control of miRNA expression could serve as a means for dissociating expression patterns of intronic miR-NAs from expression patterns of their host transcripts.

The inventors have discovered that Lin-28 blocks miRNA processing, and have demonstrated that down regulation of Lin-28 results in miRNA processing (such as let-7 miRNA processing) and thus leads to cells to mature let-7 which can function to suppress genes such as oncogenes. Thus the inventors have discovered that Lin-28 by blocking miRNA processing, plays a role in expression of genes normally suppressed by mature let-7 miRNA.

Lin-28 contains multiple let-7 target sites in its 3'-UTR, and Lin-28 mRNA has been reported to be targeted by mature let-7 miRNA[14], and therefore expression of Lin-28 mRNA transcript may be regulated by the expression of mature let-7 miRNA. Herein, the inventors demonstrate that the Lin-28 protein blocks the processing of pri-let-7g to mature let-7 miRNA. Therefore, the inventors have identified a positive feedback loop (FIG. 4c), whereby a small amount of mature let-7 produced upon differentiation represses Lin-28 protein translation, thus leading to increased pri-let-7 processing. Therefore, the inventors have identified an amplification loop whereby a small decrease in Lin-28 expression results in a small amount of mature let-7 miRNA, which in turn down-regulates Lin-28 further resulting in increased pri-miRNA processing and subsequent downstream effects such as cell differentiation in a rapid, controlled, and highly efficient manner.

Let-7 has been reported to play a tumor suppressor role by repression of oncogenes such as Hmga2[15] and Ras[16]. The inventors have demonstrated that disruption of let-7 processing by activation of Lin-28 could have an oncogenic phenotype. Notably, several human primary tumors show a general lack of correlation between expression of pri-miRNAs and the corresponding mature species[5,17], suggesting that globally low miRNA expression observed in many human cancers[18] may be the result of a block in miRNA processing rather than a transcriptional silencing of miRNA expression. Recently, global inhibition of miRNA processing by knock-down of Drosha was shown to promote cellular transformation and tumorigenesis[19]. The inventors have demonstrate that aberrant activation or overexpression of Lin-28 or a similar factor is a potential oncogenic mechanism by which miRNA levels could be globally repressed in human malignancies.

Example 2

Figure 7A:
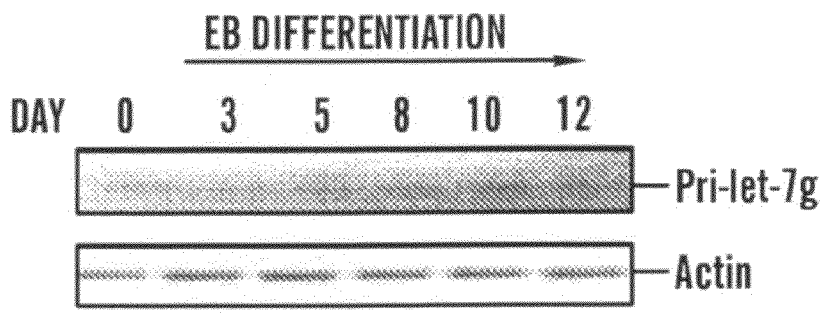
Figure 7B:
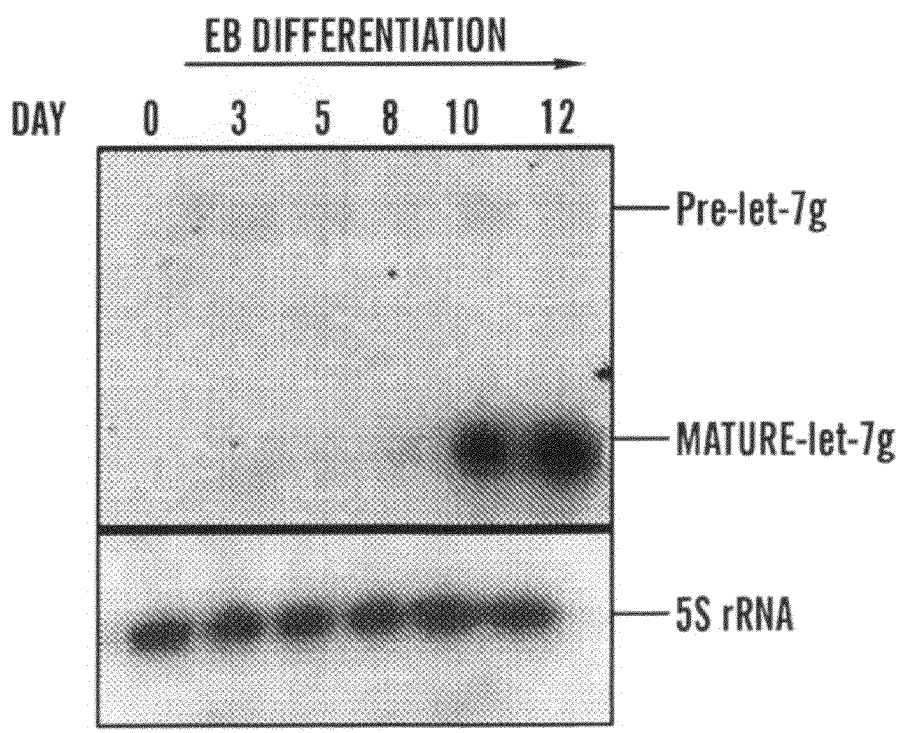
Figure 7C:
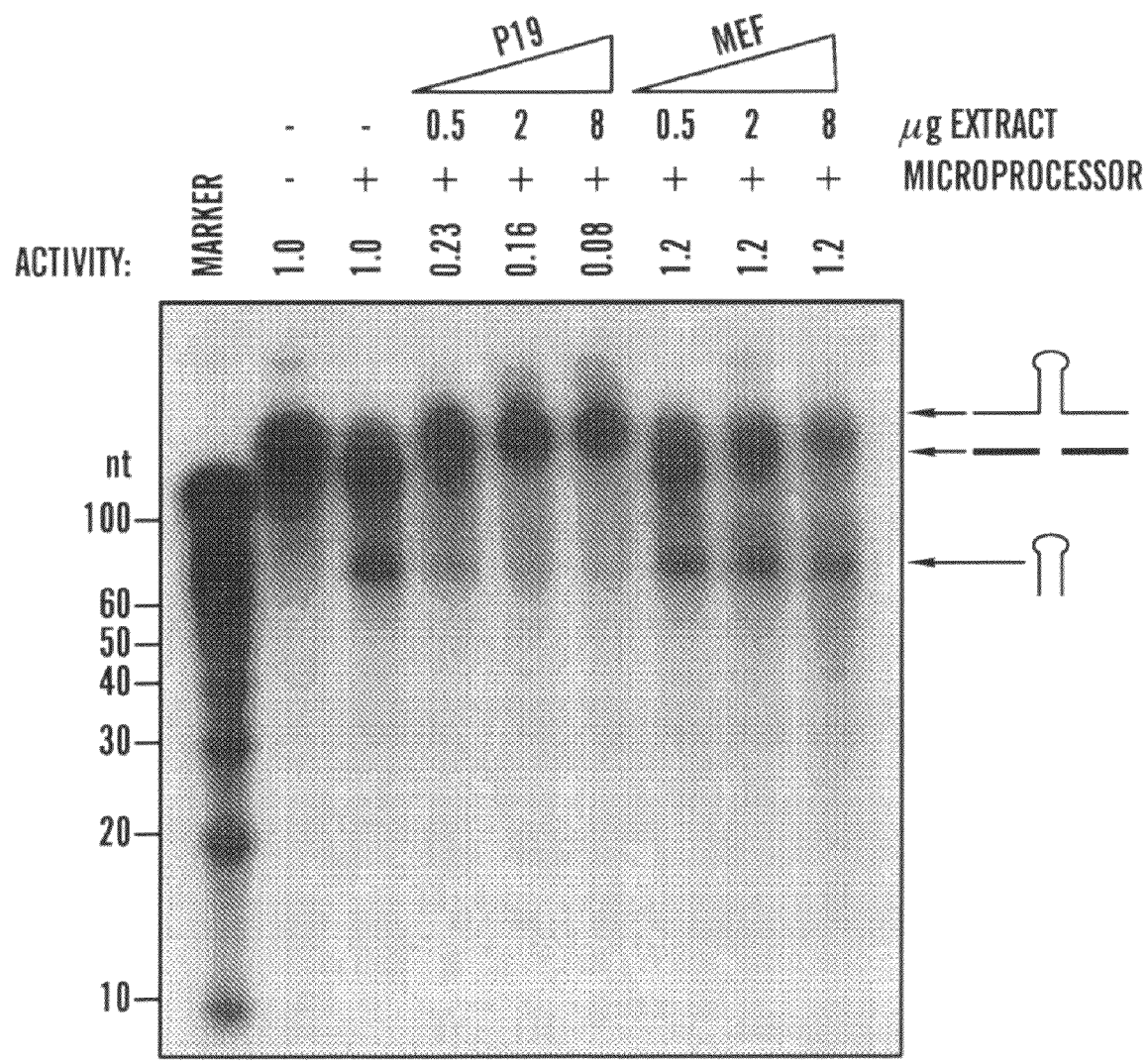

The inventors next demonstrated that the pri-let-7g transcript is readily detectable in ES cells and remains at relatively constant levels over the course of differentiation into embryoid bodies (FIG. 7a). In contrast, mature let-7g is undetectable in undifferentiated ES cells but is strongly induced after day 10 of differentiation (FIG. 7b). A post-transcriptional induction of let-7g expression has also been reported during the differentiation of P19 EC cells with retinoic acid (J. M. Thomson et al., Genes Dev. 20, 2202-2207 (2006). The inventors sought to understand the mechanism for the post-transcriptional block in miRNA processing in EC and ES cells. The inventors first compared cell extracts from different cell types for their ability to inhibit Microprocessor-mediated cleavage of pri-miRNA substrates to the corresponding pre-miRNAs in vitro (FIG. 7c). Radiolabeled pri-miRNA substrates were preincubated with cell extract and subsequently subjected to processing by affinity-purified Microprocessor complex. Whereas extracts from undifferentiated P19 cells readily inhibited Microprocessor-mediated cleavage of pri-let-7g to pre-let-7g, cell extracts from differentiated mouse embryonic fibroblasts (MEF) did not inhibit cleavage. Thus, the cell-type specificity of the in vivo Microprocessor processing block is recapitulated in the inventors in vitro assay.

The inventors assessed if the protein factor or factors present in ES and EC cells might be inhibiting Microprocessor-mediated processing of pri-miRNAs, and we employed a biochemical approach to identify this factor. Electrophoretic gel mobility shift assays using a labeled pre-let-7g probe identified a specific band-shift present in P19 EC and ES extract but not with MEF extract (FIG. 11). This demonstrated that pre-let-7g could be used as an effective affinity reagent for purification of the factor(s) responsible for the Microprocessor processing block. Pre-let-7g was conjugated to agarose beads and incubated with whole cell extract from P19 cells. The affinity eluate was subjected to SDS-polyacrylamide electrophoresis (PAGE) followed by colloidal staining. Bands were excised and subjected to mass spectroscopic sequencing in three segments (FIG. 5). Sequencing revealed several RNA-binding proteins co-purifying with pre-let-7g. A number of these proteins were previously identified as members of a large Microprocessor-containing protein complex (Gregory et al., Nature 432, 235-240 (2004)) (FIG. 4).

One of the pre-let-7g-interacting proteins was the small, highly-conserved RNA-binding protein Lin-28. Lin-28 was an attractive candidate for the following reasons: 1) mutations within its RNA-binding domain have been shown to impair developmental timing regulation in C. elegans (Moss, et al, Cell 88, 637-646 (1997)); 2) it is expressed specifically in undifferentiated P19 cells, mouse ES cells (Polesskaya et al., Genes Dev. 21, 1125-1138 (2007)), and human ES cells (Richards, et al. Stem Cells 22, 51-64 (2004)), and down-regulated upon differentiation; and 3) a mammalian Lin-28 homolog, Lin-28B, is over-expressed in hepatocellular carcinoma, and over-expression of this gene promotes cancer cell proliferation in vitro (Guo et al., Gene 384, 51-61 (2006)); 4) it has been reported that Lin-28 is expressed in embryonic muscle, neurons, and epithelia in a stage-specific fashion, and Lin-28 is crucial for appropriate skeletal muscle differentiation (Polesskaya et al., Genes Dev. 21, 1125-1138 (2007)); 5) Lin-28 was recently used with three other factors to reprogram human somatic fibroblasts to pluripotency (Yu et al., Science (2007)).

Figure 7D:
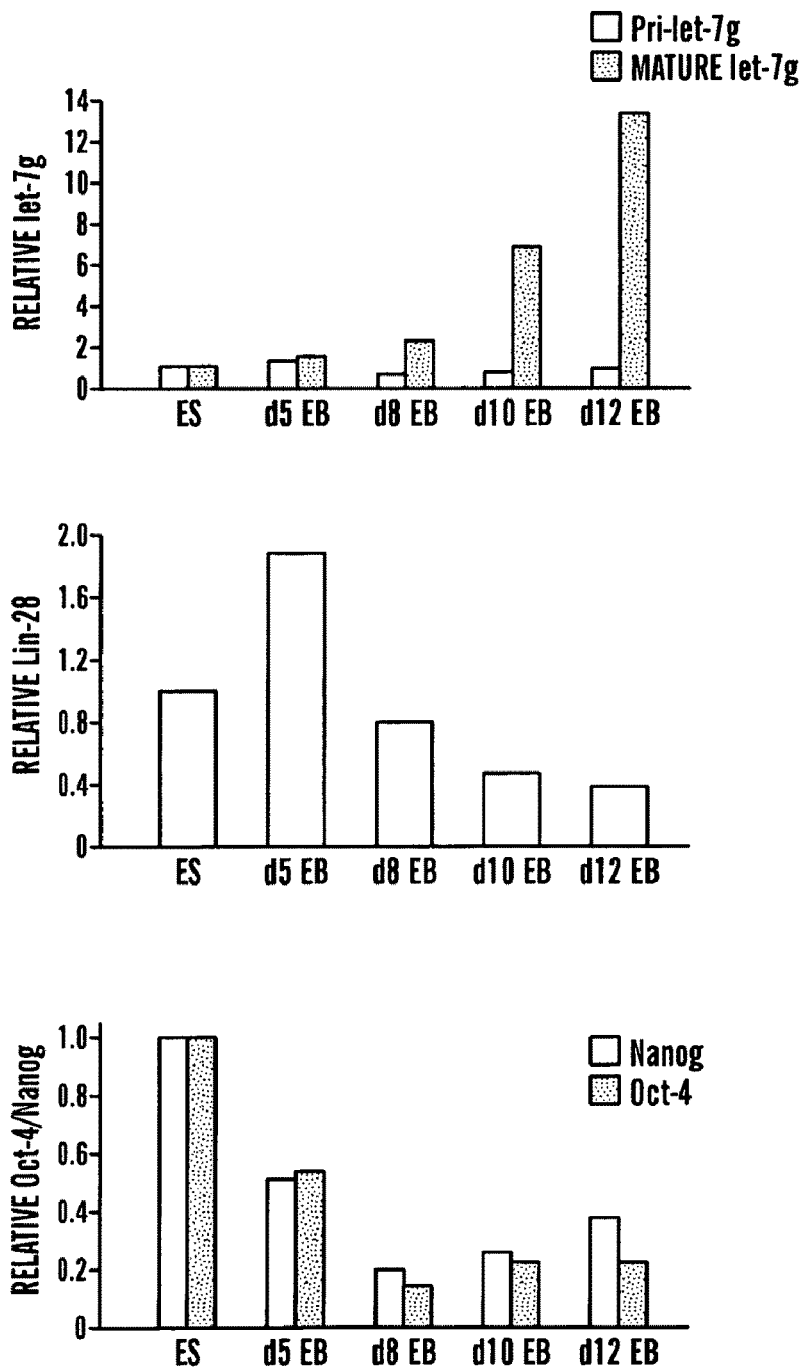

The inventors next determined the kinetics of Lin-28 expression during embryoid body formation (FIG. 7d). Lin-28 is downregulated upon ES cell differentiation, with kinetics that are delayed relative to the known pluripotency factors Oct-4 and Nanog. This downregulation of Lin-28 was demonstrated to temporally coincide with activation of pri-let-7 processing (FIG. 7d).

Figure 8A:
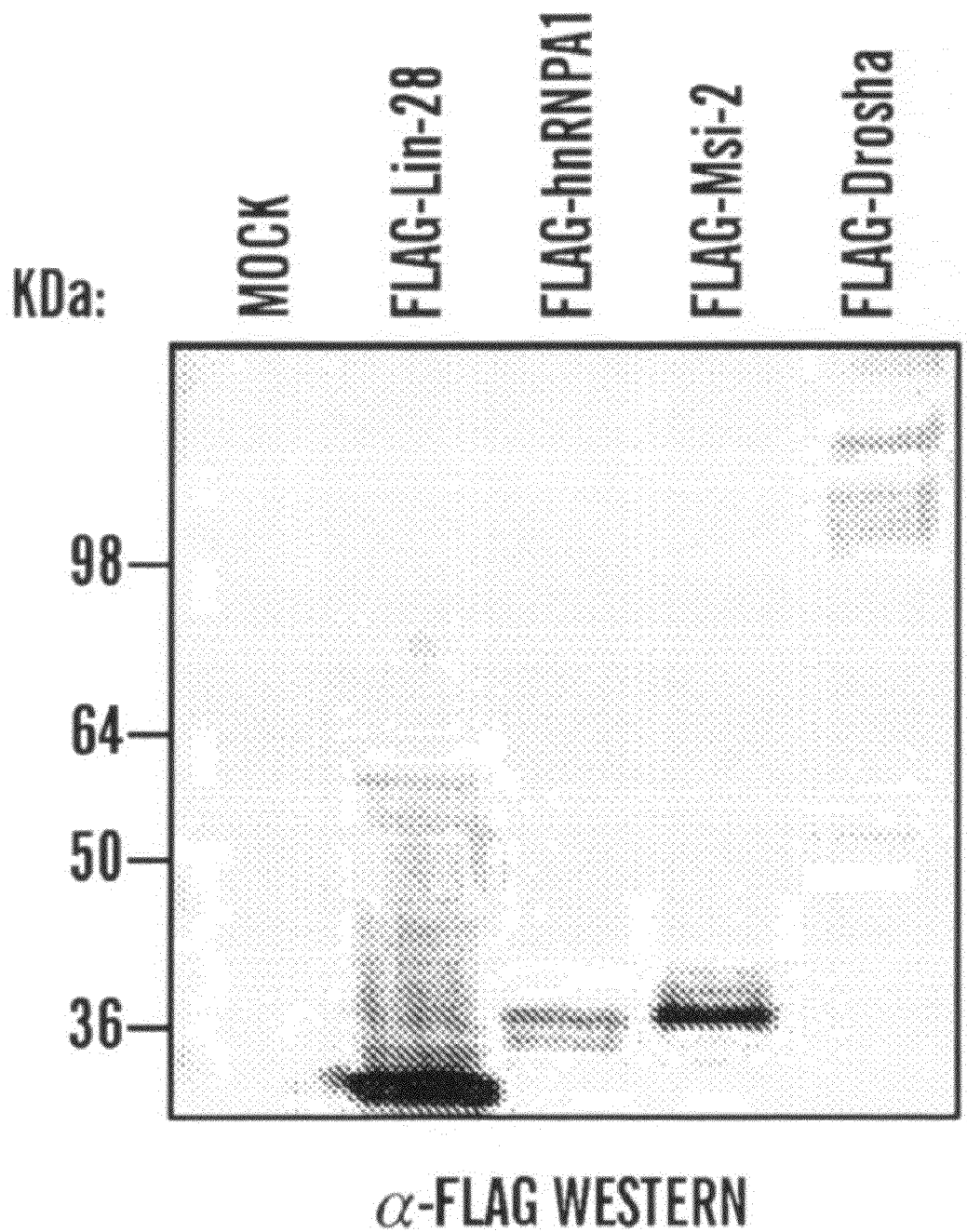
Figure 8B:
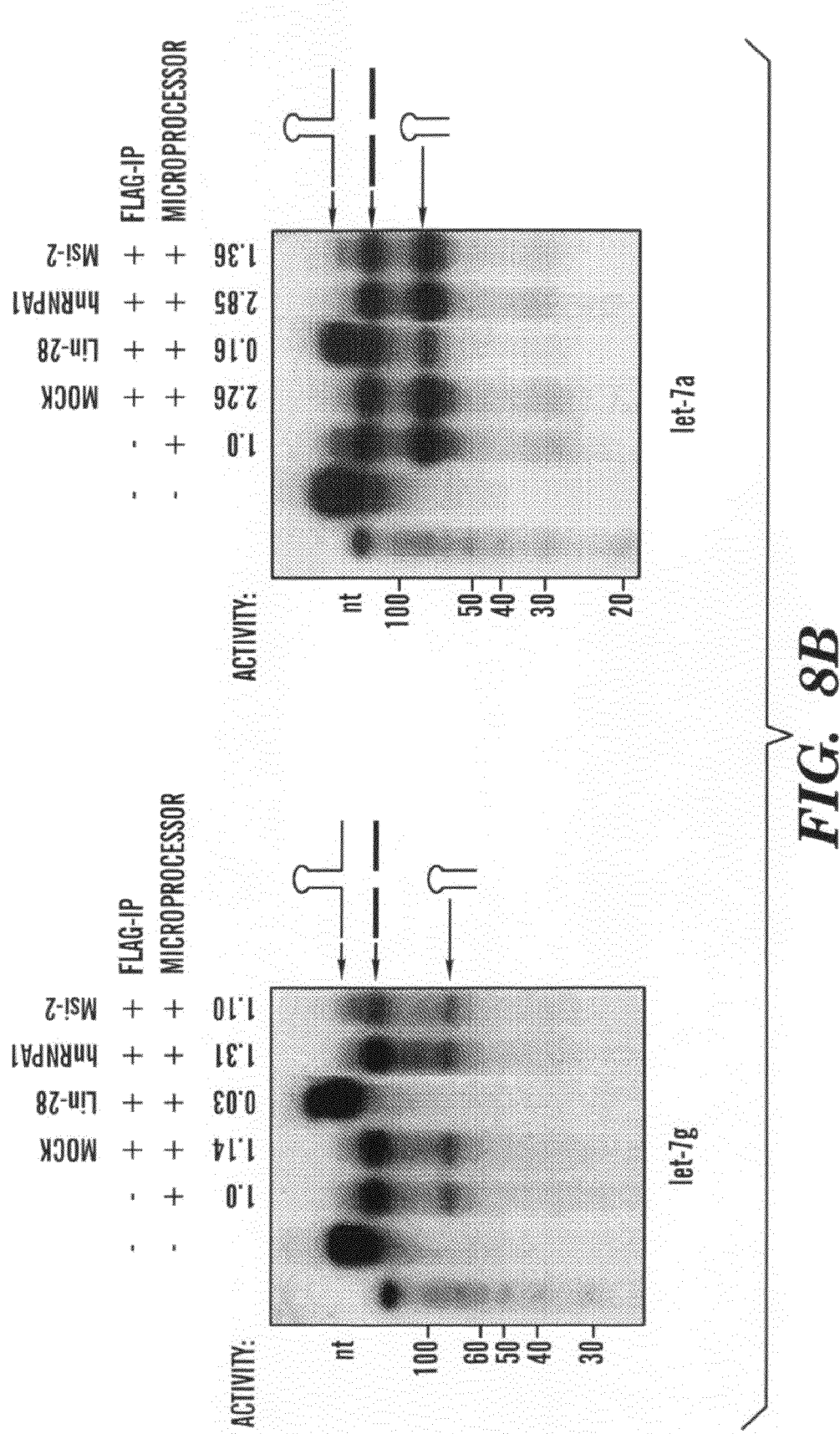
Figure 8C:
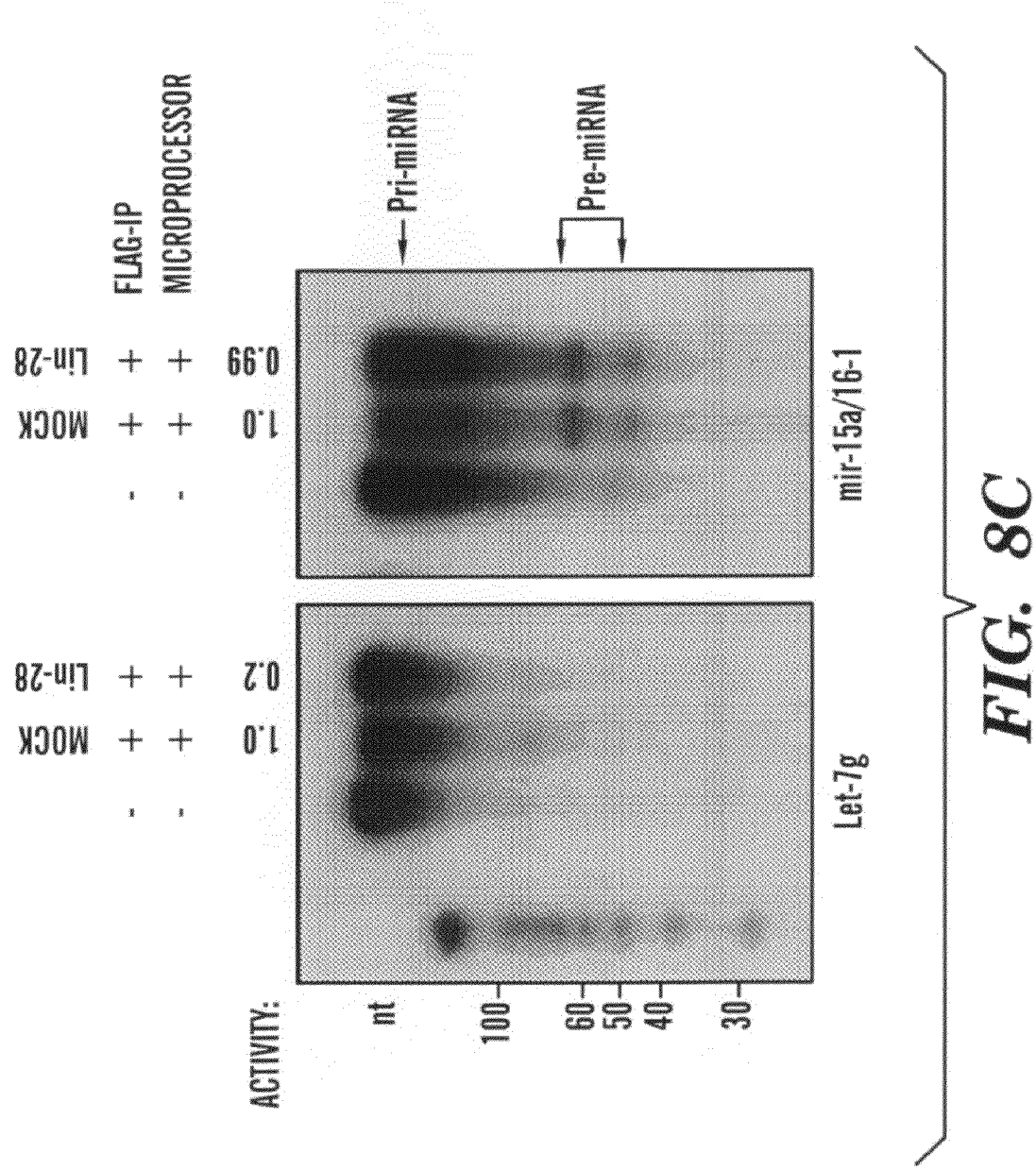
Figure 8D:
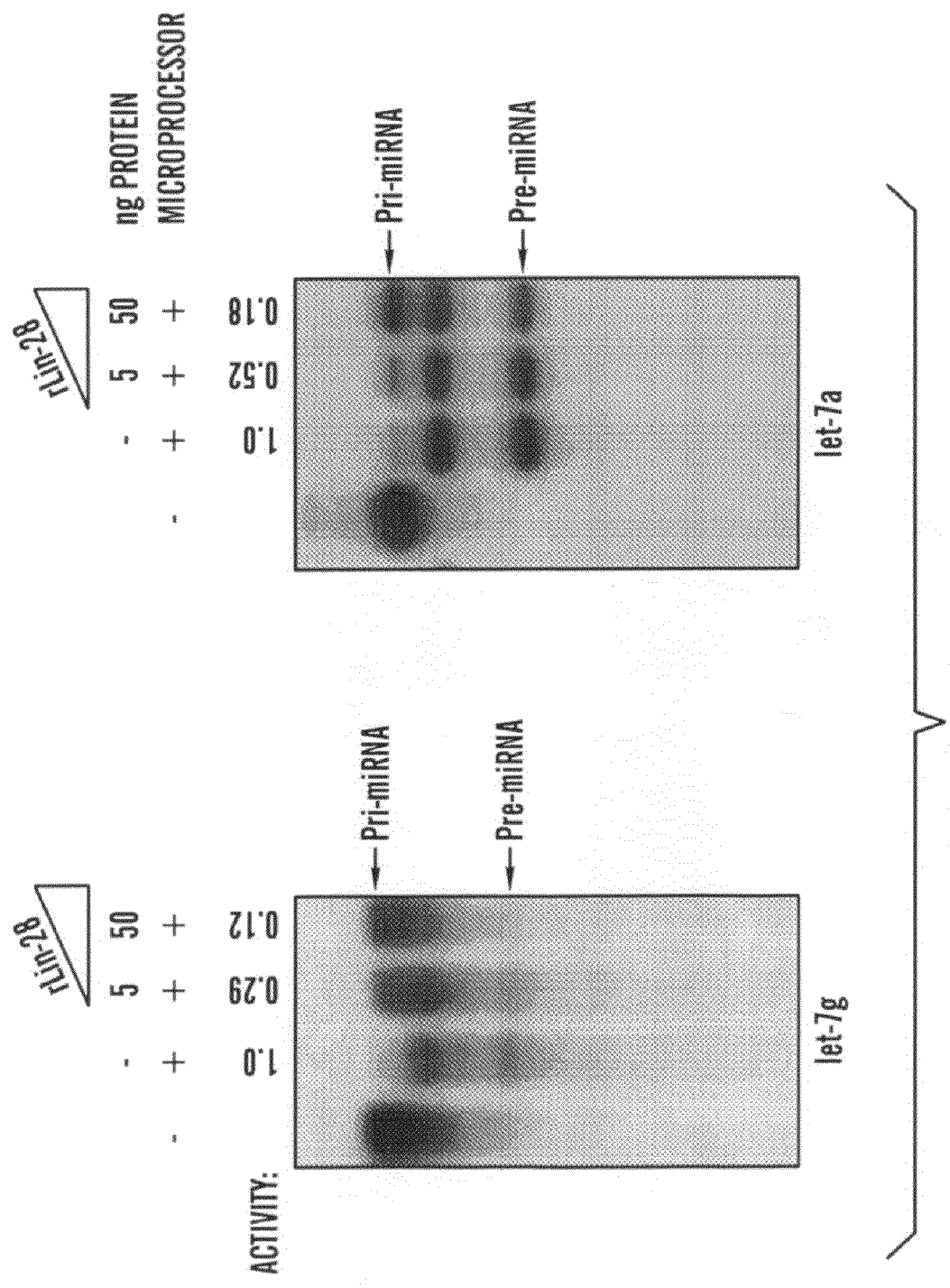

To examine if Lin-28 regulates pri-let-7 processing, the inventors demonstrated that Lin-28 is capable of binding both pre-let-7g and pri-let-7g in a co-sedimentation assay (FIG. 6). The inventors then tested the ability of Lin-28 to functionally block pri-miRNA processing in vitro. The inventors demonstrated that a Flag-immunoprecipitate containing Flag-Lin-28 potently inhibited the processing of both pri-let-7a and pri-let-7g in vitro. Flag-immunoprecipitates containing the control RNA-binding proteins Flag-hnRNPA1 and Flag-Msi-2 had no effect on pri-let-7a and pri-let-7g processing (FIGS. 8a and 8b). Flag-Lin-28 immunoprecipitate did not impair the processing of pri-miR15a/16-1, demonstrating the selectivity of the miRNA processing block (FIG. 8c). The inventors next purified bacterially-expressed His-Lin-28 (FIG. 8d) and tested this recombinant Lin-28 (rLin-28) for its ability to block pri-miRNA processing in vitro. rLin-28 inhibited the processing of both pri-let-7a and pri-let-7g (FIG. 8d). Therefore, this demonstrates that Lin-28 is sufficient to inhibit miRNA processing at the Microprocessor step.

Figure 9A:
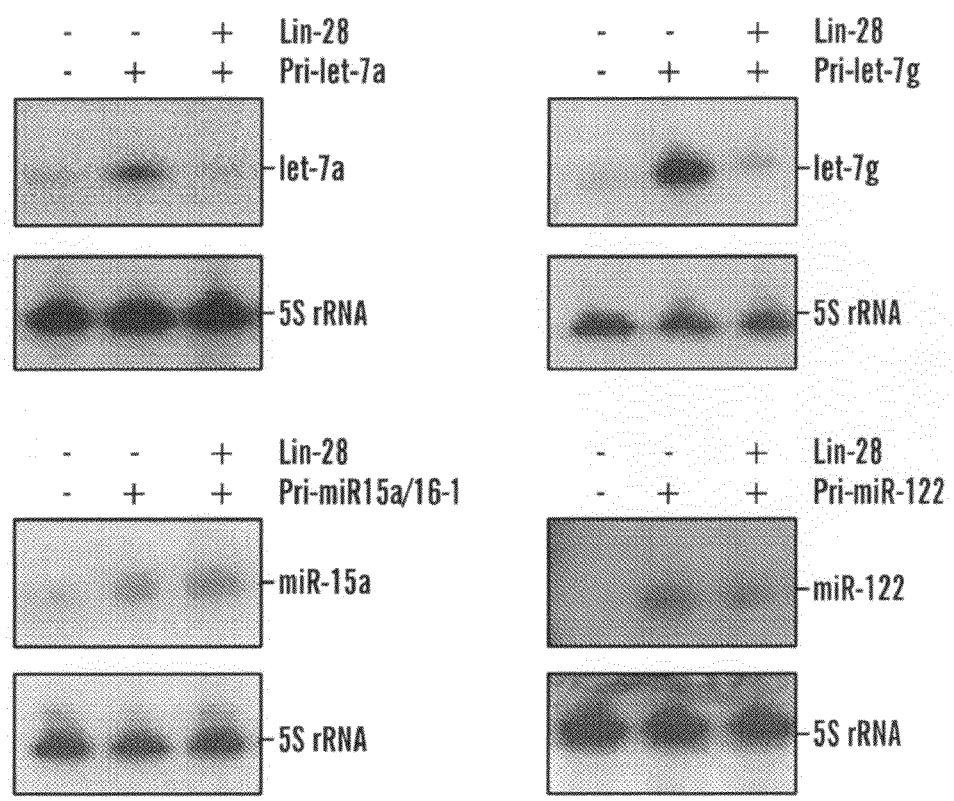
Figure 9B:
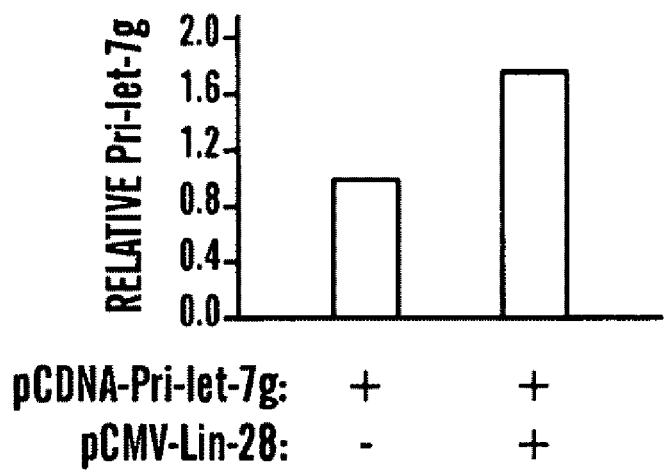
Figure 9C:
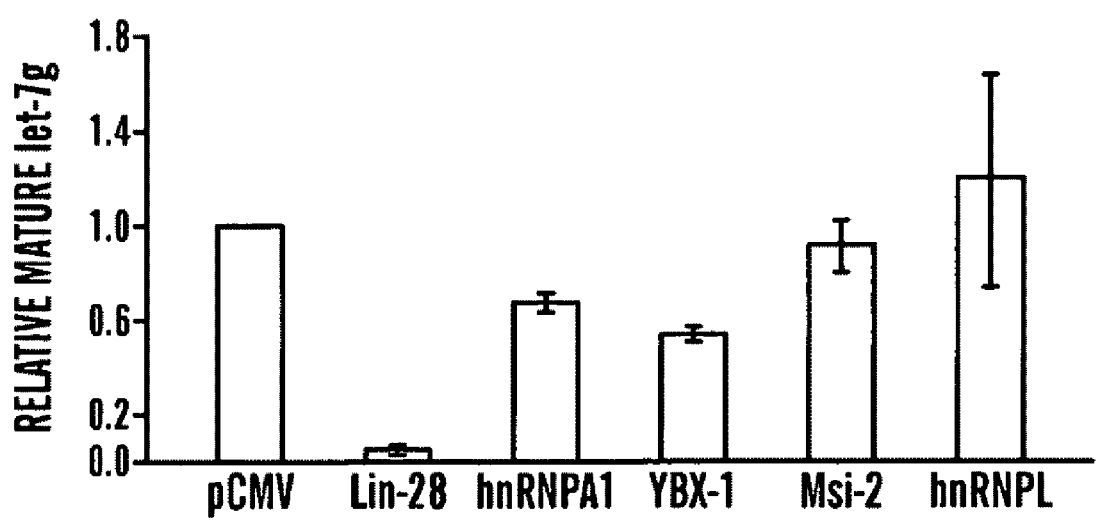
Figures 9D, 9E:
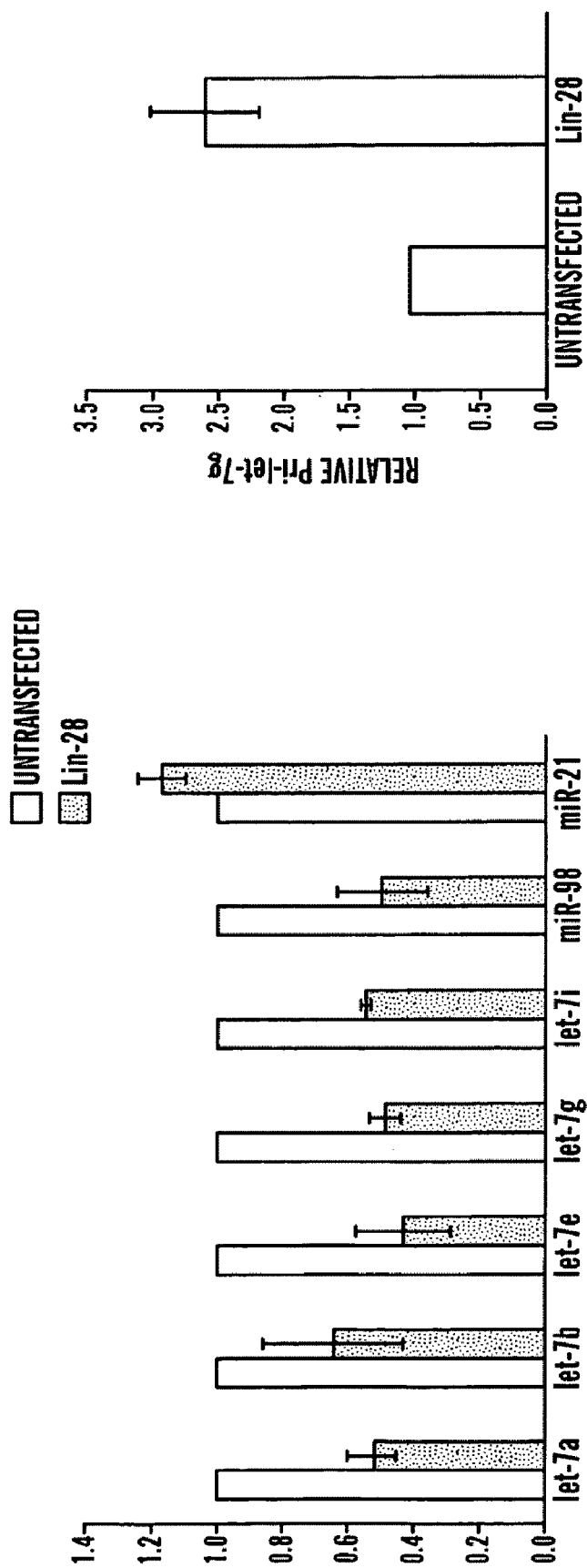

To determine whether Lin-28 is capable of blocking miRNA processing in vivo, four pri-miRNAs were introduced in either the presence or absence of mouse Lin-28 cDNA into 293T cells, a transformed human cell line that lacks Lin-28. In the absence of Lin-28, all ectopic pri-miRNAs were efficiently processed to their mature form (FIG. 9a and FIG. 12). However, ectopic expression of Lin-28 completely blocked processing of both pri-let-7a and pri-let-7g, while processing of pri-miR-15a and pri-miR-122 was largely unaffected (FIG. 9a and FIG. 12). Co-transfection of pri-let-7g and Lin-28 led to accumulation of pri-let-7g (FIG. 9b), demonstrating that Lin-28 blocks miRNA processing at the Microprocessor step. The inventors then performed these co-transfection experiments with four control RNA binding proteins (YBX-1, Msi-2, hnRNPA1, and hnRNPL) to confirm that this block in processing of pri-let-7 miRNAs is specific to Lin-28 (FIG. 9c and FIG. 13). Finally, to test whether Lin-28 is capable of blocking endogenous miRNA processing (as opposed to only blocking the processing of ectopically expressed pri-miRNAs), the inventors transfected Lin-28 cDNA into 293T cells and measured levels of several mature miRNAs after 4 days by quantitative PCR. The inventors demonstrated decreased endogenous levels of mature let-7 family members; levels of endogenous mature miR-21 were unaffected (FIG. 9d). Decreased mature let-7g upon Lin-28 over-expression was accompanied by a corresponding increase in levels of pri-let-7g (FIG. 9e).

Figure 10C:
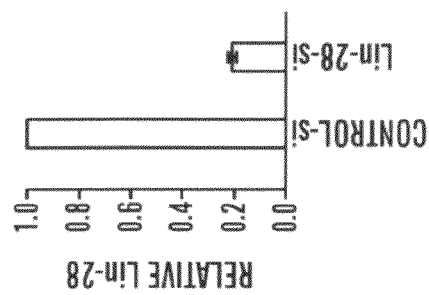
Figure 10B:
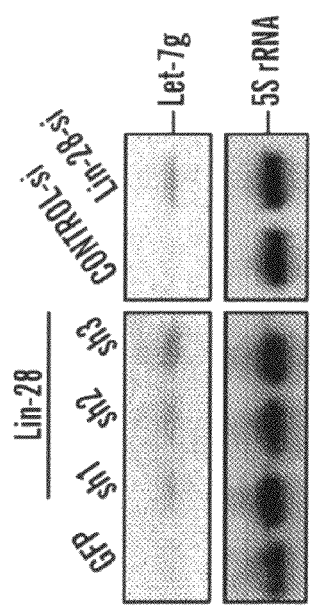
Figure 10A:
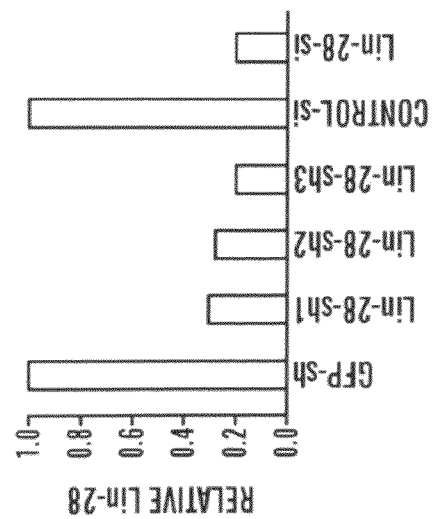
Figure 10D:
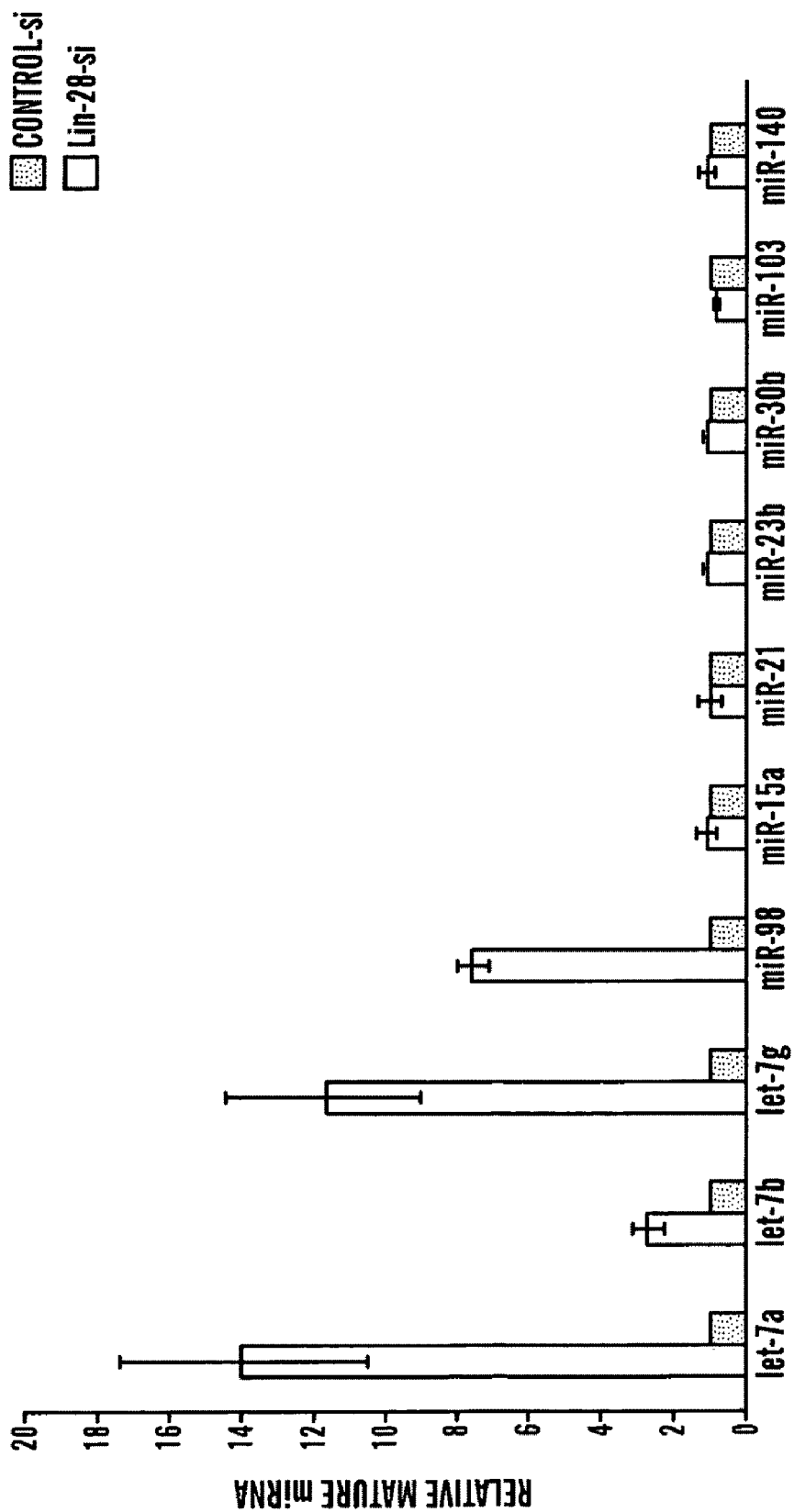
Figure 10F:
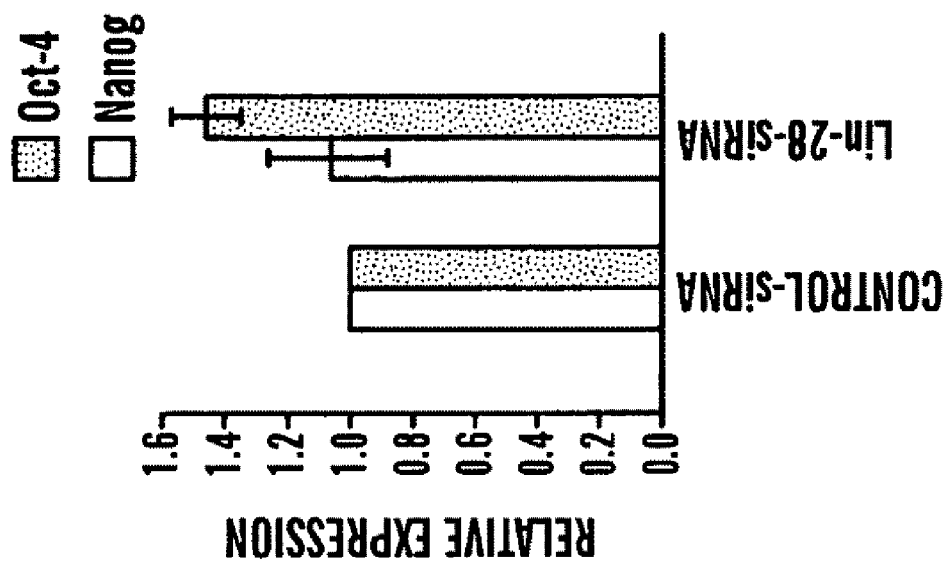
Figure 10E:
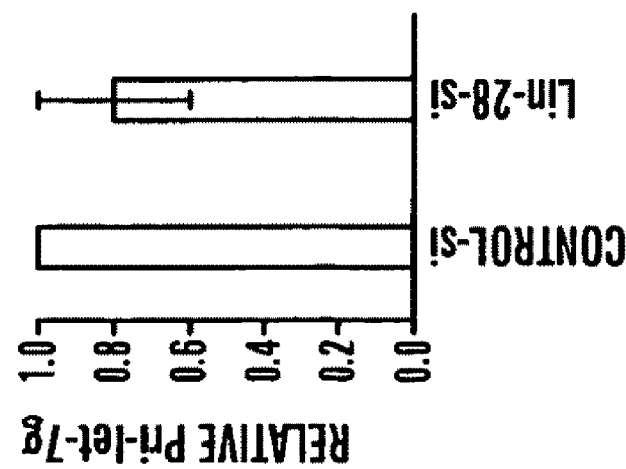

The inventors also determined whether Lin-28 is an endogenous blocker of miRNA processing in embryonic cells. The inventors used three different shRNA hairpins and a siRNA targeting Lin-28 to knock down endogenous Lin-28 in P19 EC cells (FIG. 10a) and ES cells (FIG. 14). Knockdown of Lin-28 leads to an induction of mature let-7g in both P19 cells (FIG. 10b) and ES cells (FIG. 12b), demonstrating that Lin-28 serves to inhibit miRNA processing in vivo (FIG. 10b). All let-7 family members tested were substantially upregulated upon knockdown of Lin-28, whereas levels of other miRNAs were unchanged (FIG. 10d and FIG. 15). Induction of mature let-7 miRNAs occurs within 60 hours of Lin-28 knockdown, whereas let-7 miRNAs are normally induced only after 10 days of ES and P19 differentiation, when endogenous Lin-28 levels fall (FIG. 7a, and ref. (Thomson et al., Genes Dev. 20, 2202-2207 (2006)). Therefore, the induction observed demonstrates a direct effect of Lin-28 on pri-miRNA processing rather than an indirect consequence of cell differentiation. The inventors also demonstrated that no decrease in levels of the pluripotency markers Oct-4 and Nanog upon knockdown of Lin-28 over the time course of our experiment (FIG. 10f). Furthermore, global miRNA profiling detected upregulation of only let-7 miRNAs upon Lin-28 knockdown, underscoring the specificity of Lin-28 in regulating let-7 miRNAs (FIG. 15).

A Lin-28 homologue, Lin-28B, is overexpressed in human hepatocellular carcinoma as well as in several cancer cell lines (Guo et al., Gene 384, 51-61 (2006)). Two isoforms of Lin-28B, differing in their 5' exons, have been reported. The short isoform (Lin-28B-S) preserves the two retroviral-type CCHC zinc-finger motifs also present in the long isoform (Lin-28B-L), but contains a truncated cold-shock domain. Lin-28B-L overexpression induces cancer-cell growth, while Lin-28B-S overexpression has no effect (Guo et al., Gene 384, 51-61 (2006)). The inventors demonstrate that Lin-28B-L inhibits the processing of pri-let-7g (FIG. 16) while Lin-28B-S does not. Therefore the inventors have demonstrated that the previously reported oncogenic properties of Lin-28B is mediated, at least in part, through blockade of let-7 processing. The inventors have demonstrated that Lin-28 and Lin-28B requires both the cold-shock domain and CCHC zinc-fingers for blocking activity. Interestingly, Lin-28 and Lin-28B are the only animal proteins to contain both of these domains (Balzer et al., RNA. Biol. 4, 16-25 (2007)). The inventors have demonstrated that Lin-28 is necessary and sufficient for blockade of pri-miRNA processing of let-7 family members both in vitro and in vivo.

The inventors data demonstrate that Lin-28 has a preference for selectively blocking the processing of let-7 family pri-miRNAs at the Microprocessor step. Lin-28 is predominantly localized to the cytoplasm, although it can also be found in the nucleus Moss et al., Cell 88, 637-646 (1997); Polesskaya et al., Genes Dev. 21, 1125-1138 (2007)); Lin-28B is translocated into the nucleus in a cell-cycle dependent fashion (Guo et al., Gene 384, 51-61 (2006)). Lin-28 may post-transcriptionally regulate miRNA processing in embryonic cells in a cell-cycle specific manner.

Recently, Lin-28 was used in conjunction with Nanog, Oct-4, and Sox2 to reprogram human fibroblasts to pluripotency (Yu et al., Science (2007)). The inventors demonstrate that modulating miRNA processing may contribute to the reprogramming of somatic cells to an embryonic state. Additionally, global inhibition of miRNA processing by knockdown of the Drosha component of the Microprocessor was shown to promote cellular transformation and tumorigenesis; this phenotype was found to be, in large part, due to loss of let-7 expression (Kumar, et al., at Genet 39, 673-677 (2007)). Let-7 has been reported to play a tumor suppressor role in lung and breast cancer by repression of oncogenes such as Hmga2 (Mayr, et al., Science 315, 1576-1579 (2007)) and Ras (Johnson et al., Cell 120, 635-647 (2005); Yu et al., Cell 131, 1109-1123 (2007)). The inventors demonstrate that disruption of let-7 processing by activation of Lin-28 could promote the oncogenic phenotype. Notably, several human primary tumors show a general lack of correlation between expression of pri-miRNAs and the corresponding mature species (Thomson et al., Genes Dev. 20, 2202-2207 (2006); Calin et al., PNAS 99, 15524-15529 (2002)). This demonstrates that a block in miRNA processing contributes to the low miRNA expression observed in many human cancers (Lu et al., Nature 435, 834-838 (2005).

Example 3

Human tumors display a global reduction in miR expression as compared with normal tissues (Lu, et al. Nature 435, 834-838 (2005); Thomson, et al. Genes Dev. 20, 2202-2207 (2006). Perturbation of the miR processing pathway may be a functionally important step in oncogenesis, as inhibition of miR biogenesis by knockdown of the miR processing enzymes Drosha, DGCR8, and Dicer-1 promotes cellular transformation and tumorigenesis (Kumar, et al., Nat. Genet. 39, 673-677 (2007). The let-7 miRs, comprised of 12 family members spread amongst 8 distinct genomic loci, function as tumor suppressors by negatively regulating target oncogenes. Let-7 levels are decreased in a number of primary tumors (Lu, et al. Nature 435, 834-838 (2005); Bussing, et al., Trends Mol. Med. (2008); Dahiya, et al. PLoS. ONE. 3, e2436 (2008)) and low levels of let-7 correlate highly with increased transformation capacity in vitro (Kumar et al., Nat. Genet. 39, 673-677 (2007)). Over-expression of let-7 represses cellular proliferation pathways, inhibits cell growth, and decreases colony formation capacity (Schultz et al., Cell Res 18, 549-557 (0 AD); Mayr et al., Science 315, 1576-1579 (2007); Lee et al., Genes Dev. 21, 1025-1030 (2007). Additionally, let-7g inhibits non-small cell lung tumor development in both xenografts and in an autochthonous model of NSCLC (Kumar, et al., Nat. Genet. 39, 673-677 (2007); Esquela-Kerscher, A. et al. Cell Cycle 7, 759-764 (2008)). The physiological mechanisms by which let-7 and other miRs are downregulated in the context of oncogenesis remain unclear.

As the inventors have demonstrated herein in Examples 1 and 2 that Lin-28 could selectively block the processing of let-7 miRs (see also Viswanathan, et al., Science 320, 97-100 (2008)) which was later confirmed independently by two groups Newman, et al, RNA. 14, 1539-1549 (2008) and Rybak, A. et al. Nat. Cell Biol. 10, 987-993 (2008)), the inventors next assessed if Lin-28 over-expression can maintain low levels of let-7 in certain human cancers.

To date, there have been no systematic descriptions of Lin28 expression in human cancer, and no functional studies testing its oncogenic activity. To examine whether Lin28 and Lin28B are over-expressed in primary human tumor samples, the inventors analyzed and interrogated published microarray data from several primary tumor types, and discovered high levels of Lin28 and/or Lin28B expression in a discrete subset of human tumors including germ cell tumors, ovarian carcinoma, hepatocellular carcinomas (HCCs), and Wilms tumor (WT) (FIGS. 17 and 22). The inventors next confirmed Lin28/Lin28B expression by immunohistochemistry on both embryonal carcinoma (FIG. 17B) and ovarian carcinoma (FIG. 17E) tissue sections.

Figure 17A:
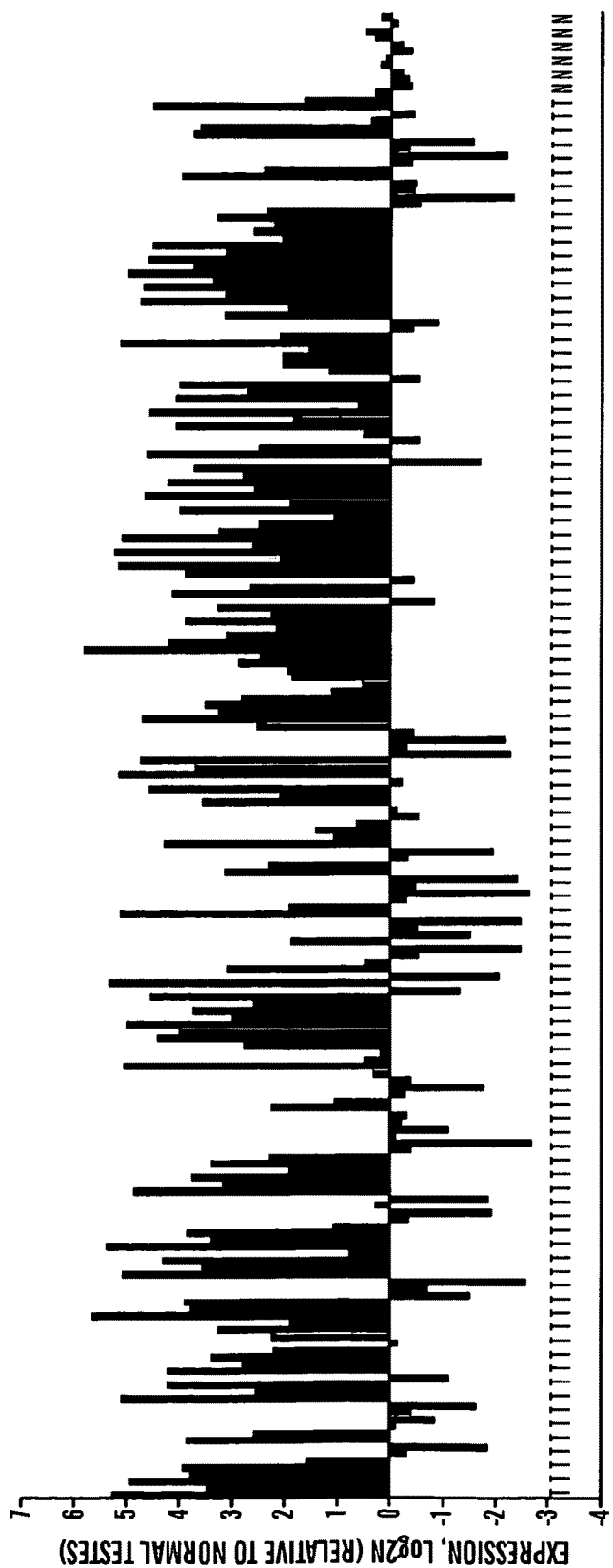
Figure 17B:
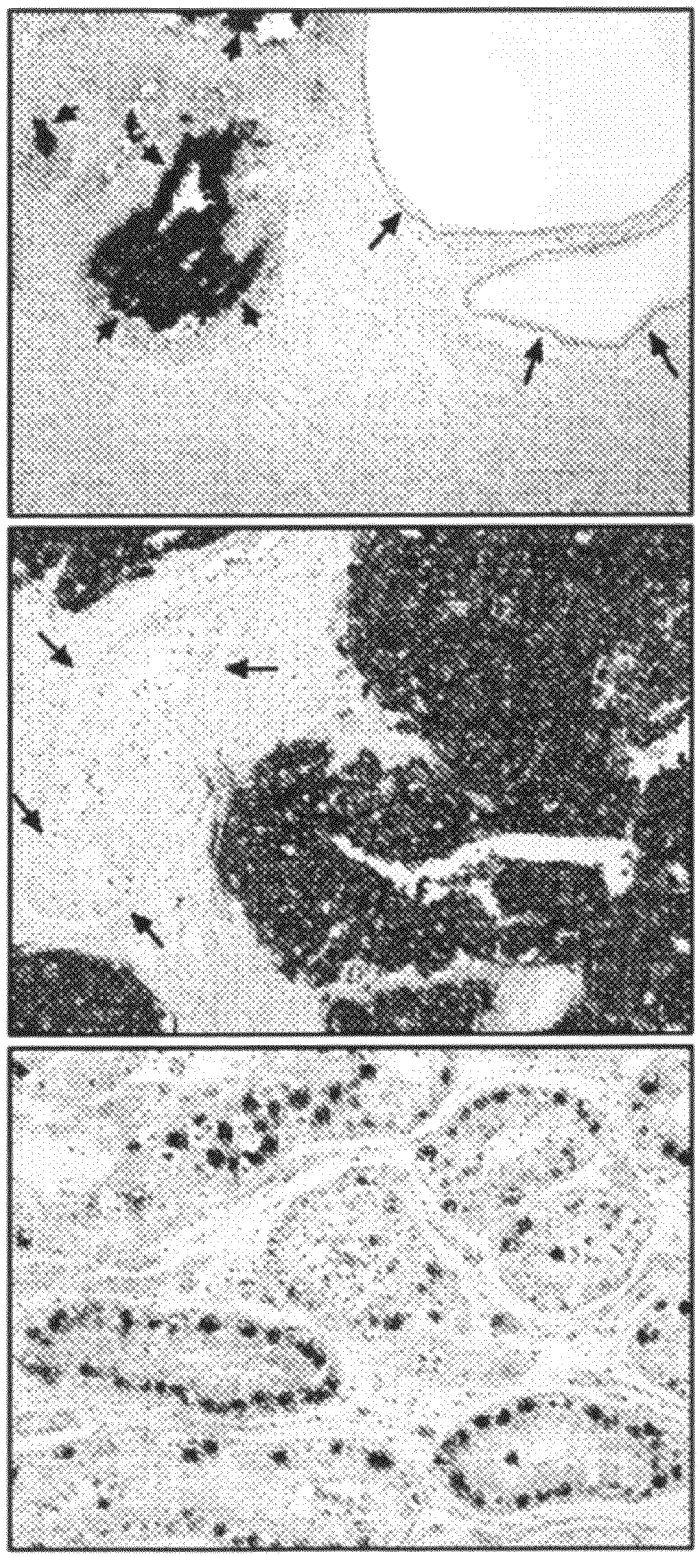
Figure 17C:
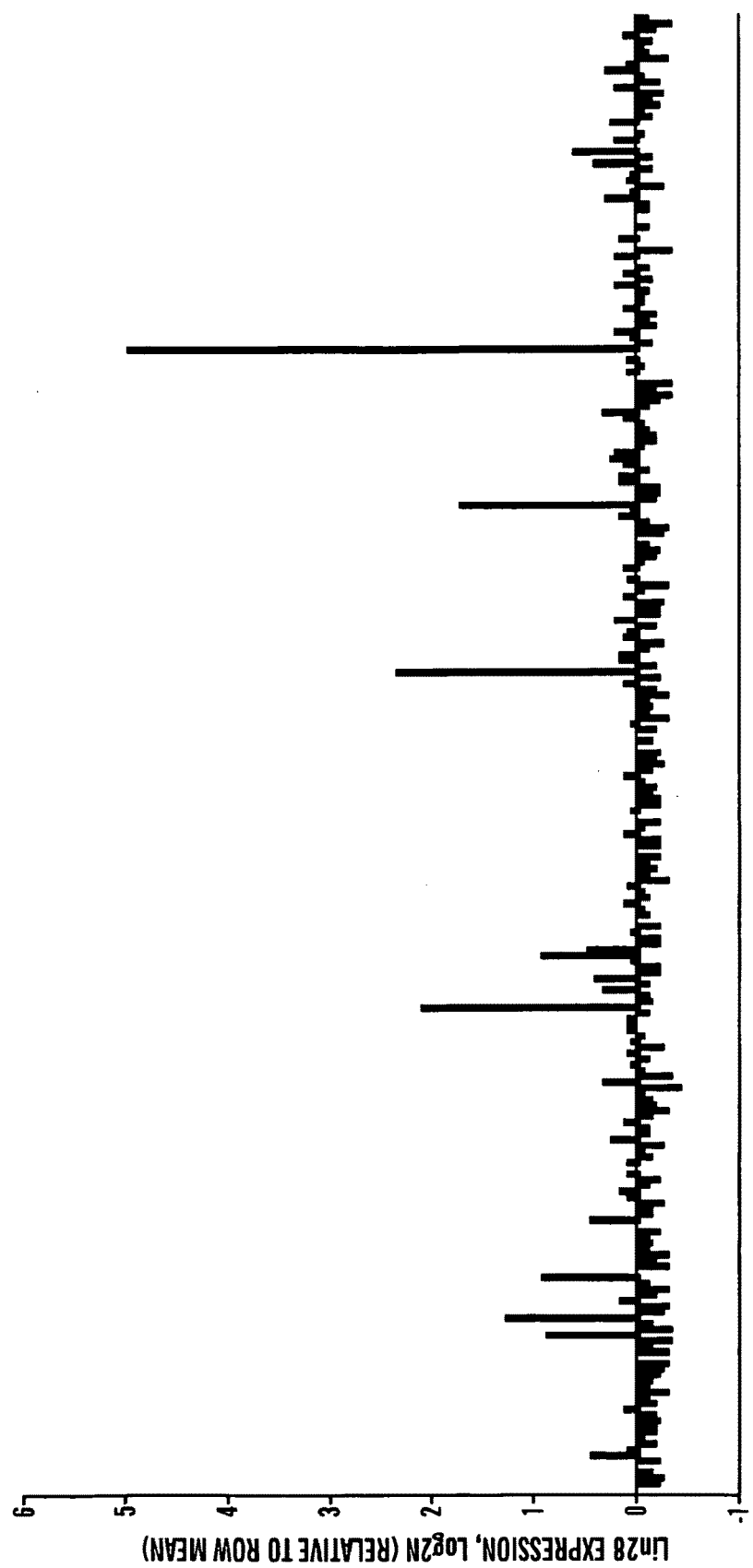
Figure 17D:
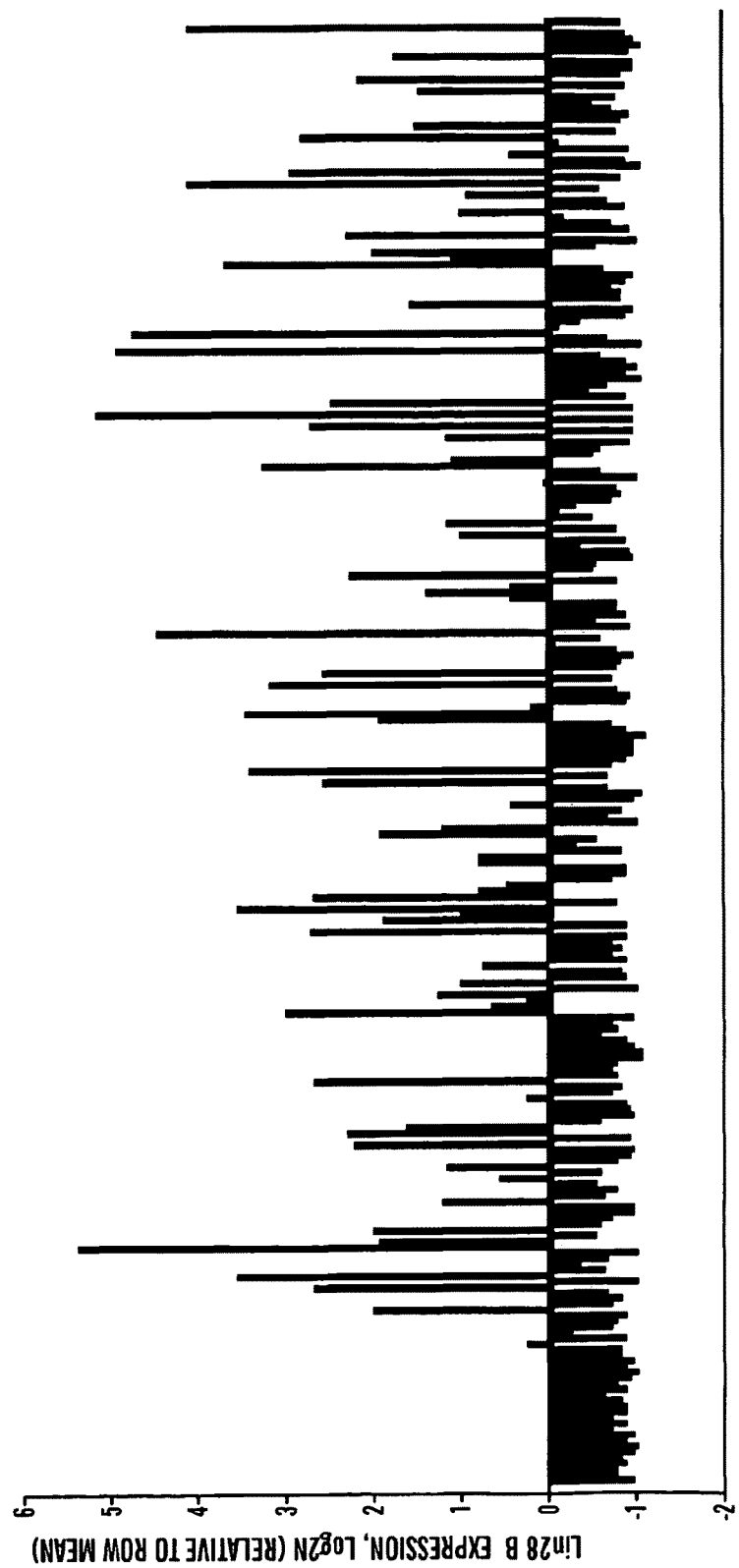

Analysis of microarray expression data from 101 male germ cell tumors revealed Lin28 over-expression (67/101; 66%) and Lin28B over-expression (45/101; 45%) in a large subset of tumors when compared with normal testes; Lin28 and Lin28B were co-expressed in 40% of tumors (40/101) (FIG. 17A). Immunohistochemistry on tissue sections from a human patient with embryonal carcinoma (FIG. 17B) using an antibody recognizing Lin28/Lin28B demonstrated strong expression in the tumor tissue, but no staining in adjacent stroma or in normal seminiferous tubules. Interestingly, this pattern of staining is similar to that of Oct-4, a well-characterized pluripotency marker that is used diagnostically to define germ cell tumors (Cheng, L. et al. J. Pathol 211, 1-9 (2007)).

Analysis of a microarray dataset comprising 255 ovarian tumors revealed high levels of Lin28 expression in a small subset of the tumors (3/255; 1.2%, FIG. 17C) and Lin28B expression in a larger proportion (11.8%, FIG. 17D) of tumors. Immunohistochemistry on ovarian tumor tissue showed strong staining for Lin28/Lin28B in tissue from three different subtypes of ovarian carcinoma: papillary serous carcinoma, clear cell carcinoma, and endometrial carcinoma (FIG. 17Ei-17Eiii). While no staining was detected in normal ovarian medulla (FIG. 17Eiv), moderate staining was discovered in the ovarian cortex and strong staining was discovered in ovarian surface epithelium (OSE) cells (FIG. 17Ev), which are thought to be the cells of origin of epithelial ovarian cancer (Bell, D. A. Mod Pathol 18, S19-S32 (0 AD)). Notably, low levels of let-7 have been shown to correlate with poor survival in patients with ovarian cancer (Shell, S. et al. Proceedings of the National Academy of Sciences 104, 11400-11405 (2007). Thus, the inventors have discovered that persistent expression of Lin28/Lin28B is likely to contribute to low levels of let-7 in theses cancer patient, which can be accountable to their poor survival with ovarian cancer.

The inventors also analyzed Lin28 and Lin28B expression in human HCC tumor samples. Lin28B was originally cloned from an HCC cell line and has been reported to be highly over-expressed in primary HCC samples (Guo, Y. et al. Gene 384, 51-61 (2006)). The inventors detected Lin28B expression in 16.3% (15/92) of human HCC tumors and 66% (4/6; p=0.00981, Fisher's Exact Test) of tumors from patients with serum alpha-fetoprotein (AFP)>10,000 ng/ml (FIG. 22A). Serum AFP levels>10,000 may be an independent predictor of poor survival after adjustment for tumor size and histology, suggesting that Lin28B activation may be associated with poor outcome in HCC (Matsumoto, Y. et al. Cancer 49, 354-360 (1982)). The inventors also discovered that higher levels of Lin28B expression in HCC patients also resulted in higher serum AFP levels (FIG. 22B). Interestingly, the inventors also discovered that AFP-expressing HCC tumors also appear to fall within a distinct expression-based subclass of HCC (data not shown).

The inventors analysis of expression profiling data from 67 human renal tumors of both pediatric and adult origin demonstrated that Lin28B was over-expressed in a discrete subset of WT samples (8/27; 30%), whereas Lin28 was not expressed in any of the samples analyzed (FIG. 22C). Notably, no instances of Lin28 or Lin28B over-expression were detected in the adult renal tumor samples profiled (renal cell carcinoma, chromophobe renal cell carcinoma, oncocytoma, and papillary renal cell carcinoma). Interestingly, Lin28B over-expression was discovered only in Stage 3 or 4 WT samples, demonstrating that activation of Lin28B is associated with advanced disease (p=0.00361, Fisher's exact test).

Example 4

Given the inventors discovery that Lin28/Lin28B are over-expressed in a discrete subset of human tumors, the inventors next sought to determine whether Lin28 has oncogenic activity in various experimental systems, particularly in contexts that are dependent on let-7 target oncogenes. The let-7 targets K-ras and c-myc are known to be critical effectors of BCR-ABL-mediated transformation (Mandanas, et al. Blood 82, 1838-1847 (1993); Sawyers, et al, Cell 70, 901-910 (1992)), and so the inventors initially examined whether Lin28 expression would enhance the transformation of NIH/3T3 cells, for which BCR-ABL is weakly transforming (Daley et al., Science 237, 532-535 (1987); Sawyers, et al., J. Exp. Med. 181, 307-313 (1995)).

Figure 18A:
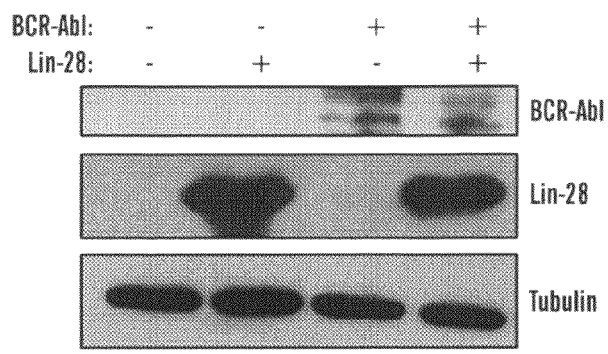
Figure 18B:
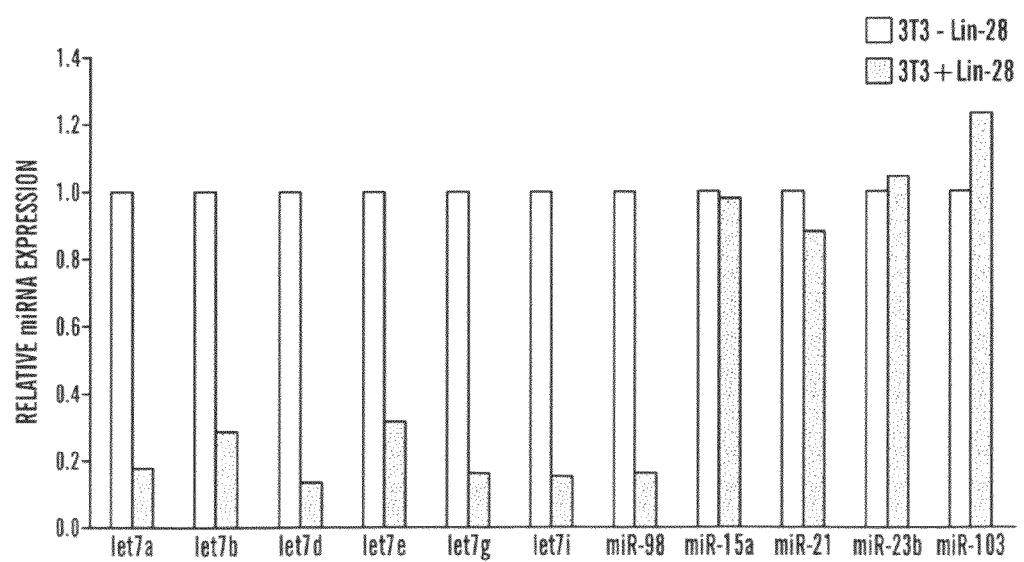
Figure 18C:
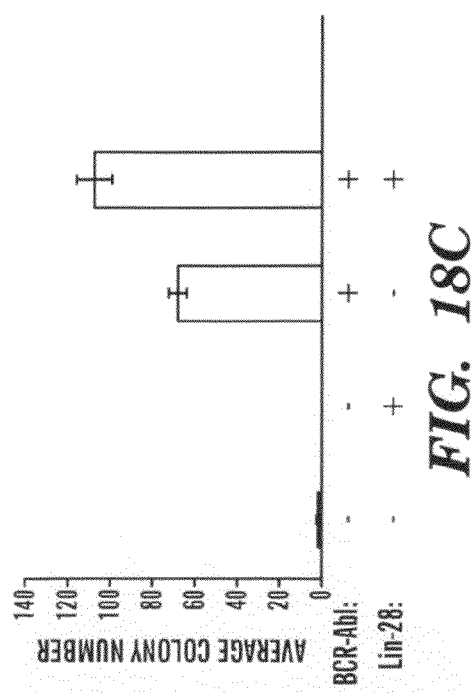
Figure 18D:
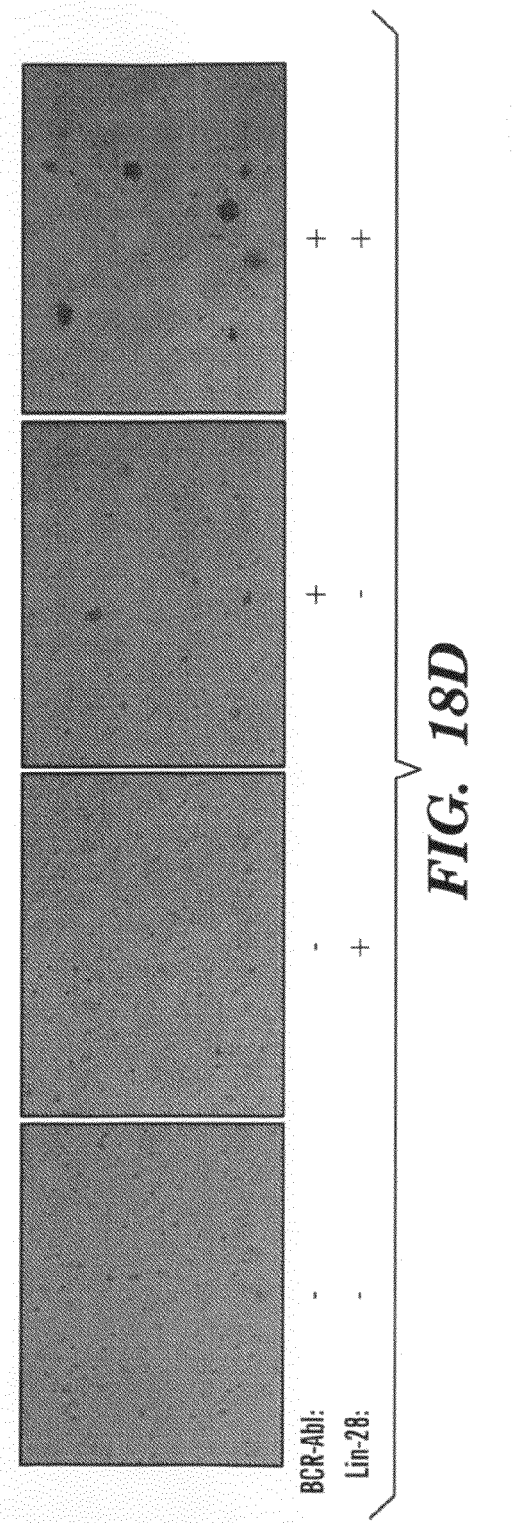

Retroviral-mediated expression of Lin28 in NIH/3T3 cells selectively depleted mature let-7 family miRs and led to upregulation of the let-7 target oncogenes c-myc and K-Ras (FIGS. 18A and 18B). While Lin28 expression alone did not promote anchorage independent growth in semisolid medium, when co-expressed with BCR-ABL, Lin28 substantially increased colony size and modestly increased colony number (FIGS. 18C-18D).

Figure 19A:
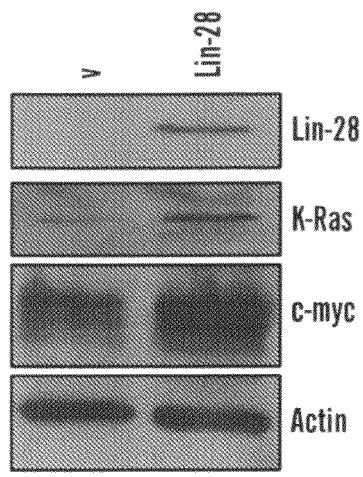
Figure 19B:
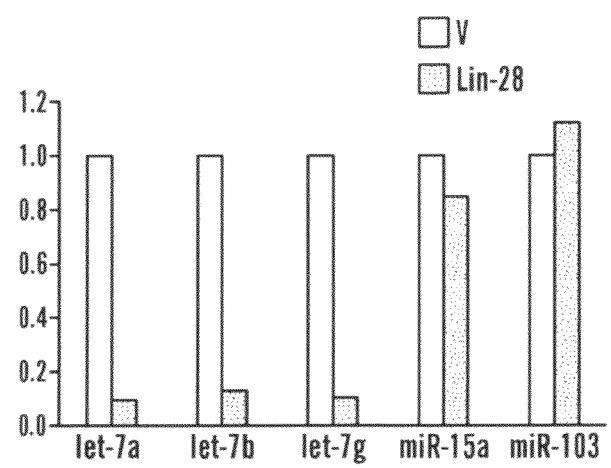
Figure 19C:
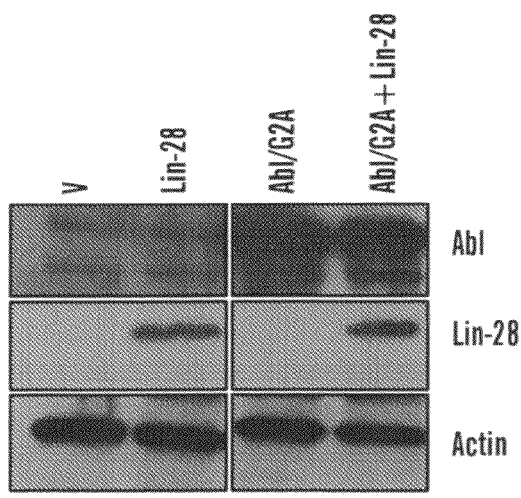
Figure 19D:
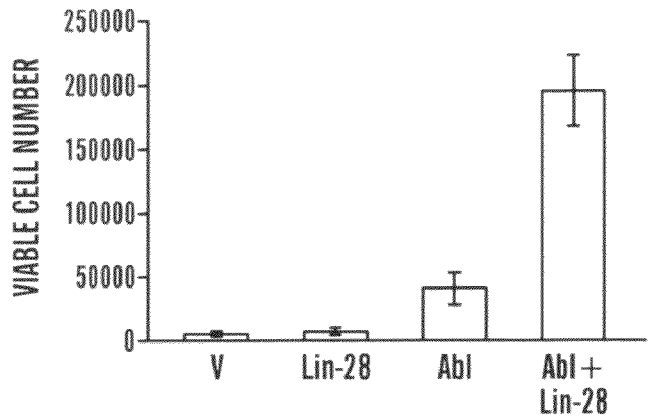
Figure 19E:
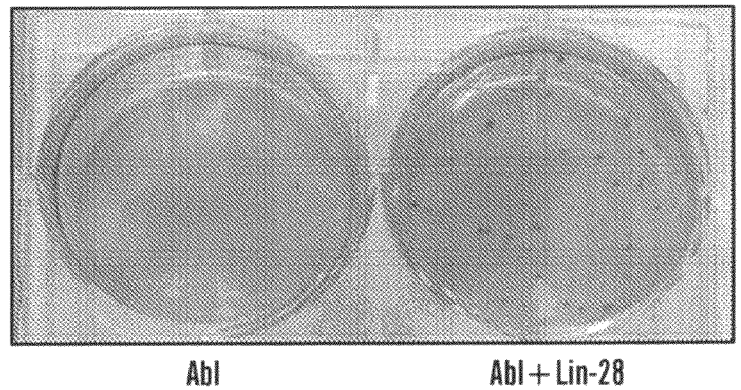
Figure 19F:
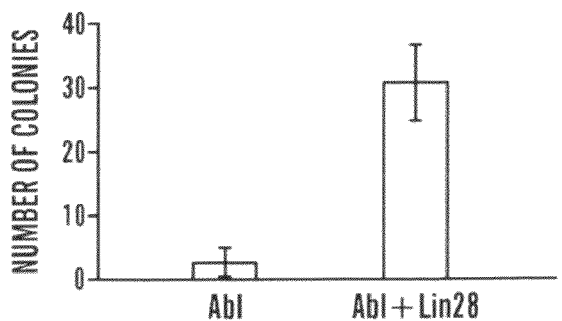

The inventors also tested Lin28 for its ability to transform cytokine-dependent BaF/3 cells to factor independence. Because BCR-ABL is maximally transforming in this system, the inventors sought to determine the ability of Lin28 to cooperate with a weaker transforming variant of ABL, ABL/G2A (Mathey-Prevot, B., Mol. Cell Biol. 6, 4133-4135 (1986); Azam, et al., Nat. Struct. Mol. Biol. (2008)). The inventors confirmed that Lin28 depleted mature let-7 species and led to the upregulation of K-Ras and c-myc in BaF/3 cells (FIGS. 19A-19B). Lin28 strongly synergized with Abl/G2A (Hantschel, et al. Cell 112, 845-857 (2003)) to confer IL-3 independence (FIG. 19C) and to promote anchorage-independent growth of BAF/3 cells in semisolid medium (FIG. 19D-19E). The inventors also discovered that Lin28 alone conferred IL-3 independence upon BaF/3 cells, but with delayed kinetics (data not shown). The inventors also discovered a synergy between Lin28 and an activated allele of Src (Src/Y530F), which is also known to be weakly transforming for BaF/3 cells (Mathey-Prevot, B., Mol. Cell Biol. 6, 4133-4135 (1986); Azam, et al., Nat. Struct. Mol. Biol. (2008)) (FIG. 23B). Consistent with the inventors discovery, BCR-ABL, v-abl, and v-src have all been demonstrated to transform lymphoid cells via a similar pathway Engelman, et al., Mol. Cell Biol. 10, 4365-4369 (1990)).

Example 5

Figure 20A:
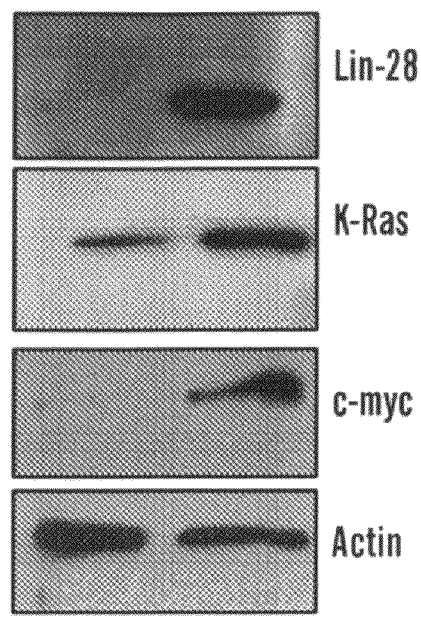
Figure 20B:
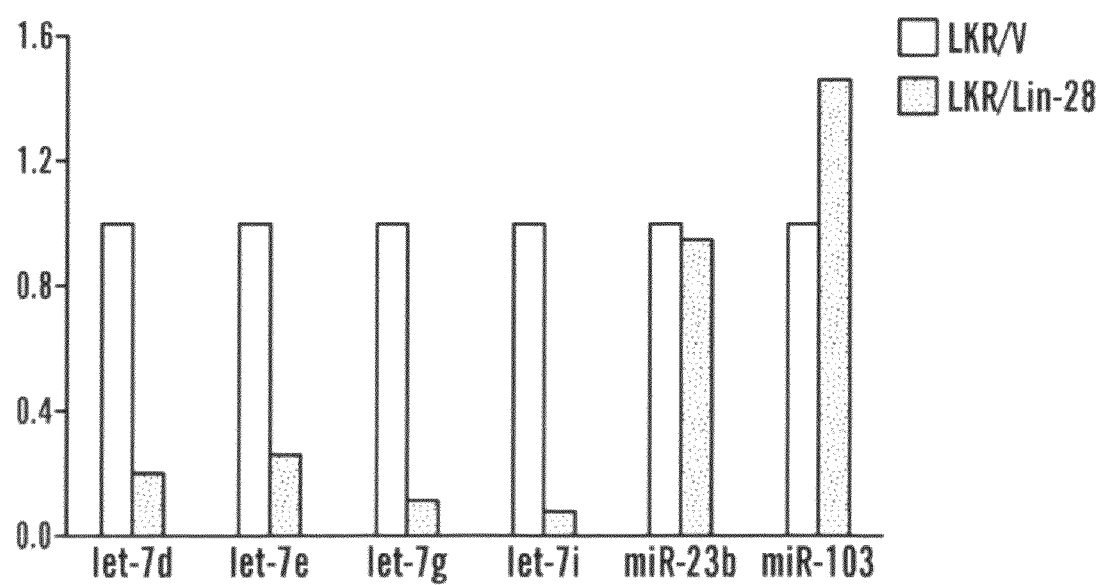
Figure 20C:
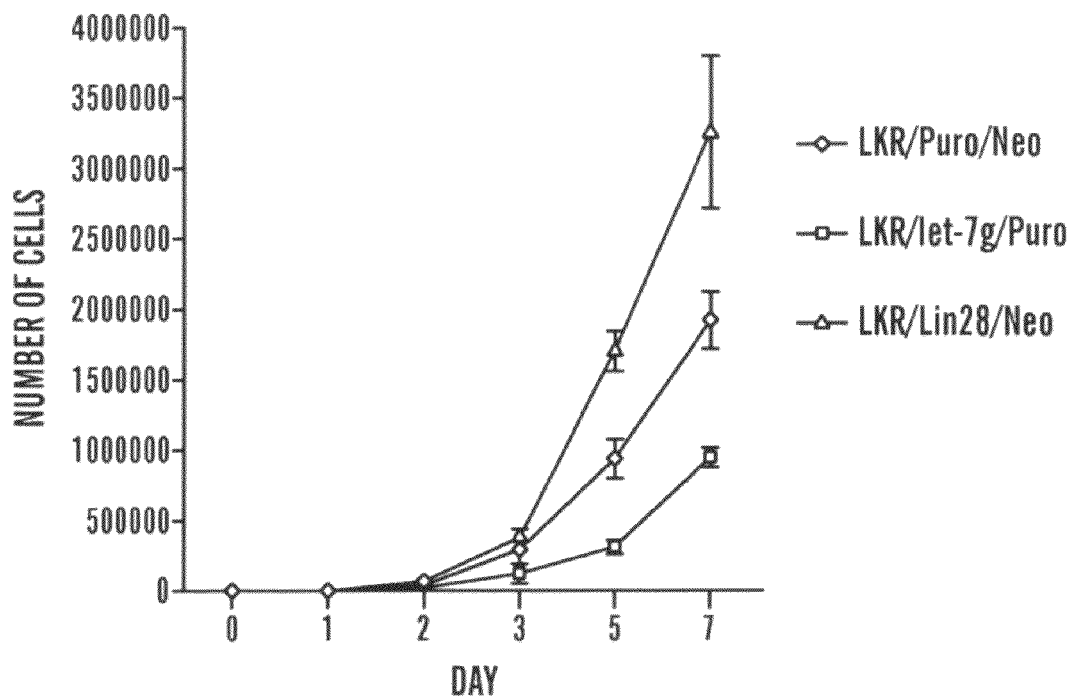
Figure 20D:
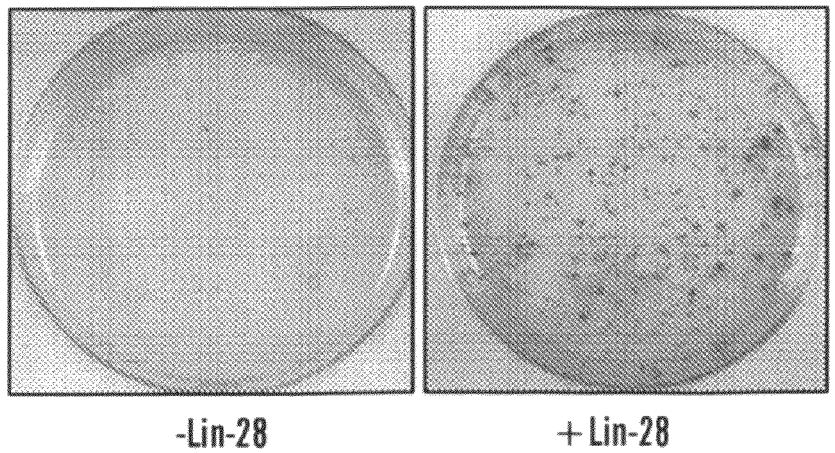

The inventors next sought to determine whether Lin28 could enhance transformation of a mouse lung adenocarcinoma cell line, LKR, generated from a mouse lung adenocarcinoma expressing an activated allele of K-Ras (Kumar, et al., Nat. Genet. 39, 673-677 (2007); Johnson et al., Nature 410, 1111-1116 (2001)). The inventors used retroviral-mediated expression of Lin28 to selectively deplete the levels of mature let-7 family miRs in LKR cells, and demonstrated that this depletion of let-7 family of miRs led to a concomitant increase in levels of K-Ras and c-myc (FIG. 20A-20B). Lin28 expression promoted cellular growth while let-7g over-expression decreased growth rate, as previously reported in Kumar, et al. (Nat. Genet. 39, 673-677 (2007)) (FIG. 20C). When plated at low density, LKR cells expressing Lin28 formed more numerous and larger colonies than did parental LKR cells (FIG. 20D). Together, the these data demonstrate that disruption of let-7 processing via over-expression of Lin28 enhances the proliferative capacity and transformation of cancer cells in three distinct in vitro assays of cellular transformation.

Example 6

The inventors next sought to identify cancer cell lines expressing Lin28/Lin28B, and to determine whether these cell lines were dependent on Lin28/Lin28B for maintaining the transformed state. By using microarray expression profiling on a large panel of human cancer cell lines, the inventors discovered high levels of Lin28 expression in 17/527 cancer cell lines (FIG. 21Ai). As Lin28B is not represented widely on microarrays, the inventors performed quantitative PCR analysis on a select panel of cancer cell lines and discovered that several that express Lin28B (FIG. 21Aii). Interestingly, the inventors discovered that Lin28 was overexpressed largely in cancer cell lines of germ cell origin, while Lin28B appeared to be overexpressed in a broader range of transformed tissue types.

Figure 24A:
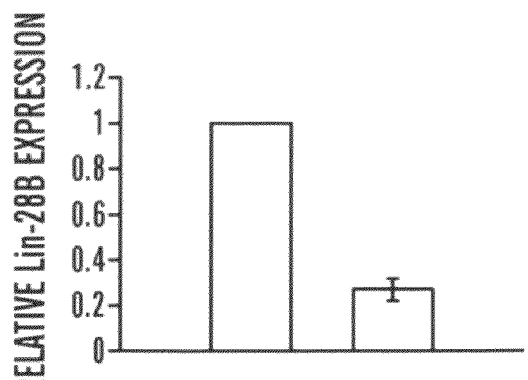
Figure 24B:
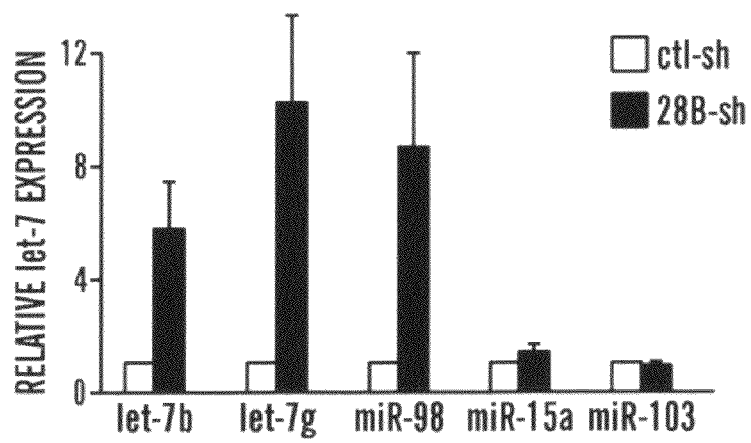
Figure 24C:
Figure 24D:
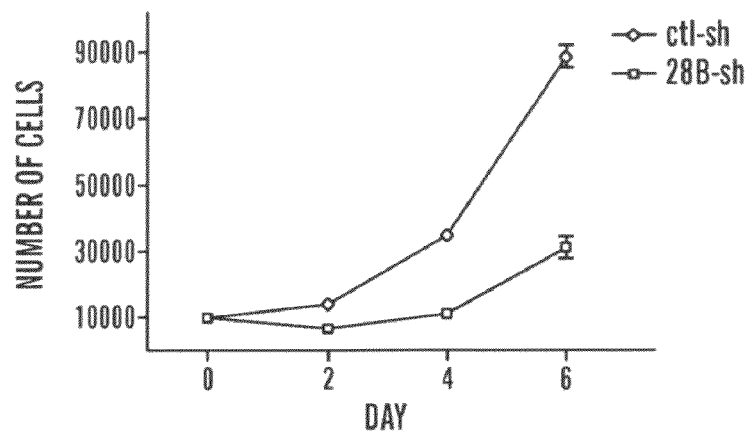
Figure 24E:
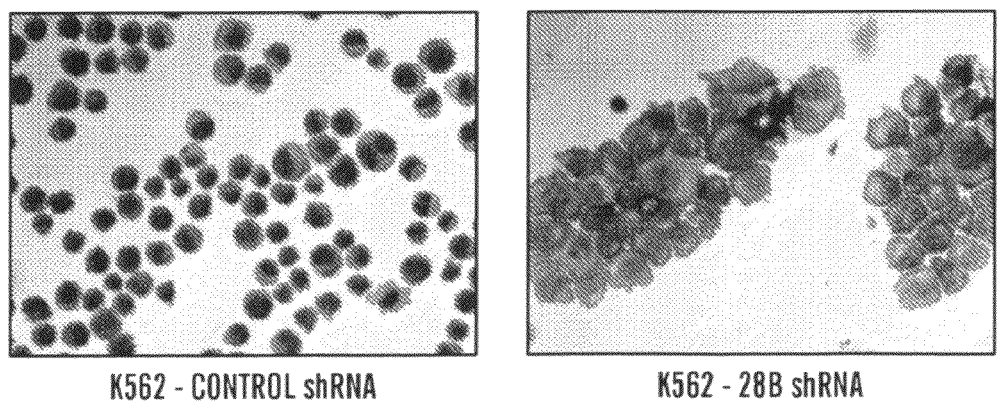

To examine whether Lin28B acts as a physiological repressor of let-7 in human tumor cells, the inventors infected H1299 lung adenocarcinoma cells with an shRNA targeting Lin28B. The inventors demonstrated that depletion of Lin28B via shRNA knockdown led to an increase in levels of mature let-7 family miRs and a concomitant decrease in levels of c-myc protein (FIG. 21C-21D). The inventors also discovered that depletion of Lin28B via shRNA knockdown was accompanied by a decrease in cell growth (FIG. 21E), a decrease in colony forming capacity (FIG. 21F), and an increase in Annexin-positive cells (FIG. 21G), consistent with previous reports that over-expression of let-7 promotes apoptosis (Kumar, et al., Proc. Natl. Acad. Sci. U.S.A 105, 3903-3908 (2008)). The inventors also discovered similar results upon knockdown of Lin28B in K562 (FIG. 24) and Lama-84 cells (FIG. 24), both derived from human patients in the blast crisis phase of chronic myelogenous leukemia (CML). Interestingly, the inventors discovered that knockdown of Lin28B in K562 cells also led to increased cell size, altered cell morphology, and a decreased nuclear/cytoplasmic ratio, all changes associated with cellular differentiation of this cell line (Bruecher-Encke, et al., Leukemia 15, 1424-1432 (2001)) (FIG. 24E).

The inventors herein have demonstrated that aberrant expression of Lin28 and Lin28B is found in a discrete subset of human tumors, and that over-expression of these oncogenes can promote cellular transformation. Low let-7 levels have been reported in various human malignancies, including lung cancer, (Inamura, K. et al. Lung Cancer 58, 392-396 (2007); Takamizawa, et al. Cancer Res 64, 3753-3756 (2004)); hepatocellular carcinoma (Gramantieri, et al., Cancer Res 67, 6092-6099 (2007)); melanoma (Schultz, et al., Cell Res 18, 549-557 (0 AD)); and ovarian cancer (Shell, et al. Proceedings of the National Academy of Sciences 104, 11400-11405 (2007)) and may be associated with poor prognosis. Several mechanisms of miR inactivation in cancer have been reported, including epigenetic silencing (Fazi, et al. Cancer Cell 12, 457-466 (2007); genomic deletion (Ruiz-Ballesteros, et al. Leukemia 21, 2547-2549 (2007)); inactivating mutation (Calin, et al. N. Engl. J. Med. 353, 1793-1801 (2005)) and chromosomal fusion events that eliminate miR target sites (Mayr, et al., Science 315, 1576-1579 (2007)). Nonetheless, copy number loss and epigenetic silencing accounted for only ~50% of miR downregulation in a recent survey of ovarian tumors (Zhang, L. et al. Proceedings of the National Academy of Sciences 105, 7004-7009 (2008)), suggesting that other mechanisms are also at play. The inventors have discovered herein that over-expression of Lin28 and/or Lin28B, which results in blockade of processing of the let-7 family of miRs, is a means of silencing their tumor suppressor function in diverse malignancies.

Lin28 and Lin28B are expressed in various stem cell populations, including embryonic stem cells (Viswanathan, et al., Science 320, 97-100 (2008); Richards, et al., Stem Cells 22, 51-64 (2004), and hematopoietic stem cells derived from cord blood (Eckfeldt, et al. PLoS Biology 3, e254 (2005), although there is scarce expression in most terminally differentiated somatic tissues Yang, et al., Gene Expression Patterns 3, 719-726 (2003)). Over-expression of other stem cell factors, such as Bmi-1 (Lessard, J. et al., Nature 423, 255-260 (2003)), and Oct-4 (Gidekel, et al., Cancer Cell 4, 361-370 (2003); Hochedlinger, K et al., Cell 121, 465-477 (2005) has been reported to promote oncogenesis by driving self-renewal and proliferation. The inventors discovered herein that Lin28 and Lin28B are as similarly important to Oct-4 and Bmi-1, and demonstrate that Lin28/Lin28B function to repress let-7 and contribute to the self-renewal capacity of cancer stem cells (Yu, F. et al. Cell 131, 1109-1123 (2007)). The inventors discovered that Lin28/Lin28B are either expressed in a rare cell-of-origin that acquires additional malignant lesions, or Lin28/Lin28B are independently activated during oncogenesis. In either case, the inventors have used functional experiments to demonstrate that over-expression of Lin28/Lin28B promotes the transformed phenotype to have an increased self-renewal capacity.

Lin28 was recently used together with Oct-4, Nanog, and Sox2 to reprogram human somatic fibroblasts to pluripotency (Yu, J. et al. Science 318, 1917-1920 (2007)). An alternative reprogramming cocktail, Oct4, Sox2, Klf-4, and c-myc, has been used in the reprogramming of both human and mouse somatic fibroblasts (Lowry, et al. Proc. Natl. Acad. Sci. U.S.A 105, 2883-2888 (2008); Park, et al., Nature 451, 141-146 (2008); Takahashi, et al. Cell 131, 861-872 (2007); Takahashi, et al., Cell 126, 663-676 (2006). c-myc greatly enhances the efficiency of reprogramming, its use may have deleterious consequences due to its well-established function as an oncogene (Nakagawa, et al. Nat. Biotechnol. 26, 101-106 (2008)). Accordingly, the inventors discovery that Lin28 inhibits let-7 miR family processing and that inhibition of Lin28 and/or Lin28B can increase the level of let-7 miR tumor suppressor demonstrates that inhibition of Lin28 can be used in lieu of inhibition of c-myc.

The inventors herein have discovered a method to treat cancers, for example by antagonizing (or inhibiting) Lin28 and/or Lin28B function and/or expression in tumors that overexpress these genes would result the reactivatation of the expression of let-7 family tumor suppressors, and may thus be therapeutically beneficial. Furthermore, the inventors have also discovered that the high level of expression of Lin28 and/or Lin28B in a tumor can identify a cancer subject with a poor prognosis to treatment and/or survival.

Example 7

Both the Cold Shock Domains (CSDs) and the Zinc Finger Domains of Lin28 Are Required for pre-let-7 Binding in Vitro and Processing Inhibition in Vivo.

As discussed in Example 2, Lin-28 and/or Lin-28B comprises both a cold-shock domain (CSD) and two CCHC zinc-finger domains which are required for Lin-28 or Lin-28B blocking activity of miR processing. In order to determine which parts and/or which domains of Lin-28/Lin-28B are required for the miRNA processing block the inventors performed mutational analysis of the CSD and two retroviral-type zinc fingers (FIG. 26A). As demonstrated herein, Lin28 and Lin28B can both block let-7 processing and are the only proteins with this combination of motifs (Viswanathan, et al. (2008) Science 320, 97-100; Moss, et al., Cell 88, 637-646; Balzer, et al., (2007) RNA Biol. 4, 16-25). CSDs contain ~70 amino acids that are conserved in prokaryotic and eukaryotic DNA-binding proteins, part of which is highly similar to the RNP-1 RNA-binding motif (Graumann, et al., (1998) Trends Biochem. Sci. 23; 286-290; Landsman, (1992) Nucleic Acids Res. 20, 2861-2864; Schindelin, et al., (1994) Proc. Natl. Acad. Sci. U.S.A. 91, 5119-5123; Frazao, et al., (2006) Nature 443, 110-114 (21-24)). The Cys-Cys-His-Cys (CCHC) type zinc finger domains are found predominantly in nucleocapsid proteins of retroviruses, which are required for viral genome packaging and for the early infection process. Therefore, the inventors assessed if both the CSD and the CCHC domains are important for RNA binding by Lin28. To test this, the inventors generated single amino acid substitutions in either the CSD or the CCHC domains and tested their relative ability to bind to pre-let-7g (FIG. 26B). The inventors discovered single amino acid residues required for binding to pre-let-7g (F47A, F73A, C161A), whereas other residues had no effect (K45A). Next, the inventors assessed the effect of these mutations on Lin28 inhibition of let-7g maturation in vivo (FIG. 26C). The inventors demonstrated that pre-let-7g binding in vitro correlated with and blocking let-7g genesis in vivo. Furthermore, single amino acid substitutions in both the CSD and the CCHC domains abolished both let-7 binding and processing inhibition, thus demonstrating that both domains are necessary for Lin28 function. Accordingly, the inventors demonstrated that an agent which targets the CSD and/or CCHC domain of Lin-28/Lin-28B is useful in the present invention as an agent which inhibits Lin-28 or Lin-28B. Furthermore, the inventors have also demonstrated that a dominant negative Lin-28 and/or Lin-28B polypeptides that has at least one or more mutations in the CSD and/or CCHC domain, such as dominant mutant polypeptides of Lin-28 and/or Lin-28B which have at least one of the following mutations F47A, F73A, C161A are useful in the methods and compositions as disclosed herein as an inhibitors of Lin-28 and/or Lin-28B.

The inventors therefore demonstrate that both the CSD and the CCHC domains are required for the Lin28-mediated block in let-7 processing. Since let-7 miRNA processing is blocked in Lin28-expressing cells, the inventors propose that plasmid-based strategies for ectopic expression of let-7 will be ineffective in certain cell types including embryonic stem cells where these cells express high levels of Lin-28 and/or Lin-28B. Accordingly, therapeutic strategies or approaches for expressing let-7 in these cells will require either concurrent inhibition of Lin-28 and/or Lin-28B, or alternatively changing the pre-let-7 terminal loop sequence to bypass Lin28 regulation.

Vector-based RNA interference is a popular approach for analyzing gene function in mammalian cells (Moffat et al., (2006) Cell 124, 1283-129829). While such vectors typically use standard promoters to express short-hairpin RNAs, some vectors deliver miRNA precursors, including the terminal loop sequence directed against a target mRNA. So far, miR-30 and miR-155 have been utilized in this way (Zeng, et al., (2002) Mol. Cell 9, 1327-1333; Silva, et al, (2005) Nat. Genet. 37, 1281-1288; Chung, et al., (2006) Nucleic Acids Res. 34, e53; Guo, et al., (2006) Gene, 384, 51-61). Based on the inventors discovery herein and the identified additional level of regulation by Lin28 and/or Lin-28B, RNA interference constructs based on prelet-7 should be avoided for certain applications, unless concurrent inhibition of Lin-28 and/or Lin-28B occurs.

REFERENCES

The references cited herein and throughout the application are incorporated herein by reference.

1. Gregory, R. I. et al. The Microprocessor complex mediates the genesis of microRNAs. Nature 432, 235-240 (2004).
2. Denli, A. M., Tops, B. B. J., Plasterk, R. H. A., Ketting, R. F. & Hannon, G. J. Processing of primary microRNAs by the Microprocessor complex. Nature 432, 231-235 (2004).
3. Chendrimada, T. P. et al. TRBP recruits the Dicer complex to Ago2 for microRNA processing and gene silencing. Nature 436, 740-744 (2005).
4. Gregory, R. I., Chendrimada, T. P., Cooch, N. & Shiekhattar, R. Human RISC Couples MicroRNA Biogenesis and Posttranscriptional Gene Silencing. Cell 123, 631-640 (2005).
5. Thomson, J. M. et al. Extensive post-transcriptional regulation of microRNAs and its implications for cancer. Genes Dev. 20, 2202-2207 (2006).
6. Obernosterer, G., Leuschner, P. J. F., Alenius, M. & Martinez, J. Post-transcriptional regulation of microRNA expression. RNA 12, 1161-1167 (2006).
7. Wulczyn, F. G. et al. Post-transcriptional regulation of the let-7 microRNA during neural cell specification. FASEB J. 21, 415-426 (2007).
8. Mineno, J. et al. The expression profile of microRNAs in mouse embryos. Nucl. Acids Res. 34, 1765-1771 (2006).
9. Moss, E. G., Lee, R. C. & Ambros, V. The Cold Shock Domain Protein LIN-28 Controls Developmental Timing in C. elegans and Is Regulated by the lin-4 RNA. Cell 88, 637-646 (1997).
10. Polesskaya, A. et al. Lin-28 binds IGF-2 mRNA and participates in skeletal myogenesis by increasing translation efficiency. Genes Dev. 21, 1125-1138 (2007).
11. Richards, M., Tan, S. P., Tan, J. H., Chan, W. K. & Bongso, A. The Transcriptome Profile of Human Embryonic Stem Cells as Defined by SAGE. Stem Cells 22, 51-64 (2004).
12. Guo, Y. et al. Identification and characterization of Lin-28 homolog B (LIN28B) in human hepatocellular carcinoma. Gene 384, 51-61 (2006).
13. Wang, Y., Medvid, R., Melton, C., Jaenisch, R. & Blelloch, R. DGCR8 is essential for microRNA biogenesis and silencing of embryonic stem cell self-renewal. Nat Genet 39, 380-385 (2007).
14. Moss, E. G. & Tang, L. Conservation of the heterochronic regulator Lin-28, its developmental expression and microRNA complementary sites. Dev. Biol 258, 432-442 (2003).
15. Mayr, C., Hemann, M. T. & Bartel, D. P. Disrupting the Pairing Between let-7 and Hmga2 Enhances Oncogenic Transformation. Science 315, 1576-1579 (2007).
16. Johnson, S. M. et al. RAS Is Regulated by the let-7 MicroRNA Family. Cell 120, 635-647 (2005).

17. Calin, G. A. et al. Frequent deletions and down-regulation of micro-RNA genes miR15 and miR16 at 13q14 in chronic lymphocytic leukemia. PNAS 99, 15524-15529 (2002).
18. Lu, J. et al. MicroRNA expression profiles classify human cancers. Nature 435, 834-838 (2005).
19. Kumar, M. S., Lu, J., Mercer, K. L., Golub, T. R. & Jacks, T. Impaired microRNA processing enhances cellular transformation and tumorigenesis. Nat Genet 39, 673-677 (2007).
20. Kyba, M., Perlingeiro, R. C. R. & Daley, G. Q. HoxB4 Confers Definitive Lymphoid-Myeloid Engraftment Potential on Embryonic Stem Cell and Yolk Sac Hematopoietic Progenitors. Cell 109, 29-37 (2002).
21. Caputi, M., Mayeda, A., Krainer, A. R. & Zahler, A. M. hnRNP A/B proteins are required for inhibition of HIV-1 pre-mRNA splicing. EMBO J. 18, 4060-4067 (1999).

Lu, J. et al. MicroRNA expression profiles classify human cancers. Nature 435, 834-838 (2005).

Thomson, J. M. et al. Extensive post-transcriptional regulation of microRNAs and its implications for cancer. Genes Dev. 20, 2202-2207 (2006).

Kumar, M. S., Lu, J., Mercer, K. L., Golub, T. R., & Jacks, T. Impaired microRNA processing enhances cellular transformation and tumorigenesis. Nat. Genet. 39, 673-677 (2007).

Bussing, I., Slack, F. J., & Grosshans, H. let-7 microRNAs in development, stem cells and cancer. Trends Mol. Med. (2008).

Dahiya, N. et al. MicroRNA expression and identification of putative miRNA targets in ovarian cancer. PLoS. ONE. 3, e2436 (2008).

Schultz, J., Lorenz, P., Gross, G., Ibrahim, S., & Kunz, M. MicroRNA let-7b targets important cell cycle molecules in malignant melanoma cells and interferes with anchorage-independent growth. Cell Res 18, 549-557 (0 AD).

Mayr, C., Hemann, M. T., & Bartel, D. P. Disrupting the Pairing Between let-7 and Hmga2 Enhances Oncogenic Transformation. Science 315, 1576-1579 (2007).

Lee, Y. S. & Dutta, A. The tumor suppressor microRNA let-7 represses the HMGA2 oncogene. Genes Dev. 21, 1025-1030 (2007).

Esquela-Kerscher, A. et al. The let-7 microRNA reduces tumor growth in mouse models of lung cancer. Cell Cycle 7, 759-764 (2008).

Viswanathan, S. R., Daley, G. Q., & Gregory, R. I. Selective blockade of microRNA processing by Lin28. Science 320, 97-100 (2008).

Newman, M. A., Thomson, J. M., & Hammond, S. M. Lin-28 interaction with the Let-7 precursor loop mediates regulated microRNA processing. RNA. 14, 1539-1549 (2008).

Rybak, A. et al. A feedback loop comprising lin-28 and let-7 controls pre-let-7 maturation during neural stem-cell commitment. Nat. Cell Biol. 10, 987-993 (2008).

Mandanas, R. A. et al. Role of p21 RAS in p210 bcr-ab1 transformation of murine myeloid cells. Blood 82, 1838-1847 (1993).

Sawyers, C. L., Callahan, W., & Witte, O. N. Dominant negative MYC blocks transformation by ABL oncogenes. Cell 70, 901-910 (1992).

Daley, G. Q., McLaughlin, J., Witte, O. N., & Baltimore, D. The CML-specific P210 bcr/abl protein, unlike v-abl, does not transform NIH/3T3 fibroblasts. Science 237, 532-535 (1987).

Sawyers, C. L., McLaughlin, J., & Witte, O. N. Genetic requirement for Ras in the transformation of fibroblasts and hematopoietic cells by the Bcr-Abl oncogene. J. Exp. Med. 181, 307-313 (1995).

Mathey-Prevot, B., Nabel, G., Palacios, R., & Baltimore, D. Abelson virus abrogation of interleukin-3 dependence in a lymphoid cell line. Mol. Cell Biol. 6, 4133-4135 (1986).

Azam, M., Seeliger, M. A., Gray, N. S., Kuriyan, J., & Daley, G. Q. Activation of tyrosine kinases by mutation of the gatekeeper threonine. Nat. Struct. Mol. Biol. (2008).

Hantschel, O. et al. A myristoyl/phosphotyrosine switch regulates c-Abl. Cell 112, 845-857 (2003).

Engelman, A. & Rosenberg, N. bcr/ab1 and src but not myc and ras replace v-ab1 in lymphoid transformation. Mol. Cell Biol. 10, 4365-4369 (1990).

Johnson, L. et al. Somatic activation of the K-ras oncogene causes early onset lung cancer in mice. Nature 410, 1111-1116 (2001).

Kumar, M. S. et al. Suppression of non-small cell lung tumor development by the let-7 microRNA family. Proc. Natl. Acad. Sci. U.S.A 105, 3903-3908 (2008).

Bruecher-Encke, B., Griffin, J. D., Neel, B. G., & Lorenz, U. Role of the tyrosine phosphatase SHP-1 in K562 cell differentiation. Leukemia 15, 1424-1432 (2001).

Cheng, L. et al. OCT4: biological functions and clinical applications as a marker of germ cell neoplasia. J. Pathol 211, 1-9 (2007).

Guo, Y. et al. Identification and characterization of lin-28 homolog B (LIN28B) in human hepatocellular carcinoma. Gene 384, 51-61 (2006).

Matsumoto, Y. et al. Clinical classification of hepatoma in Japan according to serial changes in serum alpha-fetoprotein levels. Cancer 49, 354-360 (1982).

Bell, D. A. Origins and molecular pathology of ovarian cancer. Mod Pathol 18, S19-S32 (0 AD).

Shell, S. et al. Let-7 expression defines two differentiation stages of cancer. Proceedings of the National Academy of Sciences 104, 11400-11405 (2007).

Inamura, K. et al. let-7 microRNA expression is reduced in bronchioloalveolar carcinoma, a non-invasive carcinoma, and is not correlated with prognosis. Lung Cancer 58, 392-396 (2007).

Takamizawa, J. et al. Reduced Expression of the let-7 MicroRNAs in Human Lung Cancers in Association with Shortened Postoperative Survival. Cancer Res 64, 3753-3756 (2004).

Gramantieri, L. et al. Cyclin G1 Is a Target of miR-122a, a MicroRNA Frequently Down-regulated in Human Hepatocellular Carcinoma. Cancer Res 67, 6092-6099 (2007).

Fazi, F. et al. Epigenetic Silencing of the Myelopoiesis Regulator microRNA-223 by the AML1/ETO Oncoprotein. Cancer Cell 12, 457-466 (2007).

Ruiz-Ballesteros, E. et al. MicroRNA losses in the frequently deleted region of 7q in SMZL. Leukemia 21, 2547-2549 (2007).

Calin, G. A. et al. A MicroRNA signature associated with prognosis and progression in chronic lymphocytic leukemia. N. Engl. J. Med. 353, 1793-1801 (2005).

Zhang, L. et al. Genomic and epigenetic alterations deregulate microRNA expression in human epithelial ovarian cancer. Proceedings of the National Academy of Sciences 105, 7004-7009 (2008).

Richards, M., Tan, S. P., Tan, J. H., Chan, W. K., & Bongso, A. The Transcriptome Profile of Human Embryonic Stem Cells as Defined by SAGE. Stem Cells 22, 51-64 (2004).

Eckfeldt, C. E. et al. Functional Analysis of Human Hematopoietic Stem Cell Gene Expression Using Zebrafish. PLoS Biology 3, e254 (2005).

Yang, D. H. & Moss, E. G. Temporally regulated expression of Lin-28 in diverse tissues of the developing mouse. Gene Expression Patterns 3, 719-726 (2003).

Lessard, J. & Sauvageau, G. Bmi-1 determines the proliferative capacity of normal and leukaemic stem cells. Nature 423, 255-260 (2003).

Gidekel, S., Pizov, G., Bergman, Y., & Pikarsky, E. Oct-3/4 is a dose-dependent oncogenic fate determinant. Cancer Cell 4, 361-370 (2003).

Hochedlinger, K., Yamada, Y., Beard, C., & Jaenisch, R. Ectopic expression of Oct-4 blocks progenitor-cell differentiation and causes dysplasia in epithelial tissues. Cell 121, 465-477 (2005).

Yu, F. et al. let-7 regulates self renewal and tumorigenicity of breast cancer cells. Cell 131, 1109-1123 (2007).

Yu, J. et al. Induced pluripotent stem cell lines derived from human somatic cells. Science 318, 1917-1920 (2007).

Lowry, W. E. et al. Generation of human induced pluripotent stem cells from dermal fibroblasts. Proc. Natl. Acad. Sci. U.S.A 105, 2883-2888 (2008).

Park, I. H. et al. Reprogramming of human somatic cells to pluripotency with defined factors. Nature 451, 141-146 (2008).

Takahashi, K. et al. Induction of pluripotent stem cells from adult human fibroblasts by defined factors. Cell 131, 861-872 (2007).

Takahashi, K. & Yamanaka, S. Induction of pluripotent stem cells from mouse embryonic and adult fibroblast cultures by defined factors. Cell 126, 663-676 (2006).

Nakagawa, M. et al. Generation of induced pluripotent stem cells without Myc from mouse and human fibroblasts. Nat. Biotechnol. 26, 101-106 (2008).

Lee, J. C. et al. Epidermal growth factor receptor activation in glioblastoma through novel missense mutations in the extracellular domain. PLoS. Med. 3, e485 (2006).

A. M. Denli, B. B. J. Tops, R. H. A. Plasterk, R. F. Ketting, G. J. Hannon, Nature 432, 231-235 (2004).

R. I. Gregory et al., Nature 432, 235-240 (2004).

T. P. Chendrimada et al., Nature 436, 740-744 (2005).

R. I. Gregory, T. P. Chendrimada, N. Cooch, R. Shiekhattar, Cell 123, 631-640 (2005).

G. Obernosterer, P. J. F. Leuschner, M. Alenius, J. Martinez, RNA 12, 1161-1167 (2006).

J. Mineno et al., Nucl. Acids Res. 34, 1765-1771 (2006).

J. M. Thomson et al., Genes Dev. 20, 2202-2207 (2006).

F. G. Wulczyn et al., FASEB J. 21, 415-426 (2007).

M. R. Suh et al., Dev. Biol. 270, 488-498 (2004).

E. G. Moss, R. C. Lee, V. Ambros, Cell 88, 637-646 (1997).

A. Polesskaya et al., Genes Dev. 21, 1125-1138 (2007).

M. Richards, S. P. Tan, J. H. Tan, W. K. Chan, A. Bongso, Stem Cells 22, 51-64 (2004).

Y. Guo et al., Gene 384, 51-61 (2006).

J. Yu et al., Science (2007).

E. Balzer and E. G. Moss, RNA. Biol. 4, 16-25 (2007).

Y. Wang, R. Medvid, C. Melton, R. Jaenisch, R. Blelloch, Nat Genet 39, 380-385 (2007).

M. S. Kumar, J. Lu, K. L. Mercer, T. R. Golub, T. Jacks, Nat Genet 39, 673-677 (2007).

C. Mayr, M. T. Hemann, D. P. Bartel, Science 315, 1576-1579 (2007).

S. M. Johnson et al., Cell 120, 635-647 (2005).

F. Yu et al., Cell 131, 1109-1123 (2007).

G. A. Calin et al., PNAS 99, 15524-15529 (2002).

J. Lu et al., Nature 435, 834-838 (2005).

1. M. Kyba, R. C. R. Perlingeiro, G. Q. Daley, Cell 109, 29-37 (2002).
2. J. M. Thomson et al., Genes Dev. 20, 2202-2207 (2006).
3. R. I. Gregory, T. P. Chendrimada, N. Cooch, R. Shiekhattar, Cell 123, 631-640 (2005).
4. R. I. Gregory et al., Nature 432, 235-240 (2004).
5. M. Caputi, A. Mayeda, A. R. Krainer, A. M. Zahler, EMBO J. 18, 4060-4067 (1999).
6. A. Polesskaya et al., Genes Dev. 21, 1125-1138 (2007).

---

The invention claimed is:

1. A method for promoting miRNA processing of pri-miRNA to mature miRNA in a cancer cell expressing an increased expression level of Lin-28 or Lin-28B as compared to a reference level, the method comprising contacting the cell with at least one agent which inhibits gene expression of Lin-28 polypeptide, wherein the mature miRNA is a tumor suppressor miRNA.

2. The method of claim 1, wherein the cancer cell is a human cancer cell.

3. The method of claim 1, wherein the cancer cell is in vitro, in vivo, in a subject or ex vivo.

4. The method of claim 1, wherein the tumor suppressor_miRNA is a member of the let-7 miRNA family.

5. The method of claim 1, wherein the agent is a nucleic acid or a nucleic acid analogue.

6. The method of claim 1, wherein the cancer cell comprises a breast cancer cell or lung cancer cell.

7. The method of claim 1, wherein the cancer cell comprises a lung adrenocarcinoma cell or a chronic myelogenous leukemia (CML) cell.

8. The method of claim 1, wherein the cancer cell is a pre-cancer cell, a malignant cancer cell, a therapy resistant cancer cell or a cancer stem cell.

9. The method of claim 1, wherein the agent comprises nucleic acids of an SEQ ID NO:7, 8 or 9.

10. The method of claim 1, wherein the agent binds to the let-7 target site in the 3'UTR of Lin-28.

11. A method of treating a cancer in a subject, comprising administering to a subject a pharmaceutical composition comprising an effective amount of at least one agent that inhibits the gene expression of Lin-28, wherein the cancer has an increased expression of Lin-28 or Lin-28B as compared to a reference level.

12. The method of claim 11, wherein the subject is identified to have, or be at risk of an increase in the level of expression and/or activity of Lin-28 or Lin-28B in a biological sample obtained from the subject as compared to a reference level.

13. The method of claim 11, wherein the subject is identified to have, or be at risk of a reduction of the level or expression and/or activity, or loss of expression of a tumor suppressor miRNA in a biological sample as compared to a reference level.

14. The method of claim 13, wherein the tumor suppressor miRNA is a member of the let-7 miRNA family.

15. The method of claim 13, wherein the tumor suppressor miRNA is selected from the group consisting of: miR-16-1, miR-143 and miR-145.

16. The method of claim 11, wherein the cancer is breast cancer or lung cancer.

17. The method of claim 11, wherein the cancer is lung adrenocarcinoma or chronic myelogenous leukemia (CML).

18. The method of claim 11, wherein the cancer is a precancer, malignant cancer, therapy resistant cancer or a cancer comprising cancer stem cells.

19. The method of claim 11, wherein the agent is a nucleic acid or a nucleic acid analogue.

20. The method of claim 11, wherein the agent is a small inhibitory RNA (RNAi), siRNA, microRNA, shRNA, or miRNA.

21. The method of claim 11, wherein the subject is a human.

* * * * *

UNITED STATES PATENT AND TRADEMARK OFFICE
CERTIFICATE OF CORRECTION

PATENT NO. : 8,283,331 B2  Page 1 of 1
APPLICATION NO. : 12/682149
DATED : October 9, 2012
INVENTOR(S) : Richard I. Gregory et al.

It is certified that error appears in the above-identified patent and that said Letters Patent is hereby corrected as shown below:

In the Claims:

At column 131, claim 4, lines 54 and 55, delete "suppressor_miRNA" and insert --suppressor miRNA--

Signed and Sealed this
First Day of January, 2013

David J. Kappos
*Director of the United States Patent and Trademark Office*